US009139625B2

(12) United States Patent
Cutting et al.

(10) Patent No.: US 9,139,625 B2
(45) Date of Patent: Sep. 22, 2015

(54) PATHOGENIC BACTERIA

(75) Inventors: Simon Michael Cutting, Surrey (GB); Hong Anh Huynh, Surrey (GB)

(73) Assignee: Royal Holloway and Bedford New College, Egham, Surrey (GB)

( * ) Notice: Subject to any disclaimer, the term of this patent is extended or adjusted under 35 U.S.C. 154(b) by 0 days.

(21) Appl. No.: 14/118,677

(22) PCT Filed: May 10, 2012

(86) PCT No.: PCT/GB2012/051023

§ 371 (c)(1),
(2), (4) Date: Feb. 7, 2014

(87) PCT Pub. No.: WO2012/160345

PCT Pub. Date: Nov. 29, 2012

(65) Prior Publication Data

US 2014/0141031 A1 May 22, 2014

(30) Foreign Application Priority Data

May 20, 2011 (GB) .................................. 1108505.7

(51) Int. Cl.

| | |
|---|---|
| ***C07K 16/00*** | (2006.01) |
| ***C12P 21/08*** | (2006.01) |
| ***C07K 14/33*** | (2006.01) |
| ***C12Q 1/04*** | (2006.01) |
| ***G01N 33/569*** | (2006.01) |
| ***A61K 39/07*** | (2006.01) |
| ***A61K 39/08*** | (2006.01) |
| ***C07K 16/12*** | (2006.01) |
| *A61K 39/00* | (2006.01) |

(52) U.S. Cl.

CPC ................. *C07K 14/33* (2013.01); *A61K 39/07* (2013.01); *A61K 39/08* (2013.01); *C07K 16/1282* (2013.01); *C12Q 1/04* (2013.01); *G01N 33/56911* (2013.01); *A61K 2039/523* (2013.01); *A61K 2039/542* (2013.01); *A61K 2039/70* (2013.01); *G01N 2333/32* (2013.01); *G01N 2333/33* (2013.01)

(58) Field of Classification Search

CPC ....................................................... C07K 14/33

See application file for complete search history.

(56) References Cited

U.S. PATENT DOCUMENTS

| | | | |
|---|---|---|---|
| 2005/0232947 | A1 | 10/2005 | Cutting |
| 2010/0291100 | A1 | 11/2010 | Macinga |

FOREIGN PATENT DOCUMENTS

| | | |
|---|---|---|
| WO | 2009/078799 | 6/2009 |
| WO | 2010/126670 | 11/2010 |

OTHER PUBLICATIONS

Cerquetti et al (Microb Pathog. vol. 13 (4), pp. 271-279, 1992).*

International Search Report issued in corresponding International Application No. PCT/GB2012/051023, mailed Oct. 31, 2012.

Sebaihia et al., "The multidrug-resistant human pathogen *Clostridium difficile* has a highly mobile, mosaic genome," Nature Genetics, vol. 38, No. 7, Jul. 1, 2006, pp. 779-786.

Databse UniProt [Online], Jul. 25, 2006, "SubName: Full=Putative uncharacterized protein," XP002680260.

Databse UniProt [Online], Jul. 25, 2006, "RecName: Full=Probable peroxiredoxin; EC=1 11.1.15: MNFNYDKDES CDKINSSYNK EDSSYEDFYK HNYKNYDYTS EKNTKKIAMK TLKDSKKLVR," XP002685373.

Stabler et al., "Comparative genome and phenotypic analysis of *Clostridium difficile* 027 strains provides insidght into the evolution of a hypervirulent bacterium," Genome Biology, vol. 10, No. 9, Sep. 25, 2009, pp. R102.1-R102.15.

Database. UniProt [Online], Nov. 24, 2009, "SubName: Full=Putative uncharacterized protein," XP002680261.

Database UniProt [Online], Nov. 24, 2009 "RecName: Full=Probable peroxiredoxin, EC=1.11.1.15," XP002685374.

Lawley et al., "Proteomic and Genomic Characterization of Highly Infectious *Clostridium difficile* 630 Spores," Jounal of Bacteriology, vol. 191, No. 17, Sep. 2009, pp. 5377-5386.

Permpoonpattana et al., "Surface Layers of *Clostridium difficile* Endospores," Journal of Bacteriology, vol. 193, No. 23, Dec. 2011, pp. 6461-6470.

Koschorreck et al., "Cloning and characterzation of new laccase from *Bacillus licheniformis* catalyzing dimerization of phenolic acids," Appl. Microbiol. Biotechnol. (2008), 79:217-224.

Martins et al., "Molecular and Biochemical Characterization of a Hightly Stable Bacterial Laccase That Occurs as a Structural Component of the *Bacillus subtilis* Endospore Coat*" The Journal of Biological Chemistry, vol. 277, No. 21, pp. 18849-18859, 2002.

United Kingdom Search Report dated Sep. 7, 2011 in GB1108505.7.

* cited by examiner

*Primary Examiner* — Albert Navarro

(74) *Attorney, Agent, or Firm* — Banner & Witcoff, Ltd.

(57) ABSTRACT

The invention provides novel surface coat proteins of *Clostridium* spp. spores, and nucleic acids encoding such proteins. The invention extends to various uses of these nucleic acids and proteins, as antigens for use in vaccine design and construction, and to vaccines per se, and in diagnostic test kits and methods for the detection of *Clostridium* spp. infections. In addition, the nucleic acids and proteins can be used as potential targets for therapeutic drugs for the prevention or treatment of *Clostridium* spp. infections.

3 Claims, 23 Drawing Sheets

Figure 3

| **Proteins** | **Orthologues** | | | | | | | | | | | | | | | |
|---|---|---|---|---|---|---|---|---|---|---|---|---|---|---|---|---|
| | *C.d* | *B.s.* | *B.li* | *B.a.* | *B.c.* | *B.t.* | *B.cl.* | *B.h.* | *G.k.* | *O.i.* | *C.p.* | *C.a.* | *C.t.* | *C.th.* | *C.n.* | *C.e.* |
| CotA | + | - | - | - | - | - | - | - | - | - | - | - | - | - | - | - |
| CotB | + | - | + | + | + | + | - | + | - | - | + | + | + | + | - | + |
| CotCA | + | + | + | + | + | + | - | + | + | - | + | + | - | + | + | + |
| CotCB | + | + | + | + | + | + | + | + | + | + | + | + | + | + | + | - |
| CotD | + | + | + | + | + | + | + | + | + | + | + | + | + | + | + | - |
| CotE-perox-chitinase | + | - | - | - | - | - | - | - | - | - | - | - | - | - | - | - |
| CotE-peroxiredoxin | + | + | + | + | + | + | + | + | + | + | + | + | + | + | - | - |
| CotE-chitinase | + | + | + | + | + | + | + | + | - | + | - | - | - | + | - | + |

Figure 4

A (CotCB)

Mn_Catalase

1 MWIYQKTLEH PVNIRQADPR MAKYIMTQLG GPNGELAAAT RYLQQRYTMP TGKSRALLTD IGTEEMAHVE IISSVLYQLI GNCTPEELKA

Mn_Catalase

91 AGLGSNYANF GHGLQPVDSN GVNFTTSYTN VFGDSVTDLH EDMAAEQKAL ATYYQLINLT DDPDLKDILR FLGEREVVHY QRFGEALMDV

181 YEFTECKHQF *

B (CotD)

Ferritin_like_superfamily

1 MWIYQKTIQH PVNIKTCDPR MAKFLITQFG GPNGELAASI RYLSQRYTMP TGNMRALLTD IGTEELAHVE LICTMVYQLT SDASPEELKA

Ferritin_like_superfamily

91 AGLGSNYAQN GYGIYPTDSN GVPFDVRPIA VMSNPVTDLH EDMAAEQKAL ATYYQLINLT DDVDVIDVLK FLGQREIIHY QRFGEALMDA

181 YELEESQKMF *

C (CotCB vs CotD alignment)

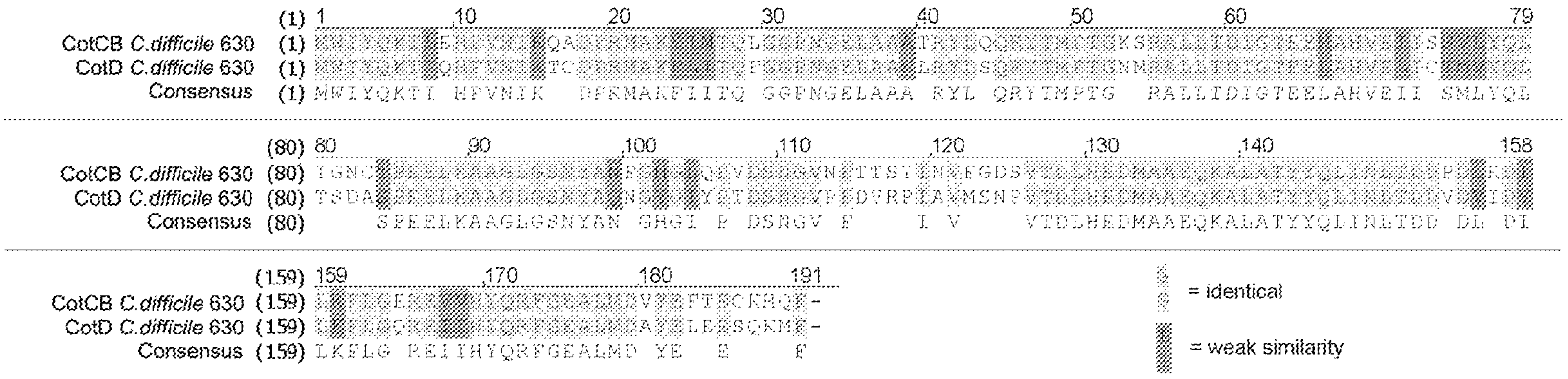

Figure 5

```
                                                             PRX_1cys
1    VIYMPNLPSL GSKAPDFKAN TTNGPIRLSD YKGNWIVLFS HPGDFTPVCT TEFLCFAKYY DEFKKRNTEL IGLSVDSNSS HLAWMYNISL
                                                         PRX_1cys
91   LTGVEIPFPI IEDRDMRIAK LYGMISKPMS DTSTVRSVFI IDNNQILRTI LYYPLTTGRN IPEILRIVDA LQTSDRDNIV TPANWFPGMP
                    PRX_1cys
181  VILPYPKNYK ELKNRVNSCN KKYSCMDWYL CFVPDNYNDE EVSKKIDNTC SWKKEHTKNI ENECNCEHEH HDYLNKALDC KQEHKTDIKD
271  DCNHEKKHTK NTNKVHNSKQ DKFKDKSCDE MNFNYDKDES CDKINSSYNK EDSSYEDFYK HNYKNYDYTS EKNTKKIAMK TLKDSKKLVR
                                                                      GH18_Chitinase
361  PQITDPYNPI VENANCPDIN PIVAEYVLGN PTNVDAQLLD AVIFAFAEID QSGNLFIPYP RFLNQLLALK GEKPSLKVIV AIGGWGAEGF
                                                         GH18_Chitinase
451  SDAALTPTSR YNFARQVNQM INEYALDGID IDWEYPGSSA SGITSRPQDR ENFTLLLTAI RDVIGDDKWL SVAGTGDRGY INSSAEIDKI
                                                         GH18_Chitinase
541  APIIDYFNLM SYDFTAGETG PNGRKHQANL FDSDLSLPGY SVDAMVRNLE NAGMPSEKIL LGIPFYGRLG ATITRTYDEL RRDYINKNGY
                                          GH18_Chitinase
631  EYRFDNTAQV PYLVKDGDFA MSYDDALSIF LKTQYVLRNC LGGVFSWTST YDQANILART MSIGINDPEV LKEELEGIYG QF*
```

= Peroxiredoxin Domain

= Chitinase Domain

* = amino acids involved in catalytic site (chitinase domain)

* = amino acids forming catalytic triad (peroxiredoxin domain)

Figure 9
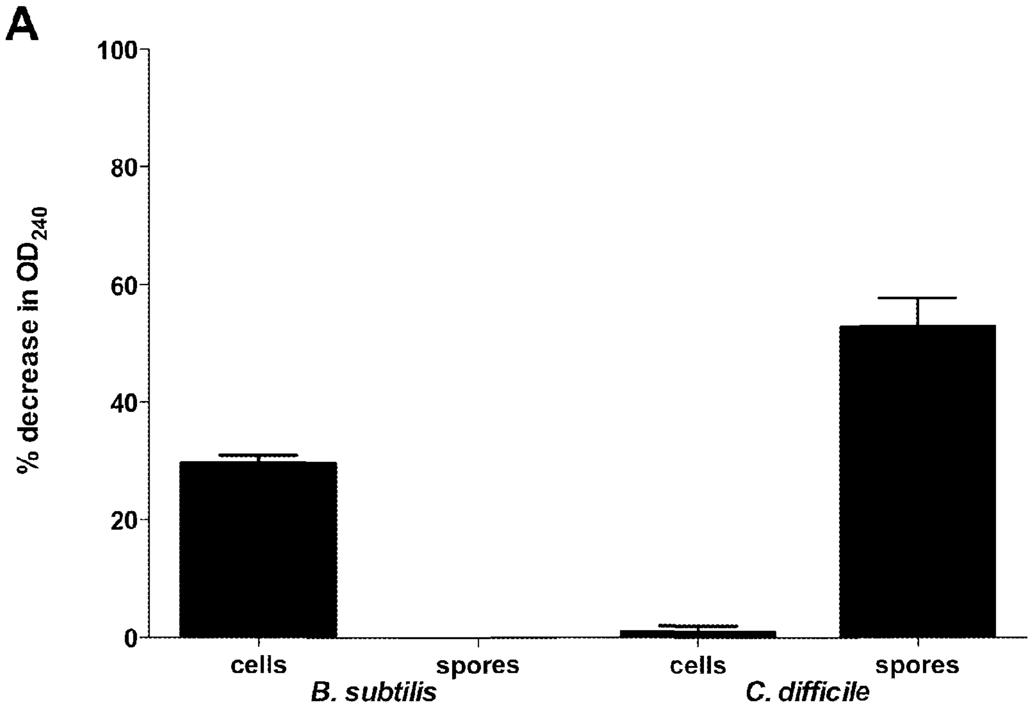
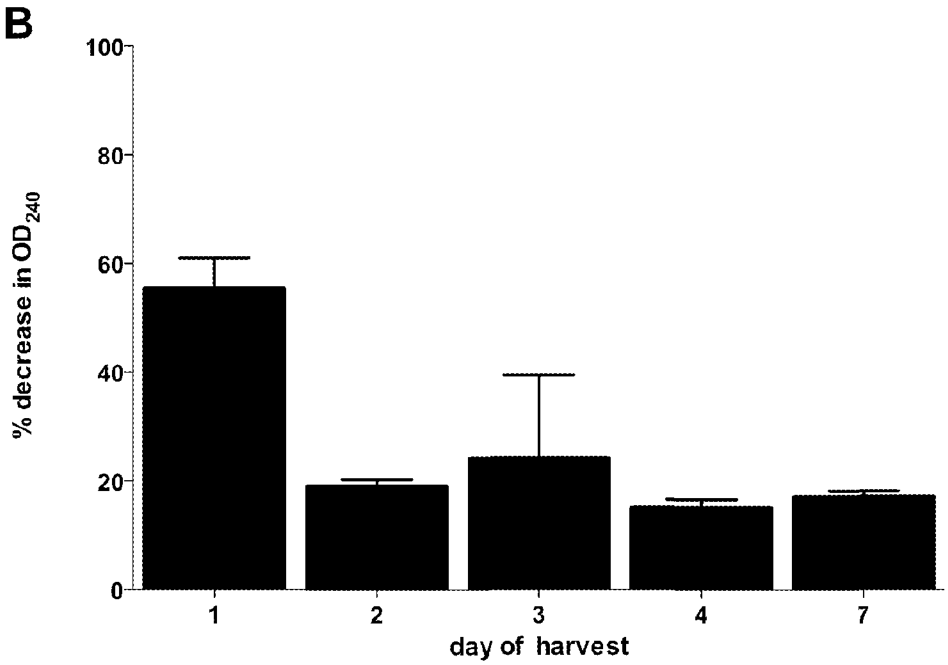

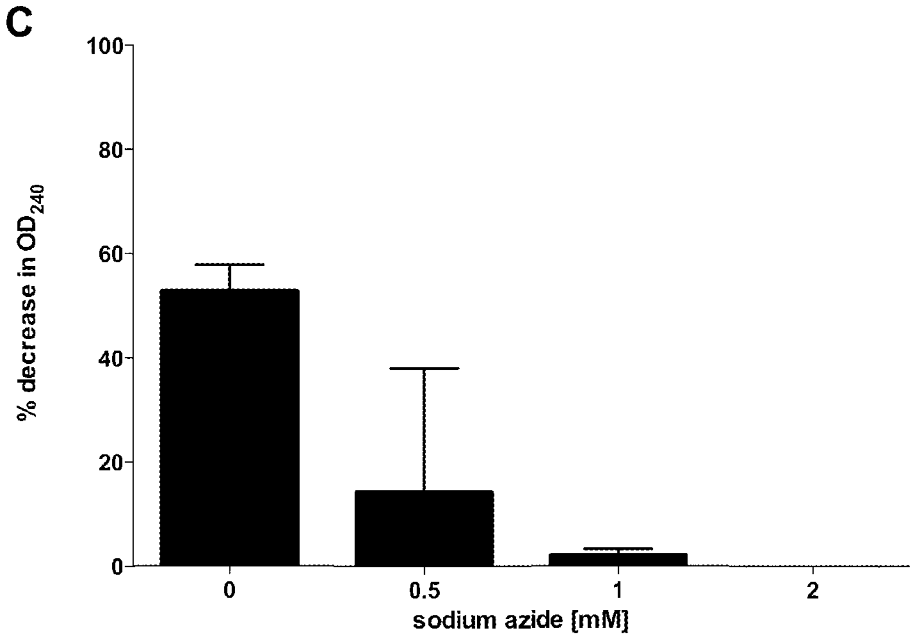
C
100
80
60
40
20
0
% decrease in OD240
0
0.5
1
2
sodium azide [mM]
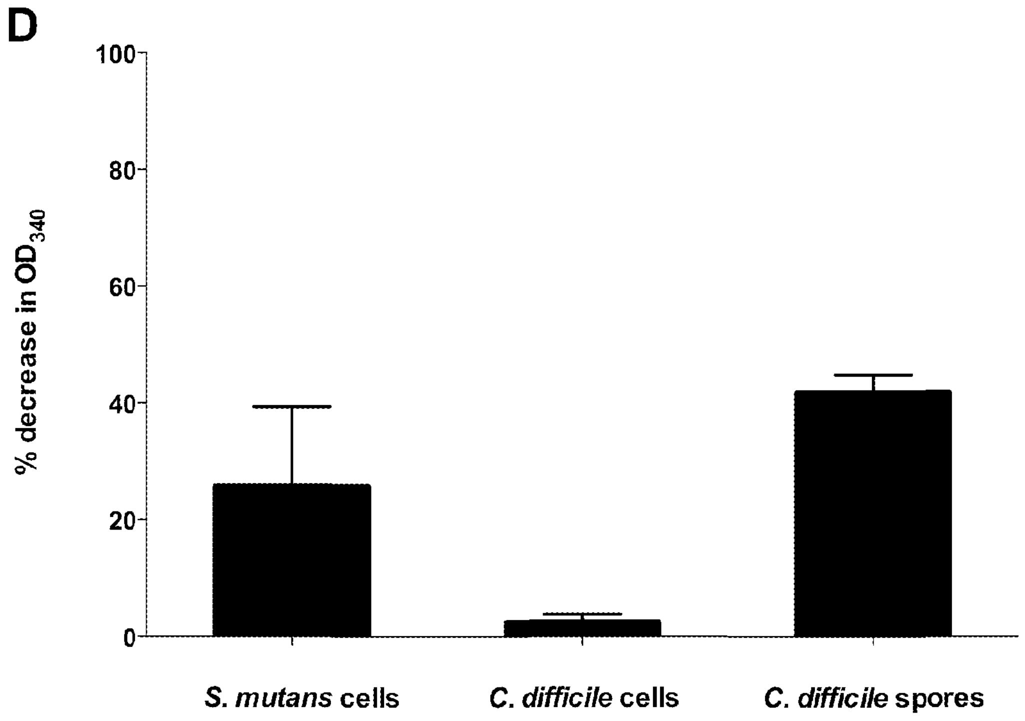
D
100
80
60
40
20
0
% decrease in OD340
S. mutans cells
C. difficile cells
C. difficile spores E
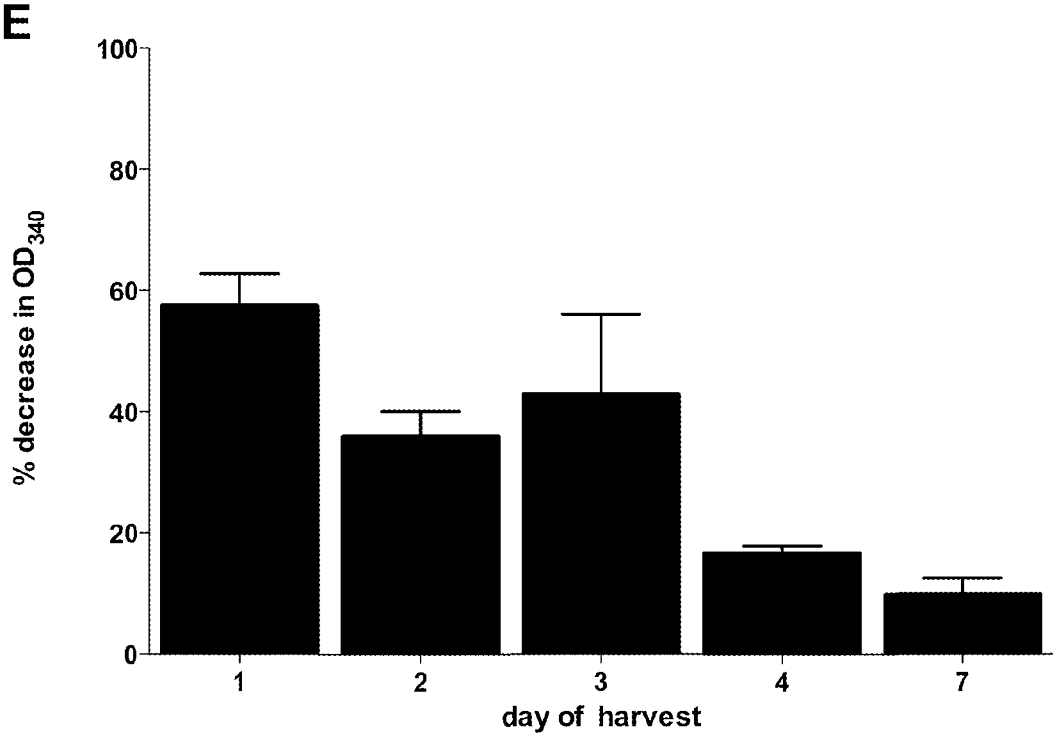
F
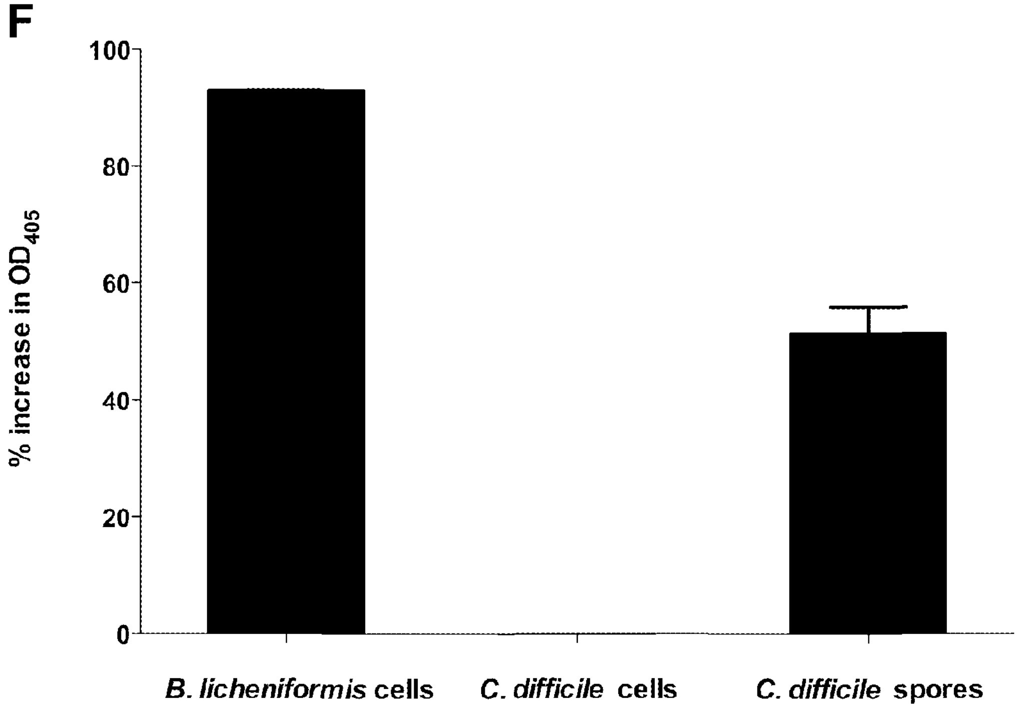

G
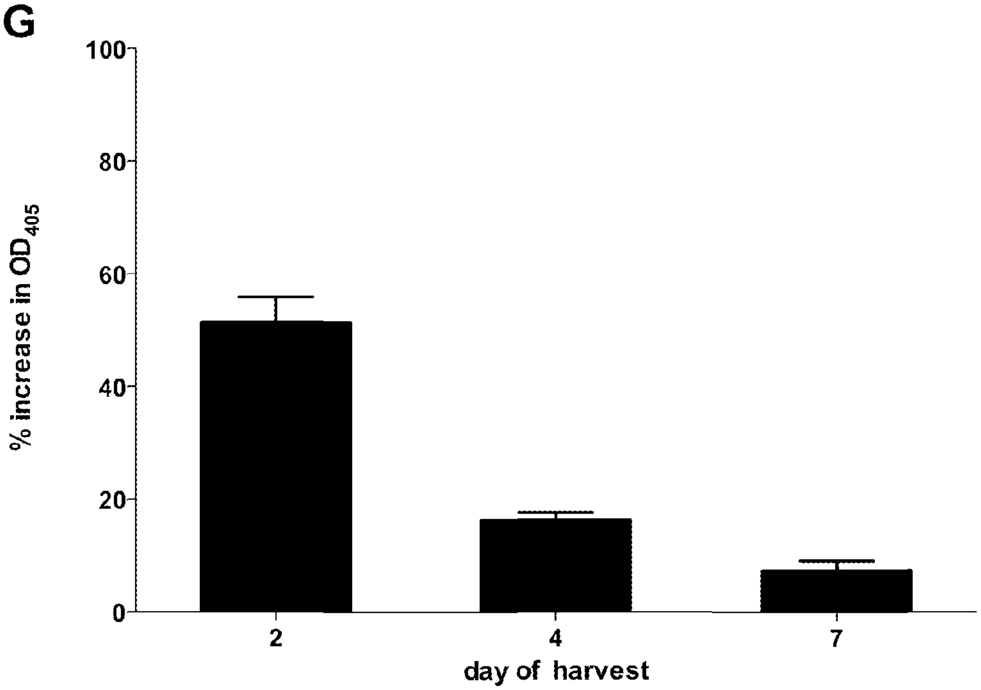
H
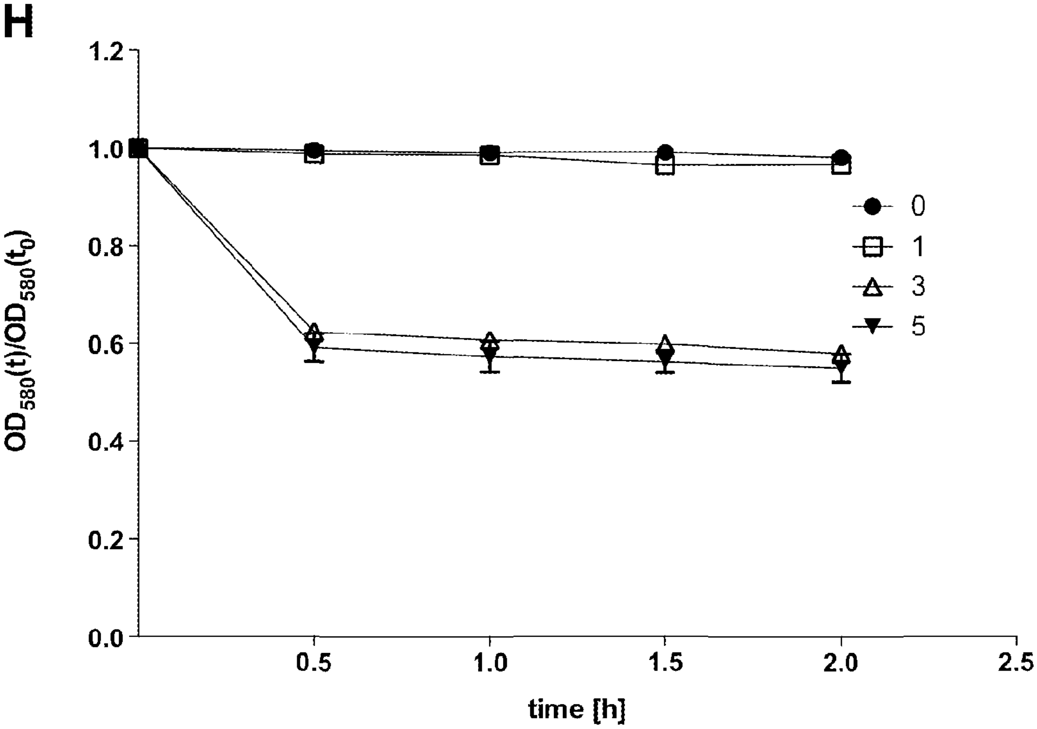

I
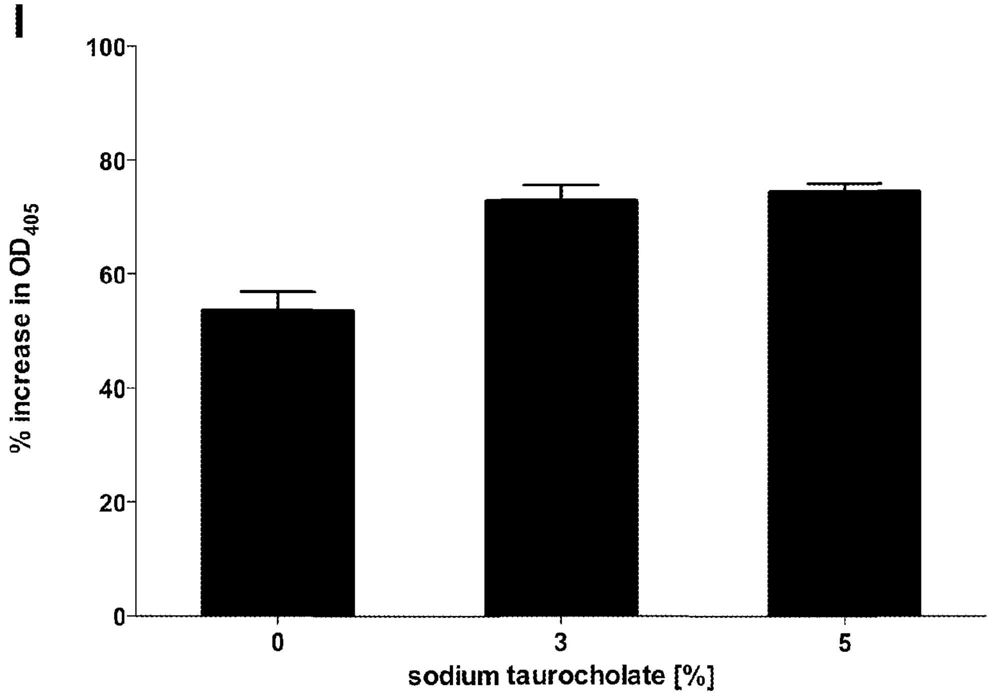
J
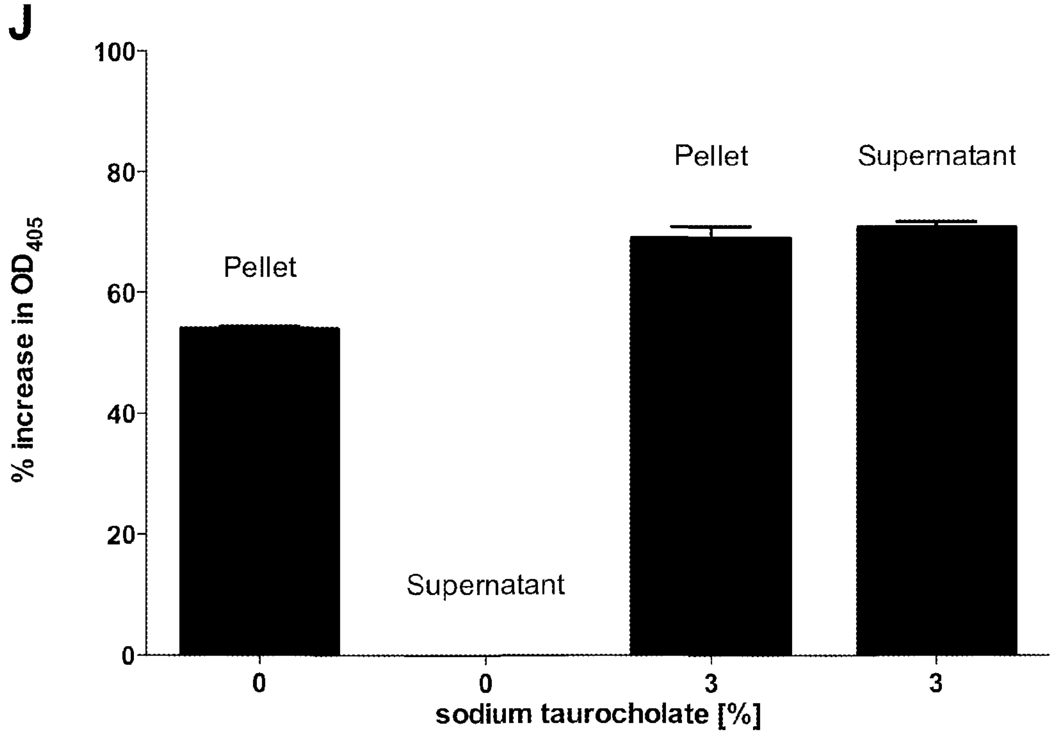

K
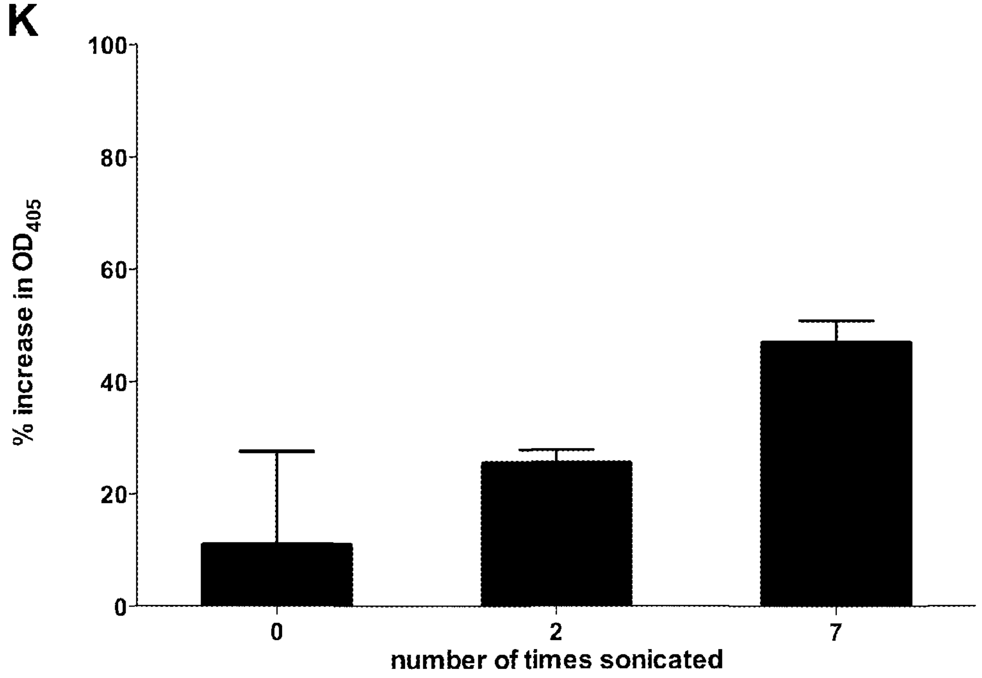
L
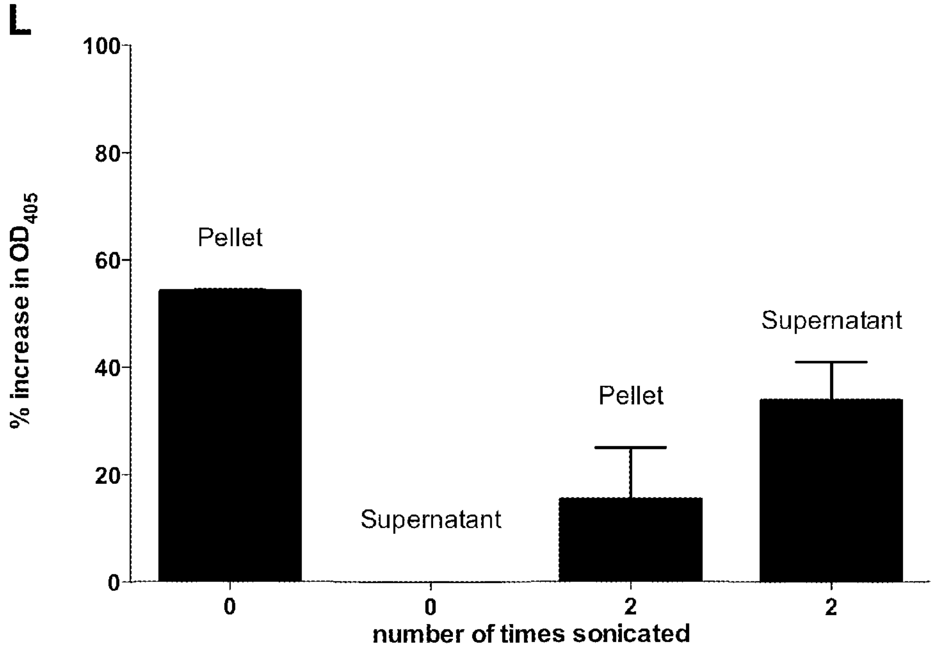

Serum IgG α-CotE

I.M.: Hamsters were immunized with 3 doses of CDTA14 (8μg/dose)

Oral: Hamsters were immunized with 4 does of PP108 ($5x10^{10}$spores/dose)

Figure 24
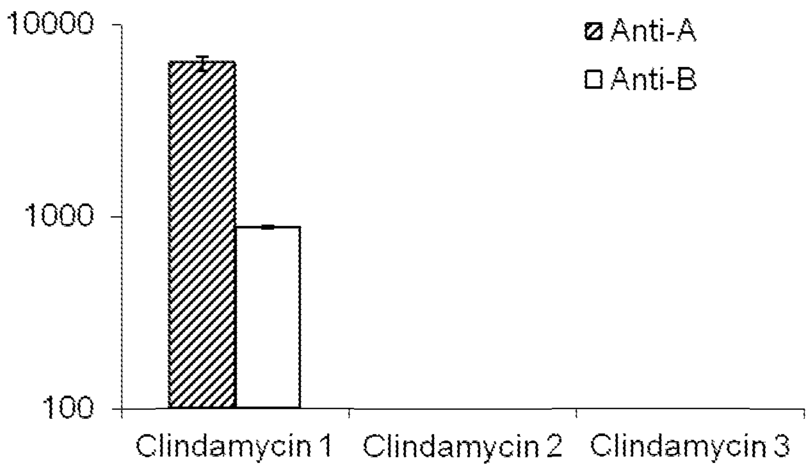
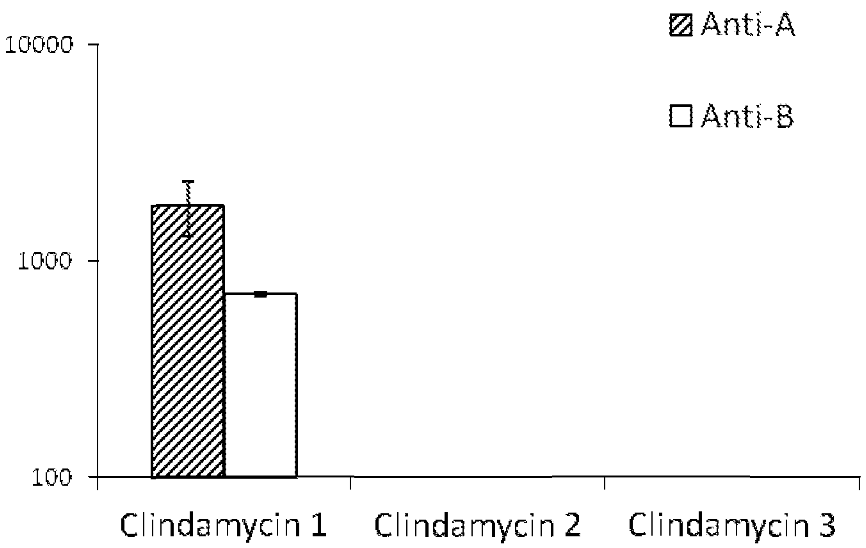

SEQUENCE LISTING

```
<160> NUMBER OF SEQ ID NOS: 24

<210> SEQ ID NO 1
<211> LENGTH: 306
<212> TYPE: PRT
<213> ORGANISM: Clostridium difficile

<400> SEQUENCE: 1

Met Glu Asn Asn Lys Cys Arg Glu Asp Phe Arg Phe Thr Gln Glu Tyr
1               5                   10                  15

Glu Glu Asp Tyr Pro Asn Thr Asn Glu Arg Tyr Tyr Glu Asn Tyr Gln
            20                  25                  30

Val Ala Asp Arg Tyr Tyr Asn Tyr Pro Asn Lys Tyr Lys Glu Pro Lys
        35                  40                  45

Ile Lys Gln Cys Cys Cys Lys Lys Ser Met Arg Glu Ala Leu Glu Leu
    50                  55                  60

Leu Arg Tyr Asp Ala Leu Arg Pro Phe Val Asn Phe Asn Gln Phe Ala
65                  70                  75                  80

Phe Ile Ser Asp Phe Phe Ile Val Gly Ala Asn Leu Val Gly Ile Asp
                85                  90                  95

Leu Ser Ala Pro Pro Lys Asp Asn Leu Ser Gly Leu Asp Gly Thr Phe
            100                 105                 110

Glu Arg Phe Ser Ala Cys Asn Cys Asp Leu Ile Asp Ile Ala Gly Arg
        115                 120                 125

Val Ser Tyr Pro Ile Pro Val Pro Leu Thr Leu Glu Gly Leu Ile Asn
    130                 135                 140
```

-continued

```
Thr Ile Gly Thr Ile Pro Gly Val Ala Glu Leu Ile Ala Leu Ile Asp
145                 150                 155                 160

Ala Val Ile Pro Pro Thr Ile Asp Leu Gly Ala Ile Leu Asp Ala Ile
                165                 170                 175

Leu Ala Ala Ile Ile Asp Phe Ile Leu Ala Ala Ser Thr Pro Leu Ala
            180                 185                 190

Asn Val Asp Leu Ala Ser Leu Cys Asn Leu Lys Ala Val Ala Phe Asp
        195                 200                 205

Ile Thr Pro Ala Asp Tyr Glu Asp Phe Ile Ala Ser Leu Gly Tyr Tyr
    210                 215                 220

Leu Asp Lys Lys His Tyr Lys Glu Cys Asn Cys Asn Cys Asp Cys Asp
225                 230                 235                 240

Asp Cys Cys Cys Cys Asn Lys Gly Ile Leu Asp Asn Leu Tyr Met Ser
                245                 250                 255

Asn Ile Asn Asn Gln Val Thr Val Val Ala Gly Ser Leu Val Leu Thr
            260                 265                 270

Gly Val Glu Val Leu Gly Lys Lys Asn Asp Val Ile Val Leu Gly Asn
        275                 280                 285

Ser Asn Asp Ser Arg Ile Tyr Phe Val Cys Val Asp Ser Ile Asp Tyr
    290                 295                 300

Ile Ala
305


<210> SEQ ID NO 2
<211> LENGTH: 303
<212> TYPE: PRT
<213> ORGANISM: Clostridium difficile

<400> SEQUENCE: 2

Met Ile Asp Asn Gln Lys Tyr Val Ile Leu Ser Leu Glu Leu His Leu
1               5                   10                  15

Phe Phe Ser Arg Ile Met Lys Glu His Ala Leu Phe Leu Glu Ala Gly
            20                  25                  30

Phe Thr Asn Lys Asn Tyr Asn Leu Ala Met Glu Ala Asp His Tyr Lys
        35                  40                  45

Lys Gln Phe Glu Asp Leu Leu Ser Tyr Thr Val Ser Ala Ser Asn Gly
    50                  55                  60

Ile Ile Arg Pro Asp Ile Leu Tyr Ser Glu Glu Leu Val Ile Ile Leu
65                  70                  75                  80

Thr Ser Val Ala Glu Gln Lys Thr Glu Glu Phe Thr Gly Ile Glu Ile
                85                  90                  95

Asn Lys Asn Ile Thr Thr Arg Glu Leu Asn Leu Gln Ser Gly Val Asn
            100                 105                 110

Pro Gln Val Gly Gln Asp Leu Val Asn Tyr Val Ala Gln Leu Asn Ser
        115                 120                 125

Asp Ala Ile Arg Leu Leu Asp Gly Leu Ile Asn Phe Lys Glu Arg Val
    130                 135                 140

Leu Asp Gly Val Leu Ser Cys Thr Ile Phe Thr Ser Asn Tyr Pro Leu
145                 150                 155                 160

Leu Leu Glu His Ile Ile His Glu Ala Asn Leu Tyr Arg Ser Tyr Val
                165                 170                 175

Val Asp Leu Glu Asn Lys Ile Asp Glu Ser Lys Asn Ala Lys Glu Ile
            180                 185                 190

Glu Leu Phe Trp Asp His Ile Met Met Glu His Ala Leu Phe Met Arg
        195                 200                 205
```

-continued

```
Gly Leu Leu Asp Pro Ser Glu Gly Glu Leu Ile Asn Thr Ser Asn Asp
    210                 215                 220

Phe Ala Ile Lys Phe Asn Glu Leu Ile Glu Lys Thr Asn Glu Met Thr
225                 230                 235                 240

Asp Ser Asn Ile Lys Asn Ile Thr Glu Glu Thr Leu Asn Glu Thr Val
                245                 250                 255

Glu Phe Lys Asp Phe Lys Glu Ala Gly Ala Ser Gly Ile Glu Gln Cys
            260                 265                 270

Lys Ile Lys Ser Ile Ile Leu Pro Leu Leu Ala Asp His Val Leu Arg
        275                 280                 285

Glu Ala Asn His Tyr Ile Arg Ile Leu Glu Ser Tyr Lys Asn Met
    290                 295                 300


<210> SEQ ID NO 3
<211> LENGTH: 190
<212> TYPE: PRT
<213> ORGANISM: Clostridium difficile

<400> SEQUENCE: 3

Met Trp Ile Tyr Gln Lys Thr Leu Glu His Pro Val Asn Ile Arg Gln
1               5                   10                  15

Ala Asp Pro Arg Met Ala Lys Tyr Ile Met Thr Gln Leu Gly Gly Pro
            20                  25                  30

Asn Gly Glu Leu Ala Ala Ala Thr Arg Tyr Leu Gln Gln Arg Tyr Thr
        35                  40                  45

Met Pro Thr Gly Lys Ser Arg Ala Leu Leu Thr Asp Ile Gly Thr Glu
    50                  55                  60

Glu Met Ala His Val Glu Ile Ile Ser Ser Val Leu Tyr Gln Leu Ile
65                  70                  75                  80

Gly Ser Cys Thr Pro Glu Glu Leu Lys Ala Ala Gly Leu Gly Ser Asn
                85                  90                  95

Tyr Ala Asn Phe Gly His Gly Leu Gln Pro Val Asp Ser Asn Gly Val
            100                 105                 110

Asn Phe Thr Thr Ser Tyr Ile Asn Val Phe Gly Asp Ser Val Thr Asp
        115                 120                 125

Leu His Glu Asp Met Ala Ala Glu Gln Lys Ala Leu Ala Thr Tyr Tyr
    130                 135                 140

Gln Leu Ile Asn Leu Thr Asp Asp Pro Asp Leu Lys Asp Ile Leu Arg
145                 150                 155                 160

Phe Leu Gly Glu Arg Glu Val Val His Tyr Gln Arg Phe Gly Glu Ala
                165                 170                 175

Leu Met Asp Val Tyr Glu Phe Thr Glu Cys Lys His Gln Phe
            180                 185                 190


<210> SEQ ID NO 4
<211> LENGTH: 190
<212> TYPE: PRT
<213> ORGANISM: Clostridium difficile

<400> SEQUENCE: 4

Met Trp Ile Tyr Gln Lys Thr Ile Gln His Pro Val Asn Ile Lys Thr
1               5                   10                  15

Cys Asp Pro Arg Met Ala Lys Phe Leu Ile Thr Gln Phe Gly Gly Pro
            20                  25                  30

Asn Gly Glu Leu Ala Ala Ser Leu Arg Tyr Leu Ser Gln Arg Tyr Thr
        35                  40                  45
```

```
Met Pro Thr Gly Asn Met Arg Ala Leu Leu Thr Asp Ile Gly Thr Glu
    50                  55                  60

Glu Leu Ala His Val Glu Leu Ile Cys Thr Met Val Tyr Gln Leu Thr
65                  70                  75                  80

Ser Asp Ala Ser Pro Glu Glu Leu Lys Ala Ala Gly Leu Gly Ser Asn
                85                  90                  95

Tyr Ala Gln Asn Gly Tyr Gly Ile Tyr Pro Thr Asp Ser Asn Gly Val
            100                 105                 110

Pro Phe Asp Val Arg Pro Ile Ala Val Met Ser Asn Pro Val Thr Asp
        115                 120                 125

Leu His Glu Asp Met Ala Ala Glu Gln Lys Ala Leu Ala Thr Tyr Tyr
    130                 135                 140

Gln Leu Ile Asn Leu Thr Asp Asp Val Asp Val Ile Asp Val Leu Lys
145                 150                 155                 160

Phe Leu Gly Gln Arg Glu Ile Ile His Tyr Gln Arg Phe Gly Glu Ala
                165                 170                 175

Leu Met Asp Ala Tyr Glu Leu Glu Glu Ser Gln Lys Met Phe
            180                 185                 190


<210> SEQ ID NO 5
<211> LENGTH: 712
<212> TYPE: PRT
<213> ORGANISM: Clostridium difficile

<400> SEQUENCE: 5

Met Ile Tyr Met Pro Asn Leu Pro Ser Leu Gly Ser Lys Ala Pro Asp
1               5                   10                  15

Phe Lys Ala Asn Thr Thr Asn Gly Pro Ile Arg Leu Ser Asp Tyr Lys
            20                  25                  30

Gly Asn Trp Ile Val Leu Phe Ser His Pro Gly Asp Phe Thr Pro Val
        35                  40                  45

Cys Thr Thr Glu Phe Leu Cys Phe Ala Lys Tyr Tyr Asp Glu Phe Lys
    50                  55                  60

Lys Arg Asn Thr Glu Leu Ile Gly Leu Ser Val Asp Ser Asn Ser Ser
65                  70                  75                  80

His Leu Ala Trp Met Tyr Asn Ile Ser Leu Leu Thr Gly Val Glu Ile
                85                  90                  95

Pro Phe Pro Ile Ile Glu Asp Arg Asp Met Arg Ile Ala Lys Leu Tyr
            100                 105                 110

Gly Met Ile Ser Lys Pro Met Ser Asp Thr Ser Thr Val Arg Ser Val
        115                 120                 125

Phe Ile Ile Asp Asn Asn Gln Ile Leu Arg Thr Ile Leu Tyr Tyr Pro
    130                 135                 140

Leu Thr Thr Gly Arg Asn Ile Pro Glu Ile Leu Arg Ile Val Asp Ala
145                 150                 155                 160

Leu Gln Thr Ser Asp Arg Asp Asn Ile Val Thr Pro Ala Asn Trp Phe
                165                 170                 175

Pro Gly Met Pro Val Ile Leu Pro Tyr Pro Lys Asn Tyr Lys Glu Leu
            180                 185                 190

Lys Asn Arg Val Asn Ser Cys Asn Lys Lys Tyr Ser Cys Met Asp Trp
        195                 200                 205

Tyr Leu Cys Phe Val Pro Asp Asn Tyr Asn Asp Glu Glu Val Ser Lys
    210                 215                 220

Lys Ile Asp Asn Thr Cys Ser Trp Lys Lys Glu His Thr Lys Asn Ile
```

-continued

```
225                 230                 235                 240

Glu Asn Glu Cys Asn Cys Glu His Glu His His Asp Tyr Leu Asn Lys
                245                 250                 255

Ala Leu Asp Cys Lys Gln Glu His Lys Thr Asp Ile Lys Asp Asp Cys
            260                 265                 270

Asn His Glu Lys Lys His Thr Lys Asn Thr Asn Lys Val His Asn Ser
        275                 280                 285

Lys Gln Asp Lys Phe Lys Asp Lys Ser Cys Asp Glu Met Asn Phe Asn
    290                 295                 300

Tyr Asp Lys Asp Glu Ser Cys Asp Lys Ile Asn Ser Ser Tyr Asn Lys
305                 310                 315                 320

Glu Asp Ser Ser Tyr Glu Asp Phe Tyr Lys His Asn Tyr Lys Asn Tyr
                325                 330                 335

Asp Tyr Thr Ser Glu Lys Asn Thr Lys Lys Ile Ala Met Lys Thr Leu
            340                 345                 350

Lys Asp Ser Lys Lys Leu Val Arg Pro Gln Ile Thr Asp Pro Tyr Asn
        355                 360                 365

Pro Ile Val Glu Asn Ala Asn Cys Pro Asp Ile Asn Pro Ile Val Ala
    370                 375                 380

Glu Tyr Val Leu Gly Asn Pro Thr Asn Val Asp Ala Gln Leu Leu Asp
385                 390                 395                 400

Ala Val Ile Phe Ala Phe Ala Glu Ile Asp Gln Ser Gly Asn Leu Phe
                405                 410                 415

Ile Pro Tyr Pro Arg Phe Leu Asn Gln Leu Leu Ala Leu Lys Gly Glu
            420                 425                 430

Lys Pro Ser Leu Lys Val Ile Val Ala Ile Gly Gly Trp Gly Ala Glu
        435                 440                 445

Gly Phe Ser Asp Ala Ala Leu Thr Pro Thr Ser Arg Tyr Asn Phe Ala
    450                 455                 460

Arg Gln Val Asn Gln Met Ile Asn Glu Tyr Ala Leu Asp Gly Ile Asp
465                 470                 475                 480

Ile Asp Trp Glu Tyr Pro Gly Ser Ser Ala Ser Gly Ile Thr Ser Arg
                485                 490                 495

Pro Gln Asp Arg Glu Asn Phe Thr Leu Leu Leu Thr Ala Ile Arg Asp
            500                 505                 510

Val Ile Gly Asp Asp Lys Trp Leu Ser Val Ala Gly Thr Gly Asp Arg
        515                 520                 525

Gly Tyr Ile Asn Ser Ser Ala Glu Ile Asp Lys Ile Ala Pro Ile Ile
    530                 535                 540

Asp Tyr Phe Asn Leu Met Ser Tyr Asp Phe Thr Ala Gly Glu Thr Gly
545                 550                 555                 560

Pro Asn Gly Arg Lys His Gln Ala Asn Leu Phe Asp Ser Asp Leu Ser
                565                 570                 575

Leu Pro Gly Tyr Ser Val Asp Ala Met Val Arg Asn Leu Glu Asn Ala
            580                 585                 590

Gly Met Pro Ser Glu Lys Ile Leu Leu Gly Ile Pro Phe Tyr Gly Arg
        595                 600                 605

Leu Gly Ala Thr Ile Thr Arg Thr Tyr Asp Glu Leu Arg Arg Asp Tyr
    610                 615                 620

Ile Asn Lys Asn Gly Tyr Glu Tyr Arg Phe Asp Asn Thr Ala Gln Val
625                 630                 635                 640

Pro Tyr Leu Val Lys Asp Gly Asp Phe Ala Met Ser Tyr Asp Asp Ala
                645                 650                 655
```

```
Leu Ser Ile Phe Leu Lys Thr Gln Tyr Val Leu Arg Asn Cys Leu Gly
            660                 665                 670

Gly Val Phe Ser Trp Thr Ser Thr Tyr Asp Gln Ala Asn Ile Leu Ala
        675                 680                 685

Arg Thr Met Ser Ile Gly Ile Asn Asp Pro Glu Val Leu Lys Glu Glu
    690                 695                 700

Leu Glu Gly Ile Tyr Gly Gln Phe
705                 710
```

<210> SEQ ID NO 6
<211> LENGTH: 918
<212> TYPE: DNA
<213> ORGANISM: Clostridium difficile

<400> SEQUENCE: 6

```
gtggaaaata ataaatgtag agaggacttt agatttacac aagaatatga ggaagattat     60

ccaaatacaa atgaaagata ctatgaaaat tatcaagtag ctgatagata ctataattat    120

ccaaataaat ataaagaacc taaaataaaa caatgttgtt gtaaaaaaag tatgagagag    180

gccttagaac ttctaagata tgatgctcta agaccttttg taaactttaa tcaatttgct    240

tttatctcag atttctttat agtaggtgct aatttggtag gtatagatct ttcagctcct    300

ccaaaagata atttatctgg acttgatggt acttttgaaa gattttctgc ttgtaactgt    360

gatttaatag atatagctgg tagagtatct tatcctattc cagtcccttt aactcttgag    420

ggattaatta atactatagg aactatacca ggagtagctg aattaattgc acttattgat    480

gcagttattc ctcctacgat agaccttggg gctatattag atgcaatact tgctgctata    540

attgatttta tacttgctgc atctactcca ttagcaaacg tagatttagc atcattgtgt    600

aatcttaaag ctgttgcatt tgatattaca cctgcagatt atgaagattt catagcatct    660

ttaggttact atcttgataa aaaacattac aaagaatgta attgtaactg cgattgtgat    720

gattgctgtt gtaataaagg tatcctagat aatctttata tgtcaaatat aaataatcaa    780

gttactgtag tagctggtag tttggttcta actggtgttg aagttctagg taagaaaaat    840

gatgttatag tacttggaaa ttctaatgat tcaagaatat actttgtatg tgtagattct    900

atagattata ttgcataa                                                  918
```

<210> SEQ ID NO 7
<211> LENGTH: 915
<212> TYPE: DNA
<213> ORGANISM: Clostridium difficile

<400> SEQUENCE: 7

```
atgatagata atcaaaaata tgttatttta tcactagaat tacatttatt tttttcaaga     60

attatgaaag agcatgctct ttttttagaa gcaggattca caaataaaaa ttataatctt    120

gctatggaag ctgaccacta taaaaagcaa tttgaagatt tattatcata cactgttagt    180

gctagtaatg gtataattag acctgatata ttatattcag aagaacttgt aactactctc    240

acatcagttg cagaacaaaa aacagaagag tttacaggga tagaaataaa caaaaacatc    300

actacaagag aattaaatct acaaagtggt gtaaacccac aagttggtca agatttagtg    360

aactatgtag ctcaacttaa ctctgatgca ataagattac ttgatgggct tattaatttt    420

aaagaaagag tcttagatgg tgtactatca tgtactatat ttacatcaaa ctaccctcta    480

cttcttgaac atataataca tgaagcaaat ttatatcgtt cttatgtagt tgaccttgaa    540
```

-continued aataaaatag atattgagtc aaaaaacgct aaagaaatag aattattctg ggaccatatt 600
atgatggaac atgctctgtt tatgagagga ttactagacc cctcagaagg tgaactaata 660
aatacttcaa atgattttgc tataaaattt aatgaattaa ttgaaaaaac aaacgaaatg 720
actgattcta atatcaagaa cattacagaa gaaactctaa atgaaactgt tgagtttaaa 780
gattttaaag aagcaggagc atcaggaata gaacagtgta agataaaatc tataatatta 840
ccacttttag cagaccatgt tttaagagag gcaaatcatt atattagaat attggagagt 900
tataaaaaca tgtaa 915

<210> SEQ ID NO 8
<211> LENGTH: 573
<212> TYPE: DNA
<213> ORGANISM: Clostridium difficile

<400> SEQUENCE: 8
atgtggattt atcaaaaaac actggaacat ccagttaaca taagacaagc agaccctaga 60
atggcaaaat atatcatgac tcagttggga ggacctaatg gtgagttggc agctgcaact 120
agatatcttc aacaaagata tactatgcca actggaaaat ctcgtgcact tttaactgat 180
ataggtacag aggaaatggc tcatgttgag ataatttctt cagtgttata tcaattaata 240
ggcaattgta ctccagaaga gcttaaggct gctggacttg gtagtaatta tgctaatttt 300
ggacatggtc ttcagccagt agattctaat ggagtaaact ttactacaag ttatattaat 360
gtctttggcg attcggtaac tgatttacat gaggatatgg ctgctgaaca aaaagcattg 420
gctacgtact atcaattaat aaatttaact gatgaccctg atttgaaaga tatattgaga 480
tttttgggtg agagggaagt agttcactat caaagatttg gtgaagcatt aatggatgtt 540
tatgagttta cagagtgcaa gcatcagttt taa 573

<210> SEQ ID NO 9
<211> LENGTH: 573
<212> TYPE: DNA
<213> ORGANISM: Clostridium difficile

<400> SEQUENCE: 9
atgtggatat atcagaaaac tatacaacac ccagttaata taaaaacttg tgaccctaga 60
atggctaaat ttcttataac tcaatttggt gggccaaatg gggaacttgc tgcatcttta 120
agatatttaa gccaaagata tacaatgcct actggtaata tgcgtgcact tttaacagat 180
attggtacag aagaactagc tcacgttgag cttatatgta ctatggttta tcagttaact 240
tctgatgcaa gcccagaaga gttaaaagct gcaggtcttg gttcaaacta tgctcaaaat 300
ggatatggaa tttatccaac agattcaaat ggtgttccat ttgatgtaag acctatagca 360
gttatgtcaa atcccgtaac cgatttacat gaggatatgg cagctgaaca aaaagcactt 420
gcaacttatt atcaacttat aaacctaaca gatgacgttg atgttataga tgtattaaaa 480
ttcttgggtc aaagagaaat aattcactat caaagatttg gtgaagcttt aatggatgct 540
tacgagttag aagaatctca aaaaatgttc taa 573

<210> SEQ ID NO 10
<211> LENGTH: 2138
<212> TYPE: DNA
<213> ORGANISM: Clostridium difficile

<400> SEQUENCE: 10
gtgatttaca tgccaaattt gccaagttta gggtcaaagg ctcctgattt taaagccaat 60

-continued

```
acaacaaatg gtcctattag actctctgac tataagggta attggattgt tttattttca    120
catcctggtg attttacacc agtttgtact acagaatttt tatgttttgc taaatattat    180
gacgaattta aaaaaagaaa tacagaacta attggtctaa gtgttgatag taacagttca    240
catttagctt ggatgtataa tatttcttta cttacaggtg tagaaattcc atttcctatt    300
atagaagata gagatatgag aattgccaag ttatacggca tgatatcaaa accaatgagt    360
gatacatcaa ctgttcgctc tgtatttatt atagataata atcaaattct aagaacgatt    420
ctttattatc cactaactac aggaagaaat attccagaaa tacttagaat agtagatgca    480
cttcagacta gtgatagaga taatatagtt actcctgcaa actggtttcc tggaatgcca    540
gtgattttac cttatcctaa aaactataag gaattaaaaa atagagttaa cagttgtaat    600
aagaaatatt catgtatgga ctggtactta tgttttgtac cagataatta taatgatgaa    660
gaagtgagca agaaaattga taatattgta gctggaaaaa agaacatact aaaaacattg    720
aaaatgaatg taactgtgaa catgaacatc atgactacct gaacaaagct cttgattgta    780
aacaagaaca caagactgat attaaagatg attgcaatca tgagaaaaaa catactaaaa    840
atactaacaa agttcacaac tccaaacaag ataagtttaa agataagtct tgtgatgaaa    900
tgaattttaa ctatgacaaa gatgaatctt gcgacaaaat aaattctagc tataacaaag    960
aagatagtag ttatgaagat ttctataaac ataattataa aaactacgat tatactagcg   1020
aaaaaaatac taaaaaaata gctatgaaaa ctttaaaaga ttcaaaaaaa ttagttagac   1080
cacaaataac agacccatac aatccaatag ttgaaaatgc aaactgtcca gatataaatc   1140
caattgtagc agaatatgtt cttggaaatc caactaatgt agatgctcaa ctattagatg   1200
cagttatatt tgcttttgct gagatagacc agtctggaaa tttgtttatt ccttatccta   1260
gatttttaaa ccaattactt gctcttaaag gtgaaaaacc tagcttaaaa gtaattgtag   1320
ctattggagg ttggggagct gaaggtttct ctgatgcagc attaacacct acatctagat   1380
ataattttgc aagacaggtc aatcagatga taaatgaata tgctttagat ggaatagata   1440
tagactggga atatcctgga agtagtgcat ctggaataac atcaagacct caagatagag   1500
aaaactttac actcttacta actgccataa gagatgttat aggggatgat aaatggctta   1560
gtgtagctgg aacaggagat agaggatata taaattcaag tgctgaaata gataaaatag   1620
ctcctataat agattatttt aatcttatga gttatgattt tacagcaggt gaaacaggcc   1680
caaatggtag aaaacatcaa gcaaatcttt ttgattcaga cttatctttg ccaggatata   1740
gtgttgatgc aatggtgaga aatcttgaga atgctggaat gccttctgaa aaaatccttc   1800
tcggtatacc attttatgga agattaggtg ctactataac aagaacttat gatgagctta   1860
gaagggatta tataaataaa aatggatatg aatatagatt tgataatact gctcaagttc   1920
cgtatttagt taaggatgga gattttgcaa tgtcatatga tgatgcttta tcaatattct   1980
taaaaactca atatgttctt agaaattgtc taggtggtgt attctcatgg acatcaactt   2040
atgaccaagc aaatatactg gctagaacca tgtctattgg tataaatgac cctgaagtat   2100
taaaagaaga acttgaaggt atttatgggc aattctaa                           2138
```

<210> SEQ ID NO 11
<211> LENGTH: 28
<212> TYPE: DNA
<213> ORGANISM: Clostridium difficile

<400> SEQUENCE: 11

-continued gatccatggc tgtggaaaat aataaatg 28

<210> SEQ ID NO 12
<211> LENGTH: 39
<212> TYPE: DNA
<213> ORGANISM: Clostridium difficile

<400> SEQUENCE: 12
atcctcgagt gcaatataat ctatagaatc tacacatac 39

<210> SEQ ID NO 13
<211> LENGTH: 30
<212> TYPE: DNA
<213> ORGANISM: Clostridium difficile

<400> SEQUENCE: 13
gatccatggc tatagataat caaaaatatg 30

<210> SEQ ID NO 14
<211> LENGTH: 27
<212> TYPE: DNA
<213> ORGANISM: Clostridium difficile

<400> SEQUENCE: 14
atcctcgagc atgtttttat aactctc 27

<210> SEQ ID NO 15
<211> LENGTH: 28
<212> TYPE: DNA
<213> ORGANISM: Clostridium difficile

<400> SEQUENCE: 15
gatccatggc ttggatttat caaaaaac 28

<210> SEQ ID NO 16
<211> LENGTH: 27
<212> TYPE: DNA
<213> ORGANISM: Clostridium difficile

<400> SEQUENCE: 16
atcctcgaga aactgatgct tgcactc 27

<210> SEQ ID NO 17
<211> LENGTH: 28
<212> TYPE: DNA
<213> ORGANISM: Clostridium difficile

<400> SEQUENCE: 17
gatccatggc ttggatatat cagaaaac 28

<210> SEQ ID NO 18
<211> LENGTH: 27
<212> TYPE: DNA
<213> ORGANISM: Clostridium difficile

<400> SEQUENCE: 18
atcctcgagg aacatttttt gagattc 27

<210> SEQ ID NO 19
<211> LENGTH: 24
<212> TYPE: DNA
<213> ORGANISM: Clostridium difficile

<400> SEQUENCE: 19

-continued

```
gatccatggc tccaattgta gcag                                          24


<210> SEQ ID NO 20
<211> LENGTH: 26
<212> TYPE: DNA
<213> ORGANISM: Clostridium difficile

<400> SEQUENCE: 20

atcctcgagg aattgcccat aaatac                                        26


<210> SEQ ID NO 21
<211> LENGTH: 32
<212> TYPE: DNA
<213> ORGANISM: Clostridium difficile

<400> SEQUENCE: 21

cccaagcttg ccatgtggat atatcagaaa ac                                 32


<210> SEQ ID NO 22
<211> LENGTH: 31
<212> TYPE: DNA
<213> ORGANISM: Clostridium difficile

<400> SEQUENCE: 22

ggaattctta ttacaacatt ttttgagatt c                                  31


<210> SEQ ID NO 23
<211> LENGTH: 28
<212> TYPE: DNA
<213> ORGANISM: Clostridium difficile

<400> SEQUENCE: 23

gcggatccac ggattaggcc gtttgtcc                                      28


<210> SEQ ID NO 24
<211> LENGTH: 29
<212> TYPE: DNA
<213> ORGANISM: Clostridium difficile

<400> SEQUENCE: 24

cccaagcttg gatgattgat catctgaag                                     29
```

PATHOGENIC BACTERIA

The present invention relates to pathogenic bacteria, and particularly to *Bacillus* and *Clostridia* species, such as *Clostridium difficile*. The invention is particularly concerned with novel surface coat proteins of *Bacillus* and *Clostridium* spp. spores, and nucleic acids encoding such proteins. The invention extends to various uses of these nucleic acids and proteins, for example as antigens for use in vaccine design and construction, and to vaccines per se, and in diagnostic test kits and methods for the detection of *Clostridium* spp. and *Bacillus* spp. infections. In addition, the nucleic acids and proteins can be used as targets for therapeutic drugs for the prevention or treatment of *Clostridium* spp. and *Bacillus* spp. infections.

There are many pathogenic *Clostridia* species. For example, *C. perfingens* causes gas gangrene in humans and necrotic enteritis in poultry, *C. tetani* is the causative agent of tetanus, and *C. botulinum* causes the flaccid muscular paralysis seen in botulism. *Clostridium difficile* is the most common cause of nosocomial antibiotic-associated diarrhoea in developed countries. Morbidity and mortality rates have been steadily increasing in recent years and could result from the emergence of more virulent strains of *C. difficile*, as well as the changing patterns of antibiotic usage. Recent estimates of *C. difficile* associated diarrhoea (CDAD) in the USA suggest as many as 500,000 cases per year with up to 20,000 mortalities. *C. difficile* colonizes the intestinal tracts of infected patients and antibiotic treatment can promote the overgrowth of this bacterium which, in turn, leads to clinical symptoms of disease including diarrhoea, to, in more severe cases, pseudomembranous colitis.

CDAD is caused by the secretion of two toxins, toxin A (TcdA) and toxin B (TcdB), both monoglucosyltransferases that are cytotoxic, enterotoxic and proinflammatory. CDAD is particularly problematic to treat and contain because of the ability of this bacterium to form robust endospores (spores) that can persist and be easily transferred, person-to-person, in a hospital environment. Currently, the only treatment for CDAD is the use of antibiotics, such as vancomycin and metradinazole, and relapse of CDAD (i.e., diarrhoea recurring within 30 days after the first treatment) is a particular challenge in a hospital environment. Relatively little is known about the role of spores in infection, but hypervirulent *C. difficile* strains, when compared with less virulent strains, show enhanced sporulation efficiencies coupled with superior levels of toxin production. Moreover, evidence has now arisen showing that antibiotic treatment suppresses the diversity of resident intestinal microflora and promotes the growth and proliferation of highly infectious *C. difficile* spores, which is known as a 'supershedder' state. Thus, there is a significant need in the art to provide improved diagnostic tests and medicaments for use in the treatment of infections of *Clostridium* spp. per se, and especially *C. difficile* infections.

The inventors of the present invention were aware that the so-called 'supershedder' state of *C. difficile* spores ends once antibiotic treatment is terminated, and believed that this provides a clue to both the transmission of *C. difficile* infection in humans in a hospital environment and the importance of the spore (rather than the live cell) as the pathogenic agent. The inventors therefore focused their efforts on the spore coat of *C. difficile*, and have made the first attempt at characterizing the spore coat proteins of *C. difficile* 630 (CD630). Using coat protein extractions, the inventors have identified five novel coat proteins, each of which present useful targets for the development of diagnostic tools for detecting *Clostridium* spp. infections, for therapeutic drugs for treating *Clostridium* spp. infections, as well as for the generation of a vaccine for preventing *Clostridium* spp. infections.

Thus, according to a first aspect of the invention, there is provided an isolated polypeptide comprising an amino acid sequence substantially as set out in any one of SEQ ID No:1-5, or a functional fragment or functional variant thereof.

As described in the Examples, the inventors have isolated five spore coat proteins, which are referred to herein as CotA, CotB, CotCB, CotD and CotE. It should be noted that the "Cot" names given to these five novel proteins were arbitrarily given by the inventor and should not be confused with similar names in the technical field, i.e. these names are simply used as an indicator, and it is their DNA and protein sequences, and their functions which are of importance, and not their names as such. Each of these five proteins has been shown to be expressed on the outer layers of a *C. difficile* spore. In addition, at least three, and probably all five proteins, are believed to reside in the outer exosporia) layer of the spore where they would play a key role in spore coat polymerisation and maturation. Therefore, preferably the isolated polypeptide of the invention may be expressed on an outer layer of a bacterial spore, preferably a *Clostridium* spp. or *Bacillus* spp. spore, and most preferably a *C. difficile* spore.

The amino acid sequence of CotA is provided herein as SEQ ID No:1, as follows:

```
                                            SEQ ID No. 1
MENNKCREDFRFTQEYEEDYPNTNERYYENYQVADRYYNYPNKYKEPKI

KQCCCKKSMREALELLRYDALRPFVNFNQFAFISDFFIVGANLVGIDLS

APPKDNLSGLDGTFERFSACNCDLIDIAGRVSYPIPVPLTLEGLINTIG

TIPGVAELIALIDAVIPPTIDLGAILDAILAAIIDFILAASTPLANVDL

ASLCNLKAVAFDITPADYEDFIASLGYYLDKKHYKECNCNCDCDDCCCC

NKGILDNLYMSNINNQVTVVAGSLVLTGVEVLGKKNDVIVLGNSNDSRI

YFVCVDSIDYIA
```

The amino acid sequence of CotB is provided herein as SEQ ID No:2, as follows:

```
                                            SEQ ID No. 2
MIDNQKYVILSLELHLFFSRIMKEHALFLEAGFTNKNYNLAMEADHYKK

QFEDLLSYTVSASNGIIRPDILYSEELVIILTSVAEQKTEEFTGIEINK

NITTRELNLQSGVNPQVGQDLVNYVAQLNSDAIRLLDGLINFKERVLDG

VLSCTIFTSNYPLLLEHIIHEANLYRSYVVDLENKIDESKNAKEIELFW

DHIMMEHALFMRGLLDPSEGELINTSNDFAIKFNELIEKTNEMTDSNIK

NITEETLNETVEFKDFKEAGASGIEQCKIKSIILPLLADHVLREANHYI

RILESYKNM
```

The amino acid sequence of CotCB is provided herein as SEQ ID No:3, as follows:

```
                                            SEQ ID No. 3
MWIYQKTLEHPVNIRQADPRMAKYIMTQLGGPNGELAAATRYLQQRYTM

PTGKSRALLTDIGTEEMAHVEIISSVLYQLIGSCTPEELKAAGLGSNYA

NFGHGLQPVDSNGVNFTTSYINVFGDSVTDLHEDMAAEQKALATYYQLI

NLTDDPDLKDILRFLGEREVVHYQRFGEALMDVYEFTECKHQF
```

The amino acid sequence of CotD is provided herein as SEQ ID No:4, as follows:

SEQ ID No. 4

```
MWIYQKTIQHPVNIKTCDPRMAKFLITQFGGPNGELAASLRYLSQRYTM

PTGNMRALLTDIGTEELAHVELICTMVYQLTSDASPEELKAAGLGSNYA

QNGYGIYPTDSNGVPFDVRPIAVMSNPVTDLHEDMAAEQKALATYYQLI

NLTDDVDVIDVLKFLGQREIIHYQRFGEALMDAYELEESQKMF
```

The amino acid sequence of CotE is provided herein as SEQ ID No:5, as follows:

SEQ ID No. 5

```
MIYMPNLPSLGSKAPDFKANTTNGPIRLSDYKGNWIVLFSHPGDFTPVC

TTEFLCFAKYYDEFKKRNTELIGLSVDSNSSHLAWMYNISLLTGVEIPF

PIIEDRDMRIAKLYGMISKPMSDTSTVRSVFIIDNNQILRTILYYPLTT

GRNIPEILRIVDALQTSDRDNIVTPANWFPGMPVILPYPKNYKELKNRV

NSCNKKYSCMDWYLCFVPDNYNDEEVSKKIDNTCSWKKEHTKNIENECN

CEHEHHDYLNKALDCKQEHKTDIKDDCNHEKKHTKNTNKVHNSKQDKFK

DKSCDEMNFNYDKDESCDKINSSYNKEDSSYEDFYKHNYKNYDYTSEKN

TKKIAMKTLKDSKKLVRPQITDPYNPIVENANCPDINPIVAEYVLGNPT

NVDAQLLDAVIFAFAEIDQSGNLFIPYPRFLNQLLALKGEKPSLKVIVA

IGGWGAEGFSDAALTPTSRYNFARQVNQMINEYALDGIDIDWEYPGSSA

SGITSRPQDRENFTLLLTAIRDVIGDDKWLSVAGTGDRGYINSSAEIDK

IAPIIDYFNLMSYDFTAGETGPNGRKHQANLFDSDLSLPGYSVDAMVRN

LENAGMPSEKILLGIPFYGRLGATITRTYDELRRDYINKNGYEYRFDNT

AQVPYLVKDGDFAMSYDDALSIFLKTQYVLRNCLGGVFSWTSTYDQANI

LARTMSIGINDPEVLKEELEGIYGQF
```

The inventors were surprised to observe that purified *Clostridium* spores carry catalase, peroxiredoxin and chitinase activity, and this was totally unexpected. Thus, in one embodiment, the isolated polypeptide, functional fragment or functional variant thereof, may exhibit catalase activity, which may be manganese catalase activity. Preferably, CotCB (SEQ ID No. 3) and/or CotD (SEQ ID No. 4) may exhibit catalase activity, preferably manganese catalase activity.

In another embodiment, the isolated polypeptide, functional fragment or functional variant thereof, may exhibit peroxiredoxin activity, which may be at an amino-terminus thereof. Preferably, CotE may exhibit peroxiredoxin activity, preferably at its amino-terminus.

In yet another embodiment, the isolated polypeptide, functional fragment or functional variant thereof, may exhibit chitinase activity, which may be at its carboxy-terminus. Preferably, CotE may also exhibit chitinase activity, preferably at its carboxy-terminus. It is preferred that CotE exhibits peroxiredoxin activity, preferably at its amino-terminus, and chitinase activity, preferably at its carboxy-terminus.

Although the inventors were surprised to observe such enzymatic activity in the novel spore coat proteins, they believe that each of these enzymes is expected to play a role in spore coat assembly by polymerizing protein monomers in the inner coat. Furthermore, CotE, in addition to its role in macromolecular degradation, is also believed to play an important role in inflammation, which will be of direct relevance to the development of the gastrointestinal symptoms accompanying *C. difficile* infection.

As described in Example 3, the inventors have demonstrated that each or all of the five spore coat proteins (SEQ ID No. 1-5) can be used as an effective target for detecting the presence of *C. difficile* in an unknown sample, and therefore diagnosing infections with this bacterium. Furthermore, as shown in FIG. 3, the inventors have found that there are a number of orthologues of the *C. difficile* spore surface proteins CotA-E in other spore forming bacterial species. However, as mentioned previously, the CotA-E names of the novel *C. difficile* proteins are not related to proteins having similar names in other organisms. For example, a protein called CotE in *B. subtilis* has no similarity with CotE in *C. difficile*. For example, the table shows orthologues of CotA-E found in *Geobacillus kaustophilus* and *Oceanobacillus iheyensis*, as well as in other common *Clostridium* and *Bacillus* spore formers. Therefore, the inventors believe that, in addition to *C. difficile*, the five spore coat proteins may also be used as a target for detecting the presence of *Clostridium* spp. or *Bacillus* spp. spores present in a sample, and diagnosing infections with these bacteria.

Therefore, according to a second aspect, there is provided use of a polypeptide comprising an amino acid sequence substantially as set out in any one of SEQ ID No:1-5, or a functional fragment or functional variant thereof, in the detection of *Clostridium* spp. or *Bacillus* spp. in a sample.

In a third aspect, there is provided a *Clostridium* spp. or *Bacillus* spp. detection kit, the kit comprising detection means arranged, in use, to detect, in a sample, the presence of a polypeptide comprising an amino acid sequence substantially as set out in any one of SEQ ID No:1-5, or a functional fragment or functional variant thereof, wherein detection of the polypeptide, fragment or variant thereof signifies the presence of *Clostridium* spp. or *Bacillus* spp.

In a fourth aspect, there is provided a method of detecting *Clostridium* spp. or *Bacillus* spp., the method comprising the steps of detecting, in a sample, for the presence of a polypeptide comprising an amino acid sequence substantially as set out in any one of SEQ ID No:1-5, or a functional fragment or functional variant thereof, wherein detection of the polypeptide, fragment or variant thereof signifies the presence of *Clostridium* spp. or *Bacillus* spp.

The use, kit and/or method may each be used to detect for the presence of a spore of *Clostridium* spp. or *Bacillus* spp. in the sample.

The use, kit and/or method may each be used to detect a wide range of *Clostridium* spp. in the sample, for example *C. difficile, C. perfringens, C. tetani, C. botulinum, C. acetobutylicum, C. cellulolyticum, C. novyi* or *C. thermocellum*. It is preferred that *C. difficile* may be detected, and preferably *C. difficile* 630.

The use, kit and/or method may each be used to detect a wide range of *Bacillus* spp. in the sample, for example *B. anthracis, B. cereus, B. clausii, B. halodurans* 130, *B. licheniformis, B. subtilis, B. thuringiensis* serovar *konkkukian* str. 97-27, *Geobacillus kaustophilus* or *Oceanobacillus iheyensis*. The use, kit and/or method may be used to detect *B. anthracis*, which has an exosporium, and proteins exhibiting homology with *C. difficile* proteins.

It will be appreciated that although only one polypeptide selected from SEQ ID No.1-5 needs to be detected to signify the presence (or absence) of *Clostridium* spp. or *Bacillus* spp. in the sample, in some embodiments of the invention, more than one of these five proteins may be detected. Clearly, detection of two, three, four or even five of these proteins will increase the reliability of the diagnosis.

The sample may be obtained from a subject suspected of being infected with *Clostridium* spp. or *Bacillus* spp., for example a patient in a hospital. The sample may be a sample of a bodily fluid into which a *Clostridium* spp. or *Bacillus* spp. infection could result. For example, the sample may comprise blood, urine, saliva or vaginal fluid. *C. difficile* is normally diagnosed from faeces, and so the sample may be a faecal sample. A suitable method for sample preparation may be used prior to carrying out the detection method thereon.

The detection means is preferably arranged to bind to the polypeptide comprising an amino acid sequence substantially as set out in any one of SEQ ID No:1-5, or a functional fragment or functional variant thereof, and thereby form a complex, which complex can be detected, thereby signifying the presence of *Clostridium* spp. or *Bacillus* spp. For example, the detection means may comprise a polyclonal or monoclonal antibody, which may be prepared using techniques known to the skilled person. Polyclonal antisera/antibodies and/or monoclonal antisera/antibodies may first be made against one or more of the polypeptides of the invention acting as antigens, i.e. the *C. difficile* or *Bacillus* spp. spore coat proteins.

The test sample, potentially containing *Clostridium* spp. (preferably *C. difficile*) or *Bacillus* spp., may then be contacted with the detection means in order to allow a complex to form, and this complex may then be subsequently evaluated using an appropriate method to diagnose the presence or absence of the antigen (i.e. SEQ ID No.1, 2, 3, 4 or 5). A positive detection of *Clostridium* spp. or *Bacillus* spp. spores in the sample will occur if they display and carry the relevant antigens that react with one or more of the five appropriate Cot antibodies (exhibiting immunospecificity with CotA-CotE proteins).

The method or kit of the invention may comprise a positive control and/or a negative control. Thus, the test sample may be compared to the positive and/or negative control, in order to determine whether or not the sample is infected with *Clostridium* spp. or *Bacillus* spp. The positive control may comprise SEQ ID No.1, 2, 3, 4 or 5, or a functional fragment or functional variant thereof.

Several embodiments of the kit have been developed. In one embodiment, the kit may comprise latex agglutination. An antibody may be contacted with a test sample, and a positive reaction may be seen by agglutination of a complex comprising the Cot antibody (i.e. CotA-CotE) and the antigen (i.e. Cot protein). The antibody may be first bound to a support structure, for example a latex bead. In the presence of antigen, the support structures will form clumps or coagulate.

In a second embodiment, the kit may comprise lateral flow, which is illustrated in FIGS. 15 and 16. The antibodies may be applied as a thin strip to a suitable membrane. The strip may be pre-soaked with a reagent that, in the presence of the antigen-antibody complex, should one form, produced a detectable result, for example a colour change or reaction that is visible to the naked eye. The sample (containing *Clostridium* spp. or *Bacillus* spp. antigen) may be applied as a drop to one end of the strip. As the aqueous sample diffuses through the membrane, it passes through a band of membrane carrying the reagent. As it moves further, it reaches the band carrying the antibody where it will complex with the antibody and form a defined strip which, in the presence of the reagent (e.g. a colour compound), will be visible to the naked eye as a thin line.

In a third embodiment, the kit may comprise a "dipstick". Antibody may first be applied to one end of a support surface or "dipstick". When the pre-coated support is then spotted onto a test sample, potentially containing *Clostridium* spp. or *Bacillus* spp., the antigen-antibody complex will be visualized using a secondary substrate.

Other techniques can be used to detect the spore coat proteins described herein, all of which rely on the detection of antibody-antigen complexes, for example surface plasmon resonance (SPR), optical methods, fluorescence-based methods or magnetic particles. Another technique which may be used includes ELISA. In this embodiment, the sample may be first diluted, and ELISA may then be used to detect antigen-antibody binding between the Cot antibodies and Cot proteins on the spore coat of any *Clostridium* spp. or *Bacillus* spp. infecting the sample. By dilution of the sample, a good indication of the quantity of antigen on the infecting bacteria in the test sample can be determined.

In a fifth aspect, there is provided an isolated nucleotide sequence encoding the polypeptide, functional variant or fragment thereof, according to the first aspect.

The nucleic acid sequence encoding the polypeptide of SEQ ID No:1 (i.e. CotA) is provided herein as SEQ ID No:6, as follows:

```
                                          SEQ ID No: 6
GTGGAAAATAATAAATGTAGAGAGGACTTTAGATTTACACAAGAATATG

AGGAAGATTATCCAAATACAAATGAAAGATACTATGAAAATTATCAAGT

AGCTGATAGATACTATAATTATCCAAATAAATATAAAGAACCTAAAATA

AAACAATGTTGTTGTAAAAAAAGTATGAGAGAGGCCTTAGAACTTCTAA

GATATGATGCTCTAAGACCTTTTGTAAACTTTAATCAATTTGCTTTTAT

CTCAGATTTCTTTATAGTAGGTGCTAATTTGGTAGGTATAGATCTTTCA

GCTCCTCCAAAAGATAATTTATCTGGACTTGATGGTACTTTTGAAAGAT

TTTCTGCTTGTAACTGTGATTTAATAGATATAGCTGGTAGAGTATCTTA

TTCCTATTCCAGTCCCTTAACTCTTGAGGGATTAATTAATACTATAGGA

ACTATACCAGGAGTAGCTGAATTAATTGCACTTATTGATGCAGTTATTC

CTCCTACGATAGACCTTGGGGCTATATTAGATGCAATACTTGCTGCTAT

AATTGATTTTATACTTGCTGCATCTACTCCATTAGCAAACGTAGATTTA

GCATCATTGTGTAATCTTAAAGCTGTTGCATTTGATATTACACCTGCAG

ATTATGAAGATTTCATAGCATCTTTAGGTTACTATCTTGATAAAAAACA

TTACAAAGAATGTAATTGTAACTGCGATTGTGATGATTGCTGTTGTAAT

AAAGGTATCCTAGATAATCTTTATATGTCAAATATAAATAATCAAGTTA

CTGTAGTAGCTGGTAGTTTGGTTCTAACTGGTGTTGAAGTTCTAGGTAA

GAAAAATGATGTTATAGTACTTGGAAATTCTAATGATTCAAGAATATAC

TTTGTATGTGTAGATTCTATAGATTATATTGCATAA
```

The nucleic acid sequence encoding the polypeptide of SEQ ID No:2 (i.e. CotB) is provided herein as SEQ ID No:7, as follows:

```
                                          SEQ ID No: 7
ATGATAGATAATCAAAAATATGTTATTTTATCACTAGAATTACATTTAT

TTTTTTCAAGAATTATGAAAGAGCATGCTCTTTTTTTAGAAGCAGGATT

CACAAATAAAAATTATAATCTTGCTATGGAAGCTGACCACTATAAAAAG
```

-continued

CAATTTGAAGATTTATTATCATACACTGTTAGTGCTAGTAATGGTATAA

TTAGACCTGATATATTATATTCAGAAGAACTTGTAACTACTCTCACATC

AGTTGCAGAACAAAAAACAGAAGAGTTTACAGGGATAGAAATAAACAAA

AACATCACTACAAGAGAATTAAATCTACAAAGTGGTGTAAACCCACAAG

TTGGTCAAGATTTAGTGAACTATGTAGCTCAACTTAACTCTGATGCAAT

AAGATTACTTGATGGGCTTATTAATTTTAAAGAAAGAGTCTTAGATGGT

GTACTATCATGTACTATATTTACATCAAACTACCCTCTACTTCTTGAAC

ATATAATACATGAAGCAAATTTATATCGTTCTTATGTAGTTGACCTTGA

AAATAAAATAGATATTGAGTCAAAAAACGCTAAAGAAATAGAATTATTC

TGGGACCATATTATGATGGAACATGCTCTGTTTATGAGAGGATTACTAG

ACCCCTCAGAAGGTGAACTAATAAATACTTCAAATGATTTTGCTATAAA

ATTTAATGAATTAATTGAAAAAACAAACGAAATGACTGATTCTAATATC

AAGAACATTACAGAAGAAACTCTAAATGAAACTGTTGAGTTTAAAGATT

TTAAAGAAGCAGGAGCATCAGGAATAGAACAGTGTAAGATAAAATCTAT

AATATTACCACTTTTAGCAGACCATGTTTTAAGAGAGGCAAATCATTAT

ATTAGAATATTGGAGAGTTATAAAAACATGTAA

The nucleic acid sequence encoding the polypeptide of SEQ ID No:3 (i.e. CotCB) is provided herein as SEQ ID No:8, as follows:

SEQ ID No: 8

ATGTGGATTTATCAAAAAACACTGGAACATCCAGTTAACATAAGACAAG

CAGACCCTAGAATGGCAAAATATATCATGACTCAGTTGGGAGGACCTAA

TGGTGAGTTGGCAGCTGCAACTAGATATCTTCAACAAAGATATACTATG

CCAACTGGAAAATCTCGTGCACTTTTAACTGATATAGGTACAGAGGAAA

TGGCTCATGTTGAGATAATTTCTTCAGTGTTATATCAATTAATAGGCAA

TTGTACTCCAGAAGAGCTTAAGGCTGCTGGACTTGGTAGTAATTATGCT

AATTTTGGACATGGTCTTCAGCCAGTAGATTCTAATGGAGTAAACTTTA

CTACAAGTTATATTAATGTCTTTGGCGATTCGGTAACTGATTTACATGA

GGATATGGCTGCTGAACAAAAAGCATTGGCTACGTACTATCAATTAATA

AATTTAACTGATGACCCTGATTTGAAAGATATATTGAGATTTTTGGGTG

AGAGGGAAGTAGTTCACTATCAAAGATTTGGTGAAGCATTAATGGATGT

TTATGAGTTTACAGAGTGCAAGCATCAGTTTTAA

The nucleic acid sequence encoding the polypeptide of SEQ ID No:4 (i.e. CotD) is provided herein as SEQ ID No:9, as follows:

SEQ ID No: 9

ATGTGGATATATCAGAAAACTATACAACACCCAGTTAATATAAAAACTT

GTGACCCTAGAATGGCTAAATTTCTTATAACTCAATTTGGTGGGCCAAA

TGGGGAACTTGCTGCATCTTTAAGATATTTAAGCCAAAGATATACAATG

CCTACTGGTAATATGCGTGCACTTTTAACAGATATTGGTACAGAAGAAC

TAGCTCACGTTGAGCTTATATGTACTATGGTTTATCAGTTAACTTCTGA

TGCAAGCCCAGAAGAGTTAAAAGCTGCAGGTCTTGGTTCAAACTATGCT

-continued

CAAAATGGATATGGAATTTATCCAACAGATTCAAATGGTGTTCCATTTG

ATGTAAGACCTATAGCAGTTATGTCAAATCCCGTAACCGATTTACATGA

GGATATGGCAGCTGAACAAAAAGCACTTGCAACTTATTATCAACTTATA

AACCTAACAGATGACGTTGATGTTATAGATGTATTAAAATTCTTGGGTC

AAAGAGAAATAATTCACTATCAAAGATTTGGTGAAGCTTTAATGGATGC

TTACGAGTTAGAAGAATCTCAAAAAATGTTCTAA

The nucleic acid sequence encoding the polypeptide of SEQ ID No:5 (i.e. CotE) is provided herein as SEQ ID No:10, as follows:

SEQ ID No: 10

GTGATTTACATGCCAAATTTGCCAAGTTTAGGGTCAAAGGCTCCTGATT

TTAAAGCCAATACAACAAATGGTCCTATTAGACTCTCTGACTATAAGGG

TAATTGGATTGTTTTATTTTCACATCCTGGTGATTTTACACCAGTTTGT

ACTACAGAATTTTTATGTTTTGCTAAATATTATGACGAATTTAAAAAAA

GAAATACAGAACTAATTGGTCTAAGTGTTGATAGTAACAGTTCACATTT

AGCTTGGATGTATAATATTTCTTTACTTACAGGTGTAGAAATTCCATTT

CCTATTATAGAAGATAGAGATATGAGAATTGCCAAGTTATACGGCATGA

TATCAAAACCAATGAGTGATACATCAACTGTTCGCTCTGTATTTATTAT

AGATAATAATCAAATTCTAAGAACGATTCTTTATTATCCACTAACTACA

GGAAGAAATATTCCAGAAATACTTAGAATAGTAGATGCACTTCAGACTA

GTGATAGAGATAATATAGTTACTCCTGCAAACTGGTTTCCTGGAATGCC

AGTGATTTTACCTTATCCTAAAAACTATAAGGAATTAAAAAATAGAGTT

AACAGTTGTAATAAGAAATATTCATGTATGGACTGGTACTTATGTTTTG

TACCAGATAATTATAATGATGAAGAAGTGAGCAAGAAAATTGATAATAT

TGTAGCTGGAAAAAAGAACATACTAAAAACATTGAAAATGAATGTAACT

GTGAACATGAACATCATGACTACCTGAACAAAGCTCTTGATTGTAAACA

AGAACACAAGACTGATATTAAAGATGATTGCAATCATGAGAAAAAACAT

ACTAAAAATACTAACAAAGTTCACAACTCCAAACAAGATAAGTTTAAAG

ATAAGTCTTGTGATGAAATGAATTTTAACTATGACAAAGATGAATCTTG

CGACAAAATAAATTCTAGCTATAACAAAGAAGATAGTAGTTATGAAGAT

TTCTATAAACATAATTATAAAAACTACGATTATACTAGCGAAAAAAATA

CTAAAAAAATAGCTATGAAAACTTTAAAAGATTCAAAAAAATTAGTTAG

ACCACAAATAACAGACCCATACAATCCAATAGTTGAAAATGCAAACTGT

CCAGATATAAATCCAATTGTAGCAGAATATGTTCTTGGAAATCCAACTA

ATGTAGATGCTCAACTATTAGATGCAGTTATATTTGCTTTTGCTGAGAT

AGACCAGTCTGGAAATTTGTTTATTCCTTATCCTAGATTTTTAAACCAA

TTACTTGCTCTTAAAGGTGAAAAACCTAGCTTAAAAGTAATTGTAGCTA

TTGGAGGTTGGGGAGCTGAAGGTTTCTCTGATGCAGCATTAACACCTAC

ATCTAGATATAATTTTGCAAGACAGGTCAATCAGATGATAAATGAATAT

GCTTTAGATGGAATAGATATAGACTGGGAATATCCTGGAAGTAGTGCAT

CTGGAATAACATCAAGACCTCAAGATAGAGAAAACTTTACACTCTTACT

-continued

```
AACTGCCATAAGAGATGTTATAGGGGATGATAAATGGCTTAGTGTAGCT

GGAACAGGAGATAGAGGATATATAAATTCAAGTGCTGAAATAGATAAAA

TAGCTCCTATAATAGATTATTTTAATCTTATGAGTTATGATTTTACAGC

AGGTGAAACAGGCCCAAATGGTAGAAAACATCAAGCAAATCTTTTTGAT

TCAGACTTATCTTTGCCAGGATATAGTGTTGATGCAATGGTGAGAAATC

TTGAGAATGCTGGAATGCCTTCTGAAAAAATCCTTCTCGGTATACCATT

TTATGGAAGATTAGGTGCTACTATAACAAGAACTTATGATGAGCTTAGA

AGGGATTATATAAATAAAAATGGATATGAATATAGATTTGATAATACTG

CTCAAGTTCCGTATTTAGTTAAGGATGGAGATTTTGCAATGTCATATGA

TGATGCTTTATCAATATTCTTAAAAACTCAATATGTTCTTAGAAATTGT

CTAGGTGGTGTATTCTCATGGACATCAACTTATGACCAAGCAAATATAC

TGGCTAGAACCATGTCTATTGGTATAAATGACCCTGAAGTATTAAAAGA

AGAACTTGAAGGTATTTATGGGCAATTCTAA
```

Accordingly, the nucleotide sequence of the fifth aspect may comprise a nucleic acid sequence substantially as set out in any one of SEQ ID No's: 6 to 10, or a functional variant or a fragment thereof.

In a sixth aspect, there is provided a genetic construct comprising the nucleotide sequence of the fifth aspect.

Genetic constructs of the invention may be in the form of an expression cassette, which may be suitable for expression of the encoded polypeptide in a host cell. The genetic construct may be introduced in to a host cell without it being incorporated in a vector. For instance, the genetic construct, which may be a nucleic acid molecule, may be incorporated within a liposome or a virus particle. Alternatively, a purified nucleic acid molecule (e.g. histone-free DNA, or naked DNA) may be inserted directly into a host cell by suitable means, e.g. direct endocytotic uptake. The genetic construct may be introduced directly in to cells of a host subject (e.g. a bacterial cell) by transfection, infection, electroporation, microinjection, cell fusion, protoplast fusion or ballistic bombardment. Alternatively, genetic constructs of the invention may be introduced directly into a host cell using a particle gun. Alternatively, the genetic construct may be harboured within a recombinant vector, for expression in a suitable host cell.

In a seventh aspect, there is provided a recombinant vector comprising the genetic construct according to the sixth aspect.

The recombinant vector may be a plasmid, cosmid or phage. Such recombinant vectors are useful for transforming host cells with the genetic construct of the sixth aspect, and for replicating the expression cassette therein. The skilled technician will appreciate that genetic constructs of the invention may be combined with many types of backbone vector for expression purposes. Examples of suitable backbone vectors include pDG364 (see FIG. 10) and pDG1664. Recombinant vectors may include a variety of other functional elements including a suitable promoter to initiate gene expression. For instance, the recombinant vector may be designed such that it autonomously replicates in the cytosol of the host cell. In this case, elements which induce or regulate DNA replication may be required in the recombinant vector. Alternatively, the recombinant vector may be designed such that it integrates into the genome of a host cell, for example when the backbone vector is pJH101. In this case, DNA sequences which favour targeted integration (e.g. by homologous recombination) are envisaged.

The recombinant vector may also comprise DNA coding for a gene that may be used as a selectable marker in the cloning process, i.e. to enable selection of cells that have been transfected or transformed, and to enable the selection of cells harbouring vectors incorporating heterologous DNA. For example, chloramphenicol resistance is envisaged. Alternatively, the selectable marker gene may be in a different vector to be used simultaneously with vector containing the gene of interest. The vector may also comprise DNA involved with regulating expression of the coding sequence, or for targeting the expressed polypeptide to a certain part of the host cell.

In an eighth aspect, there is provided a host cell comprising the genetic construct according to the sixth aspect, or the recombinant vector according to the seventh aspect.

The host cell may be a bacterial cell, for example *Bacillus subtilis* or *Salmonella*. Alternatively, the host cell may be an animal cell, for example a mouse or rat cell. It is preferred that the host cell is not a human cell. The host cell may be transformed with genetic constructs or vectors according to the invention, using known techniques. Suitable means for introducing the genetic construct into the host cell will depend on the type of cell.

In a ninth aspect, there is provided a transgenic host organism comprising at least one host cell according to the eighth aspect.

The genome of the host cell or the transgenic host organism of the invention may comprise a nucleic acid sequence encoding a polypeptide, variant or fragment according to the first aspect. The host organism may be a multicellular organism, which is preferably non-human. For example, the host organism may be a mouse or rat. The host may be a bacterium. As described in Example 2, the host may be used for development of a vaccine for immunising a subject against infections with *Clostridium* spp., preferably *C. difficile* infections. Indeed, knowledge of the amino acid sequences of each of the five spore coat proteins described herein can be harnessed in the development of a vaccine.

Thus, in a tenth aspect, there is provided use of a polypeptide comprising an amino acid sequence substantially as set out in any one of SEQ ID No:1-5, or a functional fragment or functional variant thereof, in the development of a vaccine for combating an infection with *Clostridium* spp. or *Bacillus* spp.

In an eleventh aspect, there is provided a vaccine comprising a polypeptide comprising an amino acid sequence substantially as set out in any one of SEQ ID No:1-5, or a functional fragment or functional variant thereof.

Preferably, the vaccine is for combating a *C. difficile* or *Bacillus* spp. infection. In the development of a vaccine, it is preferred that any or all of SEQ ID No:1-5 or fragments or variants thereof may be used as an antigen for triggering an immune response in a subject which is to be vaccinated. The vaccine may be prophylactic or therapeutic.

Accordingly, in a twelfth aspect, there is provided use of a polypeptide comprising an amino acid sequence substantially as set out in any one of SEQ ID No:1-5, or a functional fragment or functional variant thereof, for stimulating an immune response in a subject.

The polypeptide, fragment or variant may be administered directly into a subject to be vaccinated on its own, i.e. just one or more polypeptide comprising an amino acid sequence substantially as set out in any one of SEQ ID No:1-5, or a functional fragment or functional variant thereof. The polypeptide may be administered by injection or mucosally. It will be appreciated that administration, into a subject to be vaccinated, of a polypeptide, fragment or variant of the invention will result in the production of corresponding antibodies exhibiting immunospecificity for the polypeptide, fragment or variant, and that these antibodies aid in preventing a subsequent infection with *Clostridium* spp. or *Bacillus* spp.

The skilled person will appreciate that there are various ways in which a vaccine could be made based on the antigenic fragments represented as SEQ ID No's: 1-5, and fragments thereof. For example, genetically engineered vaccines may be constructed where the heterologous antigen (i.e. the polypeptide, fragment or variant thereof) is fused to a promoter or gene that facilitates expression in a host vector (e.g., a bacterium), a virus (e.g., Adenovirus). Alternatively, the vaccine may be a DNA molecule based on nucleotide sequences, SEQ ID No's: 6-10. The vaccine may comprise an excipient, which may act as an adjuvant. Thus, in another embodiment, the antigenic peptide in the vaccine may be combined with a microparticulate adjuvant, for example liposomes, or an immune stimulating complex (ISCOMS). The peptide may be combined with an adjuvant, such as cholera toxin, or a squalene-like molecule.

Example 2 describes another way in which a vaccine may be prepared. Firstly, one of the five novel spore coat proteins, or fragment or variant thereof according to the first aspect may be chosen as an antigen against which a subsequently vaccinated subject will produce corresponding antibodies. The sequence of the designated gene encoding the designated spore coat protein may then be cloned into a suitable vector to form a genetic construct of the sixth aspect of the invention. The designated gene may be CotA (SEQ ID No.6), CotB (SEQ ID No.7), CotCB (SEQ ID No.8), CotD (SEQ ID No.9) or CotE (SEQ ID No.10). A suitable vector may be pDG364 shown in FIG. 10. However, another suitable vector may be pDG1664. These vectors enable the ectopic insertion into a suitable host bacterial cell, for example *Bacillus subtilis*.

The DNA sequence encoding the designated antigen may be inserted into any known target gene from the host bacterial cell (e.g. *B. subtilis*) that encodes a known protein. The DNA sequence encoding the antigen may be inserted into a multiple cloning site flanked by at least part of an amyE gene, which encodes an alpha amylase. Alternatively, the DNA sequence encoding the antigen may be inserted into a multiple cloning site flanked by at least part of a thrC gene. It will be appreciated that the invention is not limited to insertion at amyE and thrC genes. Insertion into any gene is permissible as long as the growth and sporulation of the host organism is not impaired, i.e. the insertion is functionally redundant.

The thus created genetic construct may be used to transform a vegetative mother cell by double cross-over recombination. Alternatively, the genetic construct may be an integrative vector (e.g. pJH101), which may be used to transform a vegetative mother cell by single cross-over recombination.

The construct may comprise a drug-resistance gene that is selectable in the host cell, for example chloramphenicol resistance. After confirmation of the plasmid clone, the plasmid may then be introduced into a host cell by suitable means. The host may be a *B. subtilis* cell, which itself produces spores. Transformation may be DNA-mediated transformation or by electroporation. Selection may be achieved by testing for drug resistance carried by the plasmid, and now introduced into the genome.

Expression of the hybrid or chimeric gene may be confirmed using Western blotting and probing of size-fractionated proteins (SDS-PAGE) using antibodies that recognize the introduced antigen (i.e. CotA, CotB, CotCB, CotD and/or CotE). If the *C. difficile* gene fused to the *B. subtilis* gene is correctly expressed, a new band appears which is recognized only by the antibody, and not normally found in *B. subtilis*. Other techniques that may be used are immuno-fluorescence microscopy and FACS analysis that can show surface expression of antigens on the host's spore surface.

The resultant spores may be administered to a subject (i.e. vaccination) by an oral, intranasal and/or rectal route. The spores may be administered using one or more of the said oral or intranasal or rectal routes. Oral administration of spores may be suitably via a tablet a capsule or a liquid suspension or emulsion. Alternatively the spores may be administered in the form of a fine powder or aerosol via a Dischaler® or Turbohaler®. Intranasal administration may suitably be in the form of a fine powder or aerosol nasal spray or modified Dischaler® or Turbohaler®. Rectal administration may suitably be via a suppository. The spores according to the invention are preferably heat-inactivated prior to administration such that they do not germinate into vegetative cells.

A suitable dosing regime may be used depending on the organism to be vaccinated. For example, for a human subject to be vaccinated, normally three doses (100-500 mg as a tablet or capsule carrying about $2\times10^{10}$ spores) at 2-week intervals may be used. Blood may be withdrawn for analysis of serum (IgG) responses. Saliva, vaginal fluids or faeces may be taken for analysis of mucosal (secretory IgA) responses. Indirect ELISA may be used to analyse antibody responses in serum and mucosal samples, to gauge the efficacy of the vaccination.

As described in the Examples, the inventors have shown that CotE competes with *C. difficile* toxin A for the toxin A binding receptor in the gut epithelium, and this is thought to be brought about by CotE binding to the GlcNAc motif in the Galα1-3Galβ1-4GlcNAc binding site. The inventors have demonstrated in the examples that CotE may be used to treat recolonisation and relapse of the infection, and FIG. 25 illustrates a possible model for relapse and remission. Spores and toxin A bind to the same receptor, in the case of spores, by virtue of the CotE chitinase on the spore surface.

Thus, the polypeptide, fragment or variant may be used to treat or prevent relapse/recolonisation of the infection. Preferably, CotE is used to treat or prevent relapse of the infection.

In addition, in view of these results, the inventors believe that the efficacy of the vaccine of the eleventh aspect may be further improved by combining toxin A with the polypeptide comprising an amino acid sequence substantially as set out in any one of SEQ ID No:1-5, or a functional fragment or functional variant thereof.

Thus, the vaccine may further comprise toxin A, or a functional variant or fragment thereof. Preferably, the variant or fragment is capable of binding to the GlcNAc motif. In another embodiment, the vaccine may further comprise toxin B, or a functional variant or fragment thereof. In yet another embodiment, the vaccine may further comprise toxin A and toxin B, or a functional variant or fragment thereof.

The inventors realise that knowledge of the existence of these five novel spore coat proteins, and in particular, their sequences, can also be harnessed in the preparation of useful therapeutic drugs for treating, preventing or ameliorating *Clostridium* spp. or *Bacillus* spp. infections. For example, any agent which blocks the binding of the spore coat (and in particular at least one of the spore coat proteins described herein) with a target human or animal cell, can be used as a medicament to prevent or treat an infection in that target cell.

Therefore, in a thirteenth aspect, there is provided an agent capable of blocking the binding of a polypeptide selected from the group consisting of SEQ ID No:1 to 5, or a functional variant or functional fragment thereof, with a human or animal cell, for use in treating, ameliorating or preventing an infection with *Clostridium* spp. or *Bacillus* spp.

In a fourteenth aspect, there is provided a method of treating, ameliorating or preventing an infection with *Clostridium* spp. or *Bacillus* spp., the method comprising administering, to a subject in need of such treatment, an agent capable of blocking the binding of a polypeptide selected from the group consisting of SEQ ID No:1 to 5, or a functional variant or functional fragment thereof, with a human or animal cell.

Preferably, the agent is capable of treating, ameliorating or preventing an infection with *C. difficile*. The agent which is capable of blocking the binding of a polypeptide selected from the group consisting of SEQ ID No:1 to 5, or a functional variant or functional fragment thereof, with a human or animal cell may be an antibody. For example, an antibody exhibiting specificity to any of the polypeptides SEQ ID No:1-5 would be capable of blocking binding of the polypeptide with a human or animal cell. For example, *Bacillus* spores expressing the polypeptide may generate secretory IgA at the mucosal surface, and the antibody (sIgA) would block binding of *C. difficile* spores to the gut epithelium.

Furthermore, based on the surprising enzymatic activities of the spore coat proteins, the inventors believe that it will also be possible to treat a subject infected with *C. difficile* or *Bacillus* spp. by administering a compound which is capable of inhibiting the activity of any one of these enzymes.

Hence, in a fifteenth aspect, there is provided an agent capable of inhibiting the activity of a polypeptide selected from the group consisting of SEQ ID No:1 to 5, or a functional variant or functional fragment thereof, for use in treating, ameliorating or preventing an infection with *Clostridium* spp. or *Bacillus* spp.

In a sixteenth aspect, there is provided a method of treating, ameliorating or preventing an infection with *Clostridium* spp. or *Bacillus* spp., the method comprising administering, to a subject in need of such treatment, an agent capable of inhibiting the activity of a polypeptide selected from the group consisting of SEQ ID No:1 to 5, or a functional variant or functional fragment thereof.

Preferably, the agent is capable of treating, ameliorating or preventing an infection with *C. difficile*. Chitinases and peroxiredoxins (e.g. CotE) produce inflammation, which is one of the symptoms of *C. difficile* infection. The inventors believe that the disease is multifactorial, and not due only to the toxins produced by *C. difficile*. Accordingly, the agents and methods may be used to treat inflammation, pain, a hormonal imbalance and/or an intestinal disorder.

As described in Example 4, the inventors have surprisingly found that CotE is a 1-cys-peroxiredoxin-chitinase. Its homology seems to be closest to the Family 18 chitinases, which can be inhibited by methylxanthine drugs. The inventors have convincingly demonstrated that pentoxifylline, which is a methylxanthine, effectively inhibits chitinase. Accordingly, the agent which is capable of inhibiting the activity of a polypeptide selected from the group consisting of SEQ ID No:1 to 5, or a functional variant or functional fragment thereof, may be a methylxanthine. Other suitable chitinase inhibitors which can be used may include Argifin, Argadin, Chitobiose and Chitotriose thiazolines. It is preferred that a chitinase inhibitor may be used in treating inflammation caused by infection with *Clostridium* spp., preferably with *C. difficile*.

It will be appreciated that agents, vaccines and medicaments according to the invention may be used in a monotherapy (i.e. the sole use of an agent capable of inhibiting the activity of a polypeptide of the invention, or the sole use of an agent capable of blocking the binding of a polypeptide with a human or animal cell), for treating, ameliorating or preventing an infection with *Clostridium* spp. or *Bacillus* spp. Alternatively, agents, vaccines and medicaments according to the invention may be used as an adjunct to, or in combination with, known therapies for treating, ameliorating, or preventing infections with *Clostridium* spp. or *Bacillus* spp. For example, the agent may be used in combination with known agents for treating *Clostridium* spp. or *Bacillus* spp. infections. Antibiotics used for *C. difficile* include clindamycin, vancomycin, and metrodinazole. Probiotics used for *C. difficile* include Lactobacilli, and *Bifidobacteria*.

The agents, vaccines and medicaments according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given, and preferably enables delivery of the agents across the blood-brain barrier.

Medicaments comprising agents and vaccines of the invention may be used in a number of ways. For instance, oral administration may be required, in which case the agents may be contained within a composition that may, for example, be ingested orally in the form of a tablet, capsule or liquid. Compositions comprising agents, vaccines and medicaments of the invention may be administered by inhalation (e.g. intranasally). Compositions may also be formulated for topical use. For instance, creams or ointments may be applied to the skin.

Agents, vaccines and medicaments according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with agents used according to the invention is required and which would normally require frequent administration (e.g. at least daily injection).

In a preferred embodiment, agents, vaccines and medicaments according to the invention may be administered to a subject by injection into the blood stream or directly into a site requiring treatment. Injections may be intravenous (bolus or infusion) or subcutaneous (bolus or infusion), or intradermal (bolus or infusion).

It will be appreciated that the amount of the agent, vaccine or medicament that is required is determined by its biological activity and bioavailability, which in turn depends on the mode of administration, the physiochemical properties of the agent, vaccine and medicament, and whether it is being used as a monotherapy or in a combined therapy. The frequency of administration will also be influenced by the half-life of the agent within the subject being treated. Optimal dosages to be administered may be determined by those skilled in the art, and will vary with the particular agent in use, the strength of the pharmaceutical composition, the mode of administration, and the advancement of the bacterial infection. Additional factors depending on the particular subject being treated will result in a need to adjust dosages, including subject age, weight, gender, diet, and time of administration.

Generally, a daily dose of between 0.001 μg/kg of body weight and 10 mg/kg of body weight of agent or vaccine according to the invention may be used for treating, ameliorating, or preventing bacterial infection, depending upon which agent or vaccine is used. More preferably, the daily dose is between 0.01 μg/kg of body weight and 1 mg/kg of body weight, more preferably between 0.1 μg/kg and 100 μg/kg body weight, and most preferably between approximately 0.1 μg/kg and 10 μg/kg body weight.

The agent, vaccine or medicament may be administered before, during or after onset of the bacterial infection. Daily doses may be given as a single administration (e.g. a single daily injection). Alternatively, the agent, vaccine or medicament may require administration twice or more times during a day. As an example, agents, vaccines and medicaments may be administered as two (or more depending upon the severity of the bacterial infection being treated) daily doses of between 0.07 μg and 700 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of agents, vaccines and medicaments according to the invention to a patient without the need to administer repeated doses. Known procedures, such as those conventionally employed by the pharmaceutical industry (e.g. in vivo experimentation, clinical trials, etc.), may be used to form specific formulations of the agents, vaccines and medicaments according to the invention and precise therapeutic regimes (such as daily doses of the agents and the frequency of administration).

In a seventeenth aspect of the invention, there is provided a *Clostridium* spp. or *Bacillus* spp. treatment composition comprising: (i) an agent capable of blocking the binding of a polypeptide selected from the group consisting of SEQ ID No:1 to 5, or a functional variant or functional fragment thereof, with a human or animal cell; or (ii) an agent capable of inhibiting the activity of a polypeptide selected from the group consisting of SEQ ID No:1 to 5, or a functional variant or functional fragment thereof; and optionally a pharmaceutically acceptable vehicle.

The term "*Clostridium* spp. or *Bacillus* spp. treatment composition" or "anti-*Clostridium* spp. or anti-*Bacillus* spp. composition" can mean a pharmaceutical formulation used in the therapeutic amelioration, prevention or treatment of *Clostridium* spp. or *Bacillus* spp. infections in a subject.

The invention also provides in an eighteenth aspect, a process for making the composition according to the seventeenth aspect, the process comprising combining a therapeutically effective amount of: (i) an agent capable of blocking the binding of a polypeptide selected from the group consisting of SEQ ID No:1 to 5, or a functional variant or functional fragment thereof, with a human or animal cell; or (ii) an agent capable of inhibiting the activity of a polypeptide selected from the group consisting of SEQ ID No:1 to 5, or a functional variant or functional fragment thereof; with a pharmaceutically acceptable vehicle.

The agent, which is capable of blocking the binding of a polypeptide selected from the group consisting of SEQ ID No:1 to 5, or a functional variant or functional fragment thereof, with a human or animal cell, may be an antibody. The agent, which is capable of inhibiting the activity of a polypeptide selected from the group consisting of SEQ ID No:1 to 5, or a functional variant or functional fragment thereof, may be a methylxanthine, such as pentoxifylline.

A "subject" may be a vertebrate, mammal, or domestic animal. Hence, medicaments according to the invention may be used to treat any mammal, for example livestock (e.g. a horse), pets, or may be used in other veterinary applications. Most preferably, the subject is a human being.

A "therapeutically effective amount" of agent is any amount which, when administered to a subject, is the amount of drug that is needed to treat the infection, or produce the desired effect.

For example, the therapeutically effective amount of agent used may be from about 0.001 ng to about 1 mg, and preferably from about 0.01 ng to about 100 ng. It is preferred that the amount of agent is an amount from about 0.1 ng to about 10 ng, and most preferably from about 0.5 ng to about 5 ng.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The agent may be prepared as a sterile solid composition that may be dissolved or suspended at the time of administration using sterile water, saline, or other appropriate sterile injectable medium.

The agents and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The agents used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/nucleotide/peptide sequence", "functional variant" and "functional fragment", can be a sequence that has at least 40% sequence identity with the amino acid/nucleotide/peptide sequences of any one of the sequences referred to herein, for example 40% identity with the sequence identified as SEQ ID No:1 (i.e. CotA protein) or the nucleotide identified as SEQ ID No:6 (i.e. CotA gene), or 40% identity with the polypeptide identified as SEQ ID No:2 (i.e. CotB protein) or the nucleotide identified as SEQ ID No:7 (i.e. CotB gene), and so on.

Amino acid/polynucleotide/polypeptide sequences with a sequence identity which is greater than 50%, more preferably greater than 65%, 70%, 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90%, 92%, 95%, 97%, 98%, and most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:— Sequence Identity=(N/T)*100.

Alternative methods for identifying similar sequences will be known to those skilled in the art. For example, a substantially similar nucleotide sequence will be encoded by a sequence which hybridizes to the sequences shown in SEQ ID No's: 6-10 or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in SEQ ID No: 1-5.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawings, in which:—

FIG. 1 shows the sporulation of *C. difficile* on solid medium. *C. difficile* 630 was grown on agar at 37° C. Each day samples were removed and examined for the number of spores by either phase contrast microscopy using a haemocytometer to count phase bright spores and vegetative cells, or, by heating the spore suspension for 60° C. for 20 min and plating for CFU/ml with comparison to untreated CFU/ml;

FIG. 2 shows the ultrastructure of *C. difficile* 630 spores and extracted coat proteins. Panel A shows a typical image of a 7-day old mature spore of CD630. The partially removed electron dense outer exosporia) layer (Ex) is apparent as well as the core, CR; germ cell wall, GCW; cortex, CX; inner coat, IC; and outer coat, OC. The scale bar indicates 100 nm. Panel B shows proteins extracted using a sodium borate-SDS-DTT extraction buffer from 7-day old spore coats of CD630 spores grown on solid agar. Proteins were fractionated by SDS-PAGE (12.5%) and samples loaded as dilutions, lane 1, no dilution; lane 2, ½ dilution; lane 3, ¼ dilution; lane 4,⅛ dilution. M, markers. Alongside the gel the identities of the bands excised and analysed by mass spectrometry are shown. Partially truncated proteins (Δ) are indicated. Panel C shows the chromosomal positions of the genes described herein;

FIG. 3 shows orthologues of *C. difficile* 630 spore surface proteins CotA-E in other spore formers. The table shows possible orthologues of CotA-E found in *Geobacillus kaustophilus* and *Oceanobacillus iheyensis* as well as other common *Clostridium* and *Bacillus* spore formers. For CotE also shown are orthologues to the individual peroxiredoxin and chitinase domains. Hypothetical proteins are also included. Orthologues were identified through BLASTP searches (www.ncbi.nih.gov) using protein sequences against the following genomes: B.a., *Bacillus anthracis* Sterne; B.c., *Bacillus cereus* ATCC 10987; B.cl., *B. clausii* KSM-K16; B.h., *B. halodurans* C-125; B.l., *B. licheniformis* ATCC 14580; B.s., *B. subtilis* 168; B.t., *B. thuringiensis* serovar *konkkukian* str. 97-27; C.a., *Clostridium acetobutylicum* ATCC 824; C.c., *C. cellulolyticum* H10; C.d., *C. difficile* 630; C.n., *C. novyi* NT; C.p., *C. perfringens* ATCC 13124; C.t., *C. tetani* E88 (asporpgeneous); C.th., *C. thermocellum* ATCC 27405; G.k., *Geobacillus kaustophilus* HTA426; O.i., *Oceanobacillus iheyensis* HTE831;

FIG. 4 shows CotCB and CotD. Panel A shows the entire CotCB polypeptide and its similarity with the manganese catalases (a family of ferritin-like diron enzymes). Residues involved in forming the dimanganese centre are indicated (*). Panel B shows the homology of CotD with the ferritin-like family of catalases and amino acids involved in forming the dinuclear metal binding motif (*). Panel C shows the amino acid sequence homology between CotCB and CotD which share consensus and identity positions at 80.6% and 70.2%, respectively;

FIG. 5 shows the entire CotE polypeptide and its amino-terminal 1-cys-peroxiredoxin and carboxy-terminal chitinase domains. Active site residues are indicated;

FIG. 6 shows surface display of CotA, CotB, CotCB, CotD and CotE using confocal imaging of suspensions of CD630 spores labeled with mouse serum (1:1000 dilution) raised against each of the five Cot proteins. CD630 spores labeled with pre-immune serum served as a control and showed no labelling. Spores labelled with anti-spore serum are also shown ('Spores'). Anti-mouse IgG-TRITC conjugate was used for secondary labelling. Images were taken using a Nikon Eclipse fluorescence microscope equipped with a Bio-Rad Radiance 2100 laser scanning system. (Image size=37×37 μm);

FIG. 7 shows immunoanalysis of spore coats. Panel A. Spore coats of CD630 were extracted and separate lanes probed with polyclonal (mouse) antibodies to CotA-E. Molecular weights of the relevant bands are shown. For CotE two principal bands of 81 and 40 kDa were found. Serum from unimmunized mice did not react with *C. difficile* spore coat proteins. Panel B. Purified recombinant CotCB and CotD proteins (2 μg) were fractionated on SDS-PAGE gels and probed with either CotCB or CotD antibodies at 1/1500 and 1/3000 dilutions, respectively. Positions of CotCB (25 kDa) and CotD (23 kDa) bands are indicated. Panel C. Coat proteins extracted from spores of CD630, *B. subtilis* PY79 and *B. clausii* O/C were fractionated and probed with antiserum to formalin-inactivated CD630 spores. Positions of CotA-E are shown. Panel D. As panel C but proteins were probed with antiserum to formalin inactivated *B. subtilis* PY79 spores;

FIG. 8 shows the removal of Cot proteins using sonication. Panel A. *C. difficile* spores were sonicated (30 sec cycles), 2-times, 5-times and 10-times and pellets and supernatants solubilised in SDS-PAGE loading buffer and fractionated by SDS-PAGE (12.5%). Panel B. Spores were sonicated and pellet and supernatant fractions were probed with antiserum to each of the five Cot proteins. Molecular weights of Cot proteins are shown. For both panels UT, untreated spores. M, markers;

FIG. 9 shows the enzymatic activities of *C. difficile* 630 spores. Panel A, catalase activity in CD630 and *B. subtilis* spores or vegetative cells. Panel B, catalase activity of CD630 spores at different stages of maturation on solid agar. Panel C, inhibition of catalase activity by sodium azide. Panel D, peroxiredoxin activity of CD630 spores and vegetative cells and *S. mutans* cells. Panel E, peroxiredoxin activity of CD630 spores at different stages of maturation on solid agar. Panel F, chitinase activity in CD630 spores and vegetative cells of CD630 and *B. licheniformis*. Panel G, chitinase activity of CD630 spores at different stages of maturation on solid agar. Panel H, germination of CD630 spores in sodium taurocholate solutions. Panel I, chitinase activity in response to spore germination using 3% or 5% sodium taurocholate solutions. Panel J, chitinase activity obtained in cell pellet and supernatant fractions of CD630 spores following incubation with 0% and 3% sodium taurocholate for 30 min. Panel K, chitinase activity of CD630 spores in response to sonication (30 sec. cycles). Panel L, chitinase activity obtained in cell pellet and supernatant fractions of CD630 spores following sonication (30 sec. cycles);

FIG. 10 shows a map of the plasmid, pDG364, used for cloning and expressing the various *C. difficile* proteins (i.e. antigens) in *B. subtilis*. The map shows the multiple cloning site, cat (chloramphenicol resistance) gene and front and rear portions of the amyE gene. Restriction sites that can be used for linearisation are indicated; nucleotide positions are noted in brackets;

Figure 20:
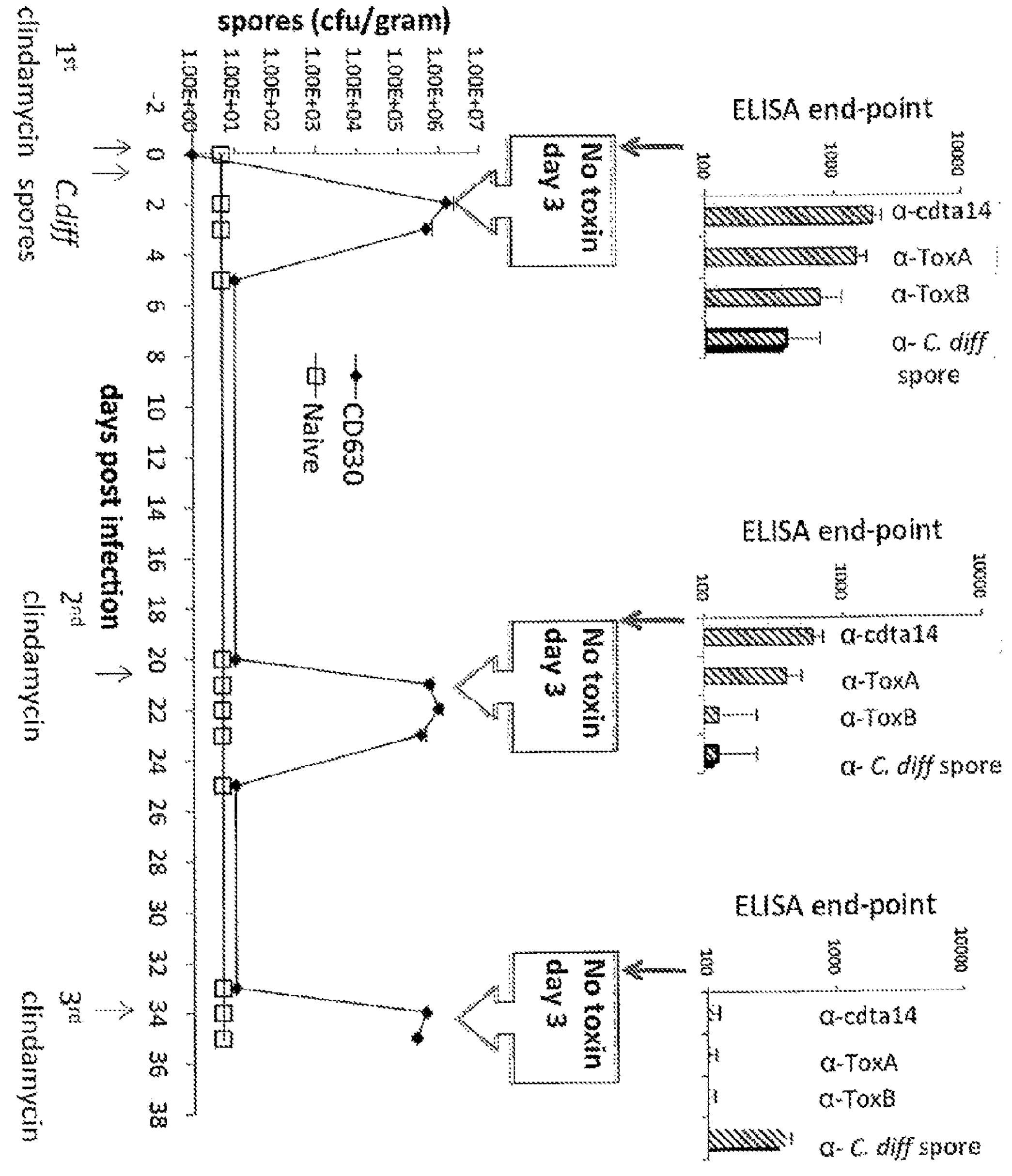
Figure 21:
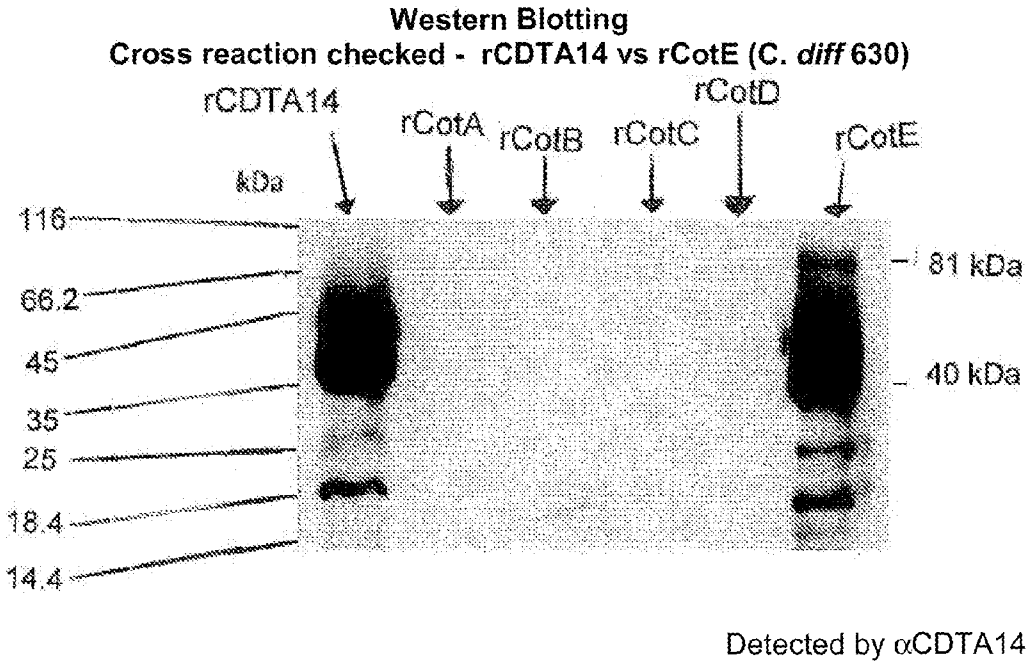
Figure 22:
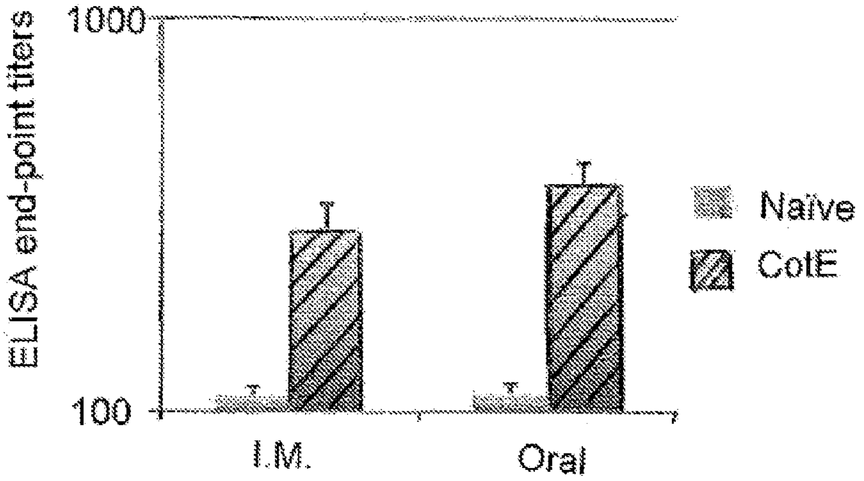
Figure 23:
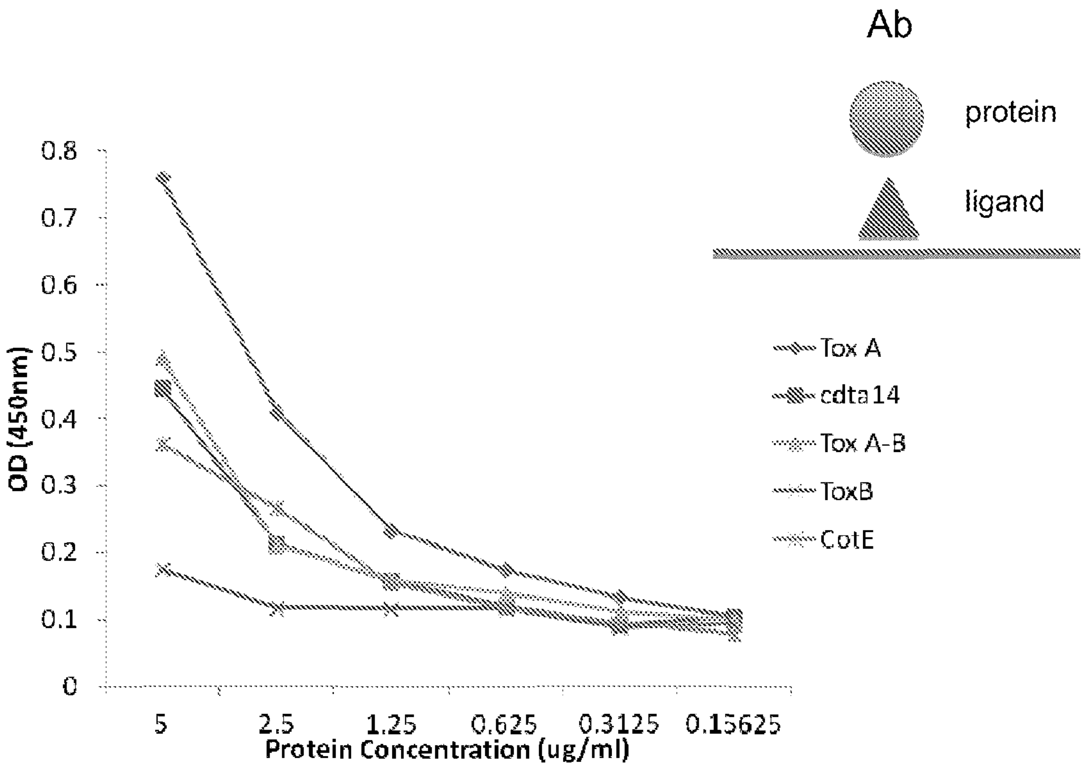
Figure 25:
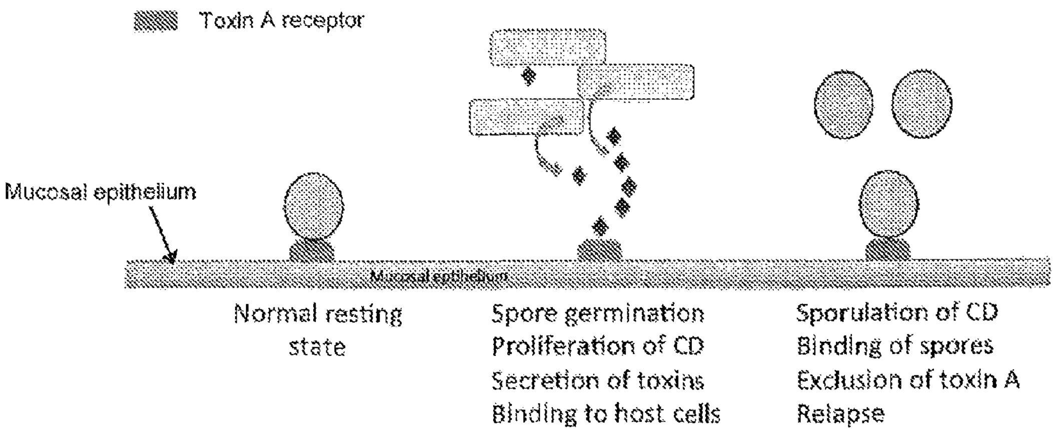

FIG. 20 shows data from hamsters with PP108 spores (dosed on days 1, 14, 35 and 57 with $5\times10^{10}$ spores/dose of PP108) and induced *C. difficile* with clindamycin treatment+oral dosing with 100 CD630 spores as described in (28);

FIG. 21 shows the results of Western blotting using antibodies to the C-terminus of toxin A (CDTA) against purified recombinant proteins from the *C. difficile* spore coat. These recombinant proteins have been reported elsewhere (29);

FIG. 22 shows the results of hamsters immunized orally using PP108 spores (expressing CDTA and as described in FIG. 20) or by intra-muscular injection with CDTA (10 μg, days 0, 7, 28);

FIG. 23 shows the results of Ligand Binding studies. A synthetic ligand Galα1-3Galβ1-4GlcNAc-HSA that is the toxin A receptor-binding site was used in a capture ELISA assay. Ligand (2.5 μg/ml; Dextra Labs Ltd; NGP2334) was bound to ELISA plates in 0.01M PBS (pH 7.4) and pure proteins (50 μg/ml) added of CDTA, toxin A, toxin B, toxins A+B, and CotE. Secondary antibodies were used to detect and quantify adsorption;

FIG. 24 shows results of mucosal responses in which the levels of IgG and IgA in faeces was determined using mucosal IgG and IgA specific to toxin A and toxin B;

FIG. 25 shows a model for Relapse and Remission; and

Figure 26:
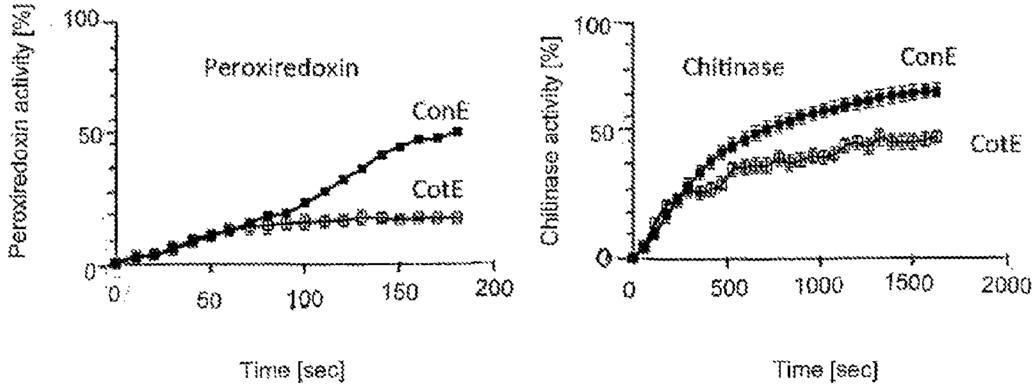

FIG. 26 (panel D) shows peroxiredoxin activity for CotE and a control enzyme (ConE), and panel E shows chitinase activity for CotE and a control enzyme (ConE).

EXAMPLE 1

Materials and Methods

General Methods and Strains

Methods for the preparation of *Bacillus* spores are described in (1). *C. difficile* 630 is a pathogenic bacterial strain and produces ($tcdA^+$ $tcdB^+$) and was obtained from Neil Fairweather (Imperial College, UK). CD630 was routinely grown in vegetative culture by overnight growth (10 ml) at 37° C. in TGY-vegetative medium (3% tryptic soy broth, 2% glucose, 1% yeast extract, 0.1% L-cysteine) (2). *S. mutans* GB1 was obtained from Phan Nghia (Hanoi Univ., Vietnam); *B. subtilis* strain PY79 is a prototrophic ($Spo^+$) laboratory strain and a lab stock as was *B. clausii* O/C. *B. licheniformis* strain HU14 was obtained from the *Bacillus* Genetic Stock Center (Ohio, USA).

Sporulation of *C. difficile*

All manipulations were made in an anaerobic incubator (Don Whitley, UK). A single bacterial colony was grown on BHIS (brain heart infusion supplemented with L-cysteine, 0.1% and yeast extract, 5 mg/ml; (3) agar overnight at 37° C. One fresh single colony from the BHIS plate was inoculated in 10 ml of TGY medium (3% tryptic soy broth; 2% glucose; 1% yeast extract; 0.1% L-cysteine) (2) and incubated at 37° C. overnight. 1 ml of TGY culture was then sub-cultured into SMC broth (90 g, peptone; 5 g, proteose peptone; 1 g, $(NH_4)_2SO_4$; 1.5 g, Tris) containing 0.1% L-cysteine (modified from Wilson et al. (*J Clin Microbiol* 15: 443-446) incubated overnight and then plated onto SMC agar. After 7 days incubation at 37° C. sporulation was confirmed by phase-contrast microscopy and spore crops harvested.

Spore Purification

The methods used were modified from Lawley et al (4). Spores were washed twice in water and then suspended in PBS containing 125 mM Tris, 200 mM EDTA, 0.3 mg/ml proteinase K (E00492; Fermentas) and 1% sarcosyl and incubated with gentle shaking at 37° C. for 2 h. Spores were centrifuged (8000 rpm, 10 min) and pellets resuspended in water and washed a further 10 times. After the final suspension in water, spores were heat-treated (60° C., 20 min) to kill any residual cells; aliquots were stored at 4° C. until use. To calculate the spore, CFU aliquots were serially diluted in PBS and plated onto BHIS agar supplemented with 0.1% sodium taurocholate (Sigma, UK). Plates were incubated for 24-48 h before CFU were enumerated.

Spore Coat Extractions

The spore coat extraction procedure has been described in (5) but in brief spores ($2\times10^9$) were suspended in freshly prepared 100 μl of sodium borate-SDS-DTT buffer consisting of sodium borate (0.1M, pH 10), 0.5% sodium dodecyl sulfate (SDS) and 50 mM dithiothreitol (DTT), and then incubated at 68° C. for 75 min with gentle agitation. After centrifugation (8000 rpm for 15 min) the supernatant was removed, mixed with 4×SDS-PAGE loading buffer and fractionated by SDS-PAGE. For *B. subtilis* and *B. clausii* spores, coat proteins were extracted using the SDS-DTT buffer described in (1).

Peptide Fingerprinting

Spore coat proteins were fractionated on 12.5% SDS-PAGE mini-gels and bands excised and digested with trypsin before analysis by MALDI mass spectrometry. Digestions and analysis were conducted by the University of Cambridge Protein & Nucleic Acid Chemistry Facility (PNAC) (http://www.bioc.cam.ac.uk/pnac).

Antibody Production pET28b expression vectors that express the complete cotA, cotB, cotCB and cotD ORFs were constructed by amplifying the respective DNA by PCR from *C. difficile* 630 chromosomal DNA and ligating to cleaved pET28b. For cotE it proved impossible to clone the entire ORF and so a fragment encoding the N-terminal, peroxiredoxin domain was cloned instead. Primers used for construction of pET28b clones are shown below in Table 1. pET28b expression vectors that express the cot gene ORFs were constructed by amplifying the respective DNA by PCR from *C. difficile* 630 chromosomal DNA and ligating to cleaved pET28b using the forward and reverse primers shown above.

TABLE 1

PCR primers used for constructing pET28b clones

| Primer | Direction | Sequence[1] | Restriction site |
|---|---|---|---|
| *cotA* | | | |
| CotA-NcoI-F | forward | GAT*CCATGG*CTGTGGAAAATAATAAATG (SEQ ID No: 11) | NcoI |
| CotA-XhoI-R | reverse | ATC*CTCGAG*TGCAATATAATCTATAGAATCTACACATAC (SEQ ID No: 12) | XhoI |
| *cotB* | | | |
| CotB-NcoI-F | forward | GAT*CCATGG*CTATAGATAATCAAAAATATG (SEQ ID No: 13) | NcoI |
| CotB-XhoI-R | reverse | ATC*CTCGAG*CATGTTTTTATAACTCTC (SEQ ID No: 14) | XhoI |
| *cotCB* | | | |
| CotCB-NcoI-F | forward | GAT*CCATGG*CTTGGATTTATCAAAAAAC (SEQ ID No: 15) | NcoI |
| CotCB-XhoI-R | reverse | ATC*CTCGAG*AAACTGATGCTTGCACTC (SEQ ID No: 16) | XhoI |
| *cotD* | | | |
| CotD-NcoI-F | forward | GAT*CCATGG*CTTGGATATATCAGAAAAC (SEQ ID No: 17) | NcoI |
| CotD-XhoI-R | reverse | ATC*CTCGAG*GAACTTTTTTGAGATTC (SEQ ID No: 18) | XhoI |
| *cotEΔ* | | | |
| CotEC-NcoI-F | forward | GAT*CCATGG*CTCCAATTGTAGCAG (SEQ ID No: 19) | NcoI |
| CotEC-XhoI-R | reverse | ATC*CTCGAG*GAATTGCCCATAAATAC (SEQ ID No: 20) | XhoI |

[1] 5'-3', restriction site is in italics

High levels of expression were obtained upon IPTG induction and purification of proteins by passage of the cell lysate through a HiTrap chelating HP column on a Pharmacia AKTA liquid chromatography system. Polyclonal antibodies were raised in mice immunized by the intra-peritoneal route with 2 μg of purified recombinant proteins on days 1, 14 and 28. Anti-spore antibodies were made by treating spores in 2% formalin (2% v/v formaldehyde in PBS) overnight at 4° C. Spores were washed 5-times with PBS and used to dose mice ($2 \times 10^8$ spores/dose) mice on days 1 and 14.

Confocal Microscopy

Spores were labeled with mouse anti-Cot serum (1:1000 dilution) followed by an anti-mouse IgG-TRITC conjugate. Images were taken using a Nikon Eclipse fluorescence microscope equipped with a BioRad Radiance 2100 laser scanning system.

Transmission Electron Microscopy (TEM)

TEM methodology using suspensions of purified CD630 spores (7-day old) were as described previously for *B. subtilis* spores (6).

Catalase Assay

The assay was performed as described elsewhere (7). Spores or vegetative cells ($1 \times 10^7$ CFU) were pelleted and resuspended in 60 μl of 50 mM potassium phosphate buffer (pH 7.0). $H_2O_2$ (1.94 ml) was added to start the reaction at RT. Samples were centrifuged and the $OD_{405}$ of supernatants measured immediately.

Peroxiredoxin Assay

The peroxiredoxin assay was as described elsewhere (8, 9). Spores or vegetative cells ($1 \times 10^8$) were pelleted by centrifugation and suspended in a reaction buffer that included $H_2O_2$. Reactions were made at 37° C. and after 15 min. cells pelleted and the $OD_{340}$ of supernatants measured.

Chitinase Assay

Chitinase was determined using a pre-supplied kit (Sigma CS0980) using spore or cell suspensions ($1 \times 10^8$ CFU/assay) in water. 4-Nitrophenyl N-acetyl-β-D-glucosaminide (1 mg/ml) was used as substrate and after the reaction was stopped (200 μl of 0.04 g/ml sodium carbonate) the suspension was centrifuged and the $OD_{405}$ of supernatants measured. Reaction time was 3 h at 37° C. The assay was also performed on spores that had been pre-germinated or following sonication. For germination, $1 \times 10^8$ spores were suspended in 100 μl of 0%, 3% and 5% sodium taurocholate in PBS (pH 7.4) for 30 min at 37° C. after which chitinase activity was determined. For sonication, $1 \times 10^8$ spores were suspended in 100 μl PBS (pH 7.4). The solution was sonicated for 2 or 7 times (10% amplitude, 30 sec) after which the assay was performed.

Results

*C. difficile* Spore Formation

Figure 1:
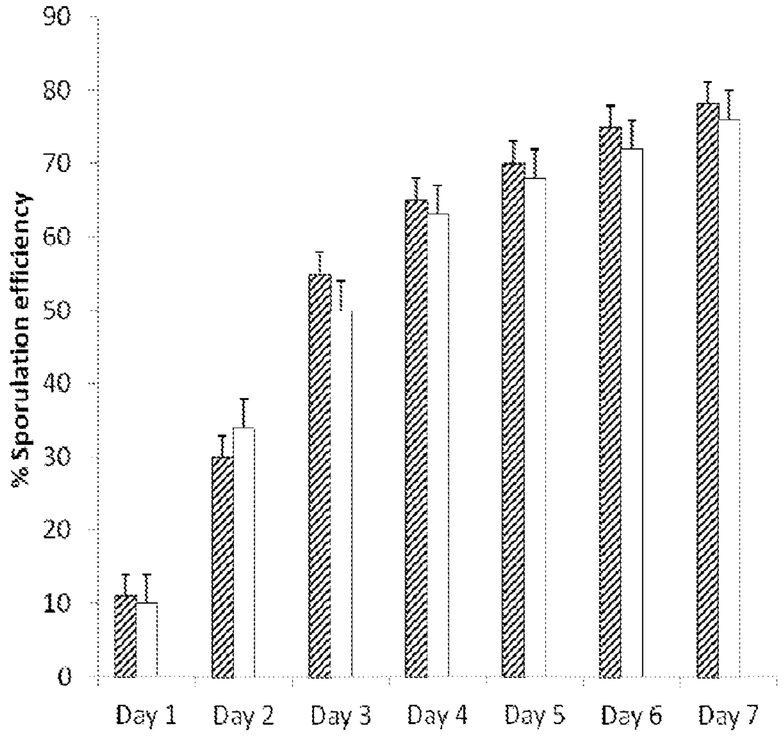

Using an empirical approach, the inventors adapted existing methods (10) to generate high levels of spore formation on a solid medium using *C. difficile* strain 630 (tcdA⁺ tedB⁺) which is referred to hereafter as CD630. After seven days of growth on agar, the inventors routinely obtained >75% sporulation, as shown in FIG. 1, with crops consisting of mature, released, spores, which were then purified further providing suspensions devoid of vegetative cells.

Figure 2A:
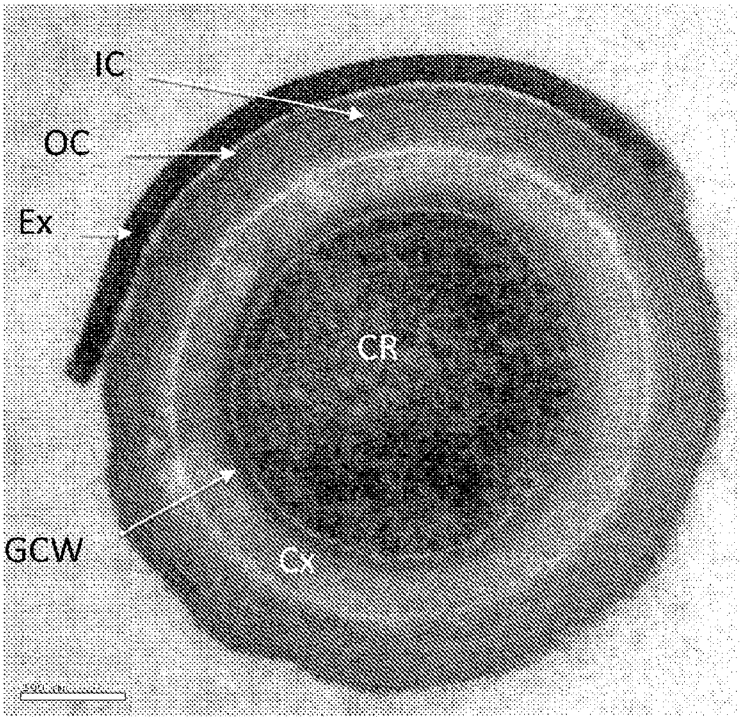

Referring to FIG. 2A, TEM analysis of spores revealed a structure common to those produced by the majority of Gram-positive spore formers (11), namely an inner core surrounded by a layer or primordial germ cell wall (peptidoglycan derived from vegetative cell walls) and a thick cortical layer (loosely cross-linked peptidoglycan specific to the spore). Three additional layers could be defined, a thick lamelated layer lying above the cortex and resembling the striated inner coat of *Bacillus* spores (11). A thinner layer that resembles the outer coat of many spore species, and finally, a thick electron dense layer that in most of the spores that were examined was partially or completely detached from the spore outer coat, as shown in FIG. 2A, and labelled Ex).

This feature is often found with spores of many species (but not *B. subtilis*) that carry an exosporium, a loose fitting sac-like structure enveloping the mature spore (11). Indeed, in a similar study conducted recently, an electron-dense exosporial layer is dearly visible encasing mature CD630 spores (4). Based on appearance and comparison with other studies, the inventors believe that this outer coat layer to be the exosporium. Their analysis showed the exosporial layer to be more intimately attached to the spore than in earlier work and believe that this might have arisen from the method of sporulation used here (solid medium vs. liquid medium as used in (4)).

Identification of *C. difficile* Spore Coat Proteins

Figure 2B:
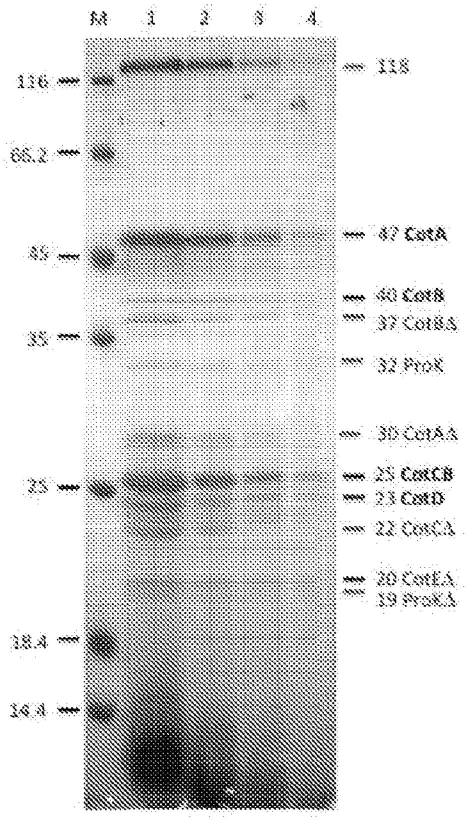

Spore coat proteins were extracted from CD630 using a sodium borate-SDS-DTT buffer and fractionated by SDS-PAGE, as shown in FIG. 2B. Eleven protein bands were excised from Coomassie-stained gels and subjected to peptide mass fingerprinting using trypsin digestion and MALDI mass spectrometry. This analysis revealed that a number of protein bands corresponded to truncated, breakdown, products, as summarised in Table 2.

TABLE 2

SDS-PAGE and MALDI peptide fingerprint analysis of *C. difficile* 630 spore coat proteins

| Fragment Mwt. | Protein ID[a] | Coding sequence No[b] | Predicted mwt | Assigned Gene |
|---|---|---|---|---|
| 118 | ND | — | — | — |
| 47 | Hypothetical protein | CD1613 | 34 | cotA |
| 40 | Hypothetical protein | CD1511 | 35 | cotB |
| 37 | Hypothetical protein | CD1511 | 35 | cotB |
| 32 | Proteinase K (contaminant from purification steps) | — | — | — |
| 30 | Hypothetical protein | CD1613 | 34 | cotA |
| 25 | Putative spore-coat protein; Manganese catalase; similar to CotJC of *B. subtilis.* | CD0598 | 21 | cotCB |
| 23 | Putative spore-coat protein; Manganese catalase; similar to CotJC of *B. subtilis.* | CD2401 | 21 | cotD |
| 22 | Putative spore-coat protein; Manganese catalase; similar to CotJC of *B. subtilis.* | CD0598 | 21 | cotCB |
| 20 | Putative bifunctional protein: peroxiredoxin/chitinase | CD1433 | 81 | cotE |
| 19 | Proteinase K (contaminant from purification steps) | — | — | — |

[a]based on peptide mass fingerprinting of tryptic digestions ND, no determination.
[b]coding sequences as described in (12).

Figure 2C:
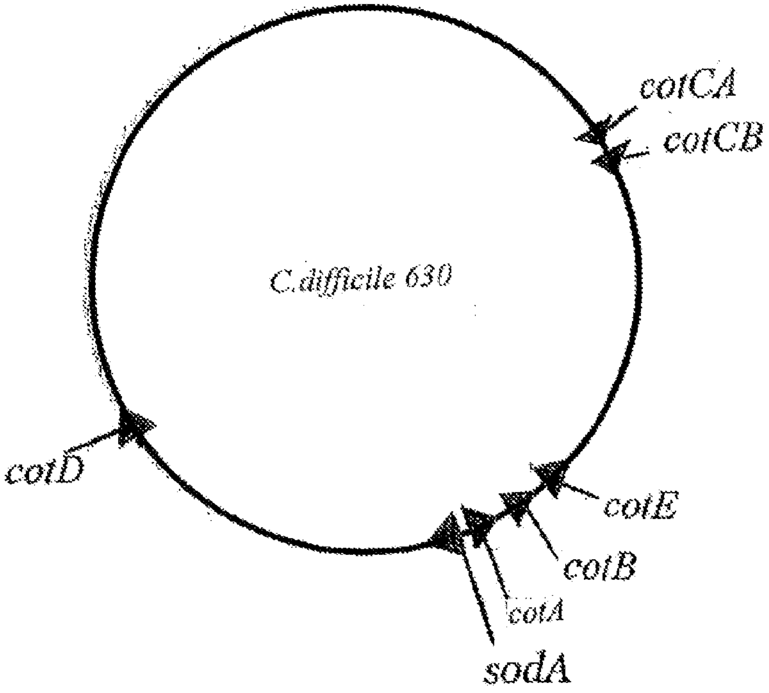

One high molecular weight species of 118 kDa could not be identified and was thought to possibly be an aggregate. Two further bands, were chain E of proteinase K, which was a contaminant derived from the spore purification process. The remaining eight protein species corresponded to five different proteins which are referred to herein as CotA, CotB, CotCB, CotD and CotE and their genes as cotA-cotE (see FIG. 2C) based on nomenclature used in *B. subtilis* (11).

The amino acid sequences of CotA, CotB, CotCB, CotD and CotE are described herein as SEQ ID No's: 1-5.

The nucleic acid sequences encoding CotA, CotB, CotCB, CotD and CotE are described herein as SEQ ID No's: 6-10.

The orthologues are shown in FIG. 3. CotA shares no homology with other proteins in existing databases but CotB is believed to carry unidentified orthologues in a number of *Bacilli* and *Clostridia*. CotCB and CotD are homologous with each other (70% conserved residues) and to manganese catalases including the CotJC inner spore coat protein (and catalase) found in *B. subtilis* (see FIG. 4). As will be discussed later, the 25 kDa protein is most probably encoded by the second cistron of an operon, and so the inventors refer to the gene and protein as cotCB and CotCB, respectively. CotE, based on its amino acid sequence, corresponds to a novel bifunctional protein with amino-terminal peroxiredoxin (1-cys peroxiredoxin) and carboxy-terminal manganese chitinase activity (see FIG. 5). The predicted molecular weight of this protein was 81 kDa although the full-length protein was not dearly discernable in our SDS-PAGE fractionations. CotE also carries orthologues in a number of spore formers (see FIG. 3). As a single bifunctional protein, no orthologues were found in other *Bacilli* or *Clostridia* but matches were found to either the peroxiredoxin or chitinase domains carried in CotE. This includes a putative peroxiredoxin YkuU in *B. subtilis* (BS938810) and a number of putative chitinases from exosporium-containing species including *Bacillus anthracis, B. cereus, Bacillus thuringiensis, Bacillus clausii* and *Bacillus halodurans* (see FIG. 3).

Immuno-Analysis of Spore Coat Proteins

Figure 6:
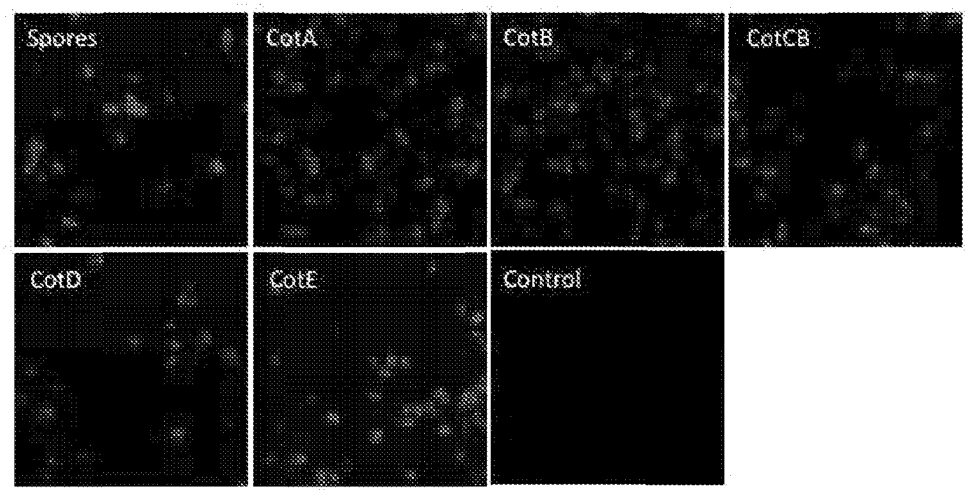

Polyclonal antibodies to recombinant Cot proteins were raised in mice. In the case of CotE, the inventors used the amino-terminal, peroxiredoxin domain, of CotE to generate antibodies. Using confocal imaging of antibody-labelled *C. difficile* spores, they observed surface decoration using all antisera (see FIG. 6) while unimmunized serum gave no labeling. This demonstrated that, surprisingly, each of the five coat proteins must be surface-exposed on the mature spore.

Figure 7:
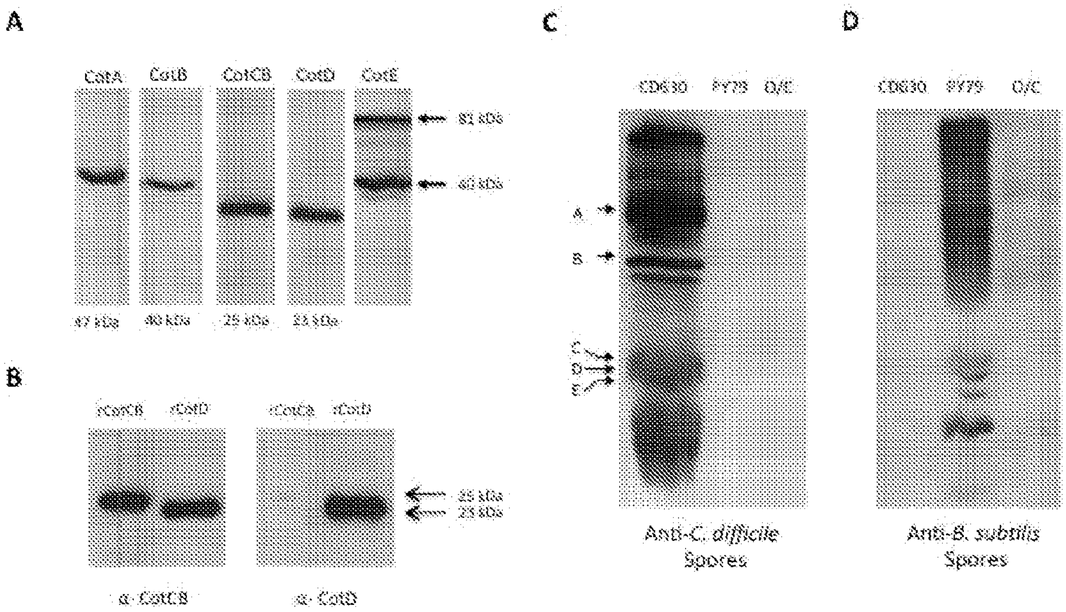

These antibodies were used in a Western blot to probe spore coat protein extractions (see FIG. 7A). CotA, CotB and CotD were present as single bands of 47, 40 and 23 kDa respectively corresponding to the predicted molecular weights of each of these proteins. CotE antisera identified two strongly reacting bands of 81 and 40 kDa. For CotCB, when probed with anti-CotCB, the inventors could sometimes discern two bands of 25 and 23 kDa although this is not apparent in FIG. 7A. Since CotCB and CotD were homologous, the inventors wondered whether these proteins shared related epitopes. Using recombinant proteins (rCotCB and rCotD), they probed each with anti-CotCB and anti-CotD sera. As shown in FIG. 7B, CotCB was recognised by both anti-CotCB and anti-CotD sera. On the other hand, anti-CotD antibodies were able to bind to CotD but exhibited very weak binding to CotCB.

Using antisera raised against formalin-inactivated CD630 spores, spore coat proteins extracted from CD630, *B. subtilis* and *B. clausii* were then probed (see FIG. 7C). *C. difficile* serum showed no cross-reaction against either *B. subtilis* or *B. clausii* spore coat proteins, the latter of which carries an exosporium. Similarly, antiserum raised against formalin-inactivated *B. subtilis* spores showed no reaction against CD630 spores but some cross-reaction to *B. clausii* (see FIG. 7D). These results support bioinformatic analysis that has shown little conservation between *C. difficile* and *B. subtilis* spores (4, 12).

A Potential Location in the Spore Exosporium

Figure 8:
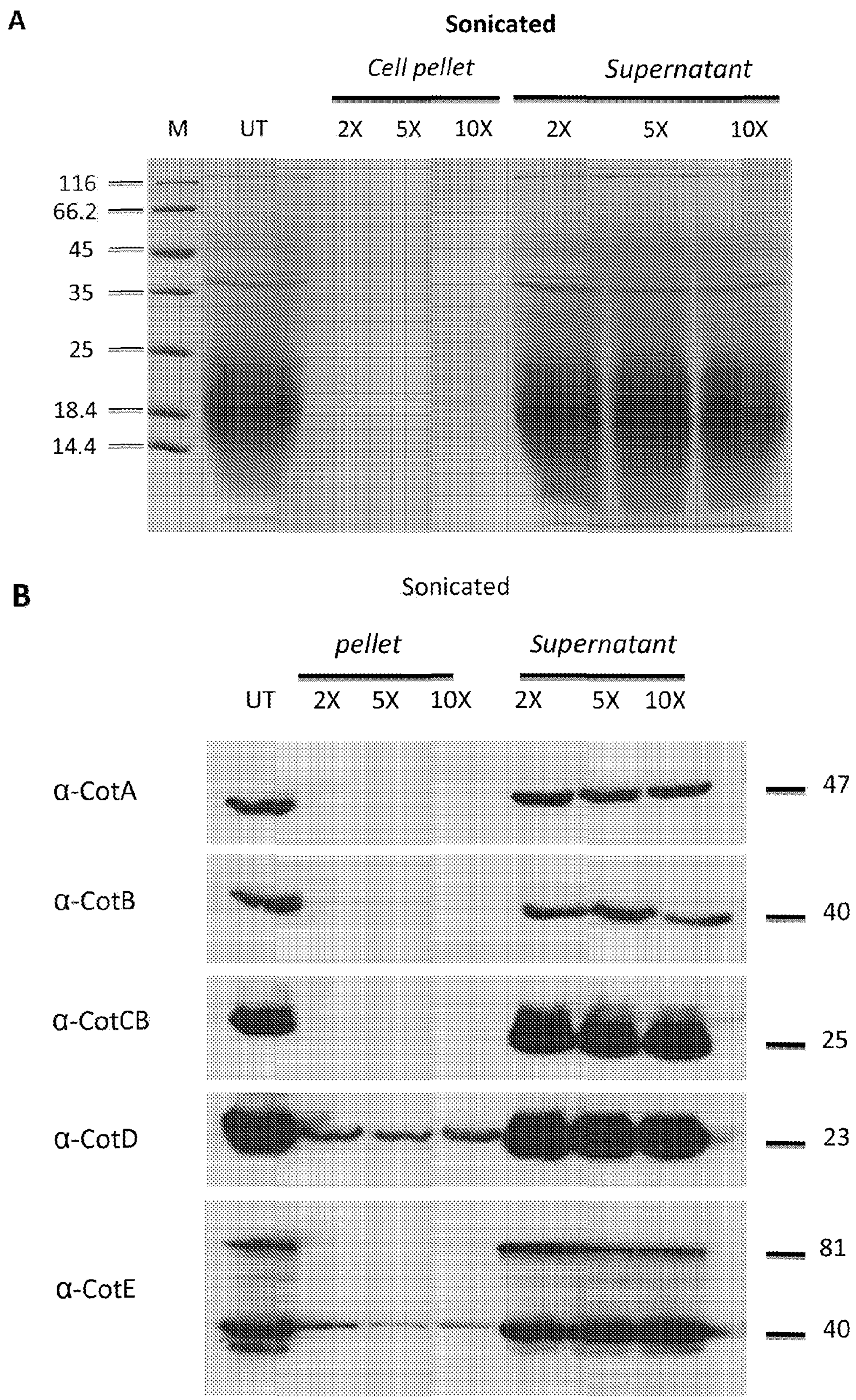

In other spore formers, the exosporium can be removed by sonication (13). Accordingly, the inventors subjected CD630 spores to repeated cycles of sonication. Spore pellets and supernatants were then solubilised with sodium borate-SDS-DTT extraction buffer and fractionated on 12.5% SDS-PAGE gels (see FIG. 8A). The results showed that as few as two cycles of sonication were sufficient to remove almost the entire component of sodium borate solubilised proteins all of which were found in the supernatant fraction. Examination of the sonicated spores by phase-contrast microscopy revealed that phase-bright spores remained intact and analysis of CFU before and after sonication demonstrated no change in viability. The spore pellet and supernatant fractions were probed with antiserum to CotA-E (see FIG. 8B). CotA, CotB and CotCB were not detectable in the spore pellets and found only in the supernatant fractions. CotD and CotE although not visibly apparent in Coomassie-stained gels were present in both the spore pellet and supernatant fractions using immunoanalysis. If CotD is still present in the spore coat fraction then, it is interesting to consider why it was not detected using anti-CotCB serum since CotCB and CotD share related epitopes. The inventors postulate that although the recombinant proteins, at high concentration, could be detected, this does not reflect the composition and abundance of CotCB and CotD in the spore coat. In the case of CotE, only the 40 kDa CotE fragment was found in the spore pellet fraction. The apparent ease with which the spore coat proteins were removed from the spore by sonication suggests that all five Cot proteins are located in the exosporial layer.

Enzymatic Properties of Spores

Based on the amino acid sequences of CotCB, CotD and CotE and their surface location, the inventors predicted that spores could carry enzymatic activity, either latent or active. Accordingly, in order to test this, they conducted a number of assays. To their surprise, they found that spores do have catalase, peroxiredoxin and chitinase activities. In each case, the inventors used suspensions of purified spores that had been checked microscopically to confirm greater than 99.99% free spores. Catalase activity was determined (see FIG. 9A) using a photometric assay of $H_2O_2$ breakdown using suspensions of CD630 spores, vegetative cells and as useful comparators, spores and vegetative cells of *B. subtilis*. CD630 spores had noticeable catalase activity, while vegetative cells were completely negative. By comparison, *B. subtilis* spores were catalase negative and vegetative cells positive. The inventors next focused on CD630 spores and heated spores at different temperatures for 20 minutes, allowed the spore suspension to return to ambient and then conducted the catalase assay. They found that heating at 50° C. had no effect on enzyme activity but at 60° C., enzyme activity was reduced by 40%, and at 70° C., it was reduced by 60%. The maturity of spores are believed to affect spore-associated enzyme activity since, in other spore formers, notably *B. subtilis*, the spore coat physically changes over time with the spore coat shrinking and forming distinctive surface corrugations. Spore suspensions were assessed for catalase activity at 1-day intervals post-purification and the inventors observed a marked decline in enzymatic activity after just 1 day of maturation (see FIG. 9B).

Since the substrate for catalase activity, $H_2O_2$, was the same as that used in the peroxiredoxin assay, the inventors measured the effect of sodium azide on catalase activity since catalase is sensitive to sodium azide, while peroredoxin activity is not (14). Using increasing concentrations of sodium azide, catalase activity of CD630 spores was inhibited demonstrating that they were measuring spore-associated catalase and not that of peroxiredoxin (see FIG. 9C).

Peroxiredoxin activity was then assessed using CD630 spores and vegetative cells together with a suspension of *S. mutans* cells that are known to produce this enzyme (15). CD630 vegetative cells carried barely detectable levels of activity while spores dearly were positive and had levels of activity equivalent to that of *S. mutans* (see FIG. 9D). Peroxiredoxin activity exhibited a marked decline (60%) when spores were heated above 60° C., and at 80° C. activity was abolished. The effects of spore maturity was also assessed with activity gradually declining over time with 7-day-old spores losing 48% of the activity exhibited in 1-day-old preparations (see FIG. 9E). Peroxiredoxin activity of 1-day-old spores was measured in the presence of 0.5, 1 and 2 mM sodium azide and no decline in activity was observed indicating that activity was that of peroxiredoxin and not due to catalase.

Chitinase activity of CD630 spores and vegetative cells was assessed using vegetative cells of chitinase-producing cells of *B. licheniformis* as a positive control (16). CD630 cells had no activity but spores carried activity equivalent to that of *B. licheniformis* (see FIG. 9F). As with catalase and peroxiredoxin activity, the age of the spores had a marked effect on spore-associated activity with 7-day-old spores carrying 20% of the activity found in 2-day-old spores (see FIG. 9G).

The inventors wondered whether chitinase activity might be enhanced by disruption of the spore coat and exosporium. To address this, they used two approaches, firstly, by measuring activity following spore germination which would rupture the spore coat, and second, following sonication of spores which would remove the exosporium. Spore germination of 1-day old spores was evaluated using different solutions of sodium taurocholate as the germinant (10). By measuring the change in $OD_{580}$ attributed to phase-darkening of spores, the inventors identified 3% and 5% sodium taurocholate as optimal for spore germination with a 38% (3%) to 50% (5%) reduction in $OD_{580}$ in 30 minutes (see FIG. 9H). Next, 30 minutes following germination using 3% and 5% sodium taurocholate, they measured chitinase activity. They found that compared to untreated spores the germinant produced a marked increase (21%) in chitinase activity with both 3% and 5% solutions (see FIG. 9I). Using commercially obtained chitinase (Sigma C6242), the inventors determined that sodium taurocholate had no effect on enzyme activity (data not shown). They also found that chitinase activity was released into the medium following spore germination. Using 3% germinant, activity was clearly detectable in the supernatant fraction following centrifugation in contrast to spore samples that had not been germinated (see FIG. 9J).

In support of this, they subjected suspensions of 7-day-old spores to increasing cycles of sonication. Seven 3-second bursts of sonication yielded more chitinase activity than two, which in turn was greater than untreated spores (see FIG. 9K). As was the case during spore germination, sonication was sufficient to release chitinase activity into the medium (see FIG. 9L). These results demonstrate firstly, that catalase, peroxiredoxin and chitinase activity are associated with spores, second, that activity declines as spores mature demonstrating that either the enzyme is not required or is rendered latent. Finally, for chitinase, activity is enhanced if the spore exosporium and/or coat is disrupted.

Discussion

This study has provided an initial examination of the spore coats of *C. difficile* spores and despite identifying five spore coat proteins, the inventors believes that they could represent just a small fraction of the total protein component. For example, in *B. subtilis* more than 70 proteins are thought to be found in the coat layers (11). The inventors have demonstrated, using immunodecoration, that all five proteins were present on the outermost layers of the coat. Since the exosporial outer layer is fragile, these proteins might lie in the outer exosporium, or potentially in the outer coat layer that would be exposed if the exosporium is shed.

One of the most surprising observations was the enzymatic properties of the spores and the identification of at least three enzymatic coat proteins (CotCB, CotD and CotE), that most probably reside in the exosporium. Although absolute confirmation will require inactivation of the chromosomal genes, this assumption is supported by several lines of evidence. Firstly, vegetative cells were shown to exhibit no enzyme activity so this cannot arise from any contaminating cells. Secondly, analysis of the spore proteome has revealed no additional genes that could encode these enzyme activities.

The functions of these spore-associated enzymes are currently unknown. The catalase (CotCB and CotD) and peroxiredoxin (CotE) activities are antioxidants and at first glance all three would reduce the cellular toxicity of $H_2O_2$ by conversion to oxygen and water. In the case of *C. difficile*, which is a strict anaerobe the presence of oxygen would, in turn, be harmful to the cell. Since the cell is irreversibly committed to dormancy it is conceivable that this is not actually harmful. However, the inventors believe that there is a need to remove $H_2O_2$. Studies made on *B. subtilis* sporulation show that $H_2O_2$ plays a key role in spore coat synthesis and serves as a substrate in the oxidative cross-linking of spore coat monomers. Here, the enzyme superoxide dismutase (SodA) is essential to the cross-linking of tyrosine-rich spore coat proteins. sodA mutants have been shown to produce spores with defective spore coats and reduced resistance properties and a major, tyrosine-rich, spore coat protein CotG is believed to be polymerized (by the formation of di-tyrosine cross-links) under the combined action of SodA and a putative peroxidase. SodA is responsible for producing $H_2O_2$ (and $O_2$) that, in turn, is used as a substrate for the peroxidase that catalyses the formation of di-tyrosine cross-links.

In CD630, a manganese-dependant SodA orthologue has been identified in the spore proteome (CD1631). CotE, as a 1-cys-peroxiredoxin would be expected to have the same enzymatic activity as a peroxidase. Thus, although not wishing to be bound by theory, the inventors postulate that in *C. difficile*, CotE would participate in the cross-linking of tyrosine-rich spore coat proteins. None of the other coat proteins identified in this work are tyrosine rich but examination of the *C. difficile* genome has revealed at least one gene (CD0597) that would encode a tyrosine rich protein (10.34% tyrosines). This protein is homologous to CotJB of *B. subtilis* and in *C. difficile* its ORF lies immediately upstream of cotCB which, in turn, encodes an orthologue of *B. subtilis* CotJC. The ORFs are separated by 61 bp and probably lie within the same operon. In this model, catalase might serve an important role in removing excessive levels of $H_2O_2$ that accumulate during spore coat biosynthesis and the fact that two manganese catalases are present in the spore suggests that there is an important requirement for $H_2O_2$ detoxification. In *C. difficile* strain QCD-32g58, a SodA orthologue is present which is found in the exosporium of *B. anthracis* and *B. cereus* suggesting that in *C. difficile*, SodA could also reside in this layer. Taken together, this indicates that one important role for the exosporium is in spore coat assembly and polymerization of spore coat protein monomers. This would explain why, as shown here, after spore maturation is complete, mechanical removal of the exosporium can be lost without apparent loss to spore function or viability.

For chitinase activity, the presence of this enzyme in the spore coat is intriguing, since it would be expected to be involved in the breakdown of fungi and other biological matter whether in the soil or in the intestine. However, spores are dormant, and so the inventors believe without being bound to any theory, that chitinase activity may be released (or activated) during spore germination enabling a potential source of nutrients as the *C. difficile* cell emerges from its coats. The inventors have provided compelling evidence to support this. Firstly, chitinase activity decreased as spores matured but increased during both spore germination and secondly, following sonication; both of these being events that would rupture the spore coat layers.

Another surprising aspect to CotE is its bifunctionality and one of a growing number of 'moonlighting proteins', which carry multiple functions including a mammalian protein, 1-cys-peroxiredoxin, that carries peroxidase and phospholipase activities. There is possibly a more important consequence of a chitinase and peroxiredoxin displayed on the surface of *C. difficile* spores that should not be overlooked. This relates to the potential link between peroxiredoxins, chitinases and inflammation. Peroxiredoxin 1 (a 2-cys-peroxiredoxin), secreted from tumour cells (17), has been shown to induce proinflammatory cytokines in macrophages via interaction with Toll-like receptor 4 and to promote chronic inflammation which could support tumour growth (18). Regarding chitinases, it is now clear that some inflammatory conditions of the GI-tract (inflammatory bowel disease, IBD and ulcerative colitis, UC) lead to induction of host-cell chitinases by triggering the increased uptake of intracellular bacteria by colonic cells (19, 20) and in potentiating the development of epithelial tumorigenesis (21). Considering that some symptoms of CDAD resemble both IBD and UC the *C. difficile* chitinase is believed to play a direct role in infection and not simply in macromolecular degradation. Accordingly, the inventors are of the view that inhibiting the activity of this enzyme (i.e. CotE) could be used to reduce or prevent or treat *C. difficile* infections. Indeed, as described in Example

EXAMPLE 2

Use of *C. difficile* Protein as a Vaccine Antigen

Based on their isolation of the five *C. difficile* spore coat proteins, CotA, CotB, CotCB, CotD or CotE, the inventors set out to produce a *C. difficile* vaccine using these coat proteins as an antigen, as follows.

Figure 10:
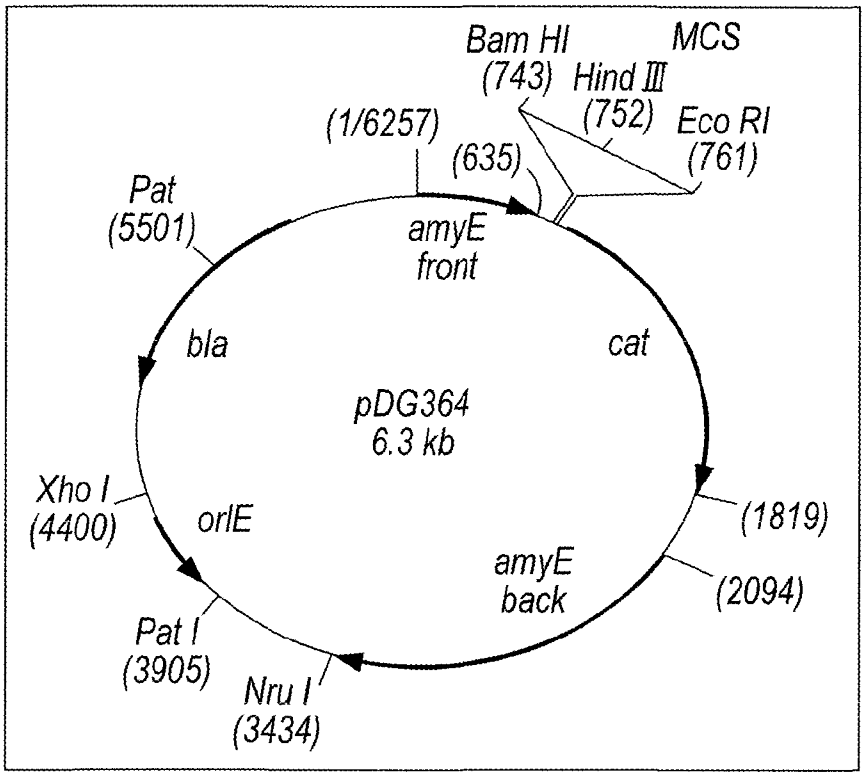

The sequence of a designated *C. difficile* gene, denoted herein cotX (i.e. CotA, CotB, CotCB, CotD or CotE) encoding one of the novel spore coat proteins, was first cloned into a vector, such as pDG364 shown in FIG. 10. This vector enabled the ectopic (trans) insertion into *Bacillus subtilis* (see FIG. 11).

Firstly, the coding sequence of the designated cotX ORF (i.e. SEQ ID No. 6-10) was identified. Secondly, the DNA sequence of this gene was spliced into any known gene from *B. subtilis* that encodes a known protein, which is referred to as Gene X or Protein X, for example CotB of *B. subtilis*. PCR was used in order to create a hybrid gene that would encode Protein X from *B. subtilis* fused at its C-terminus to CotX (i.e. CotA, CotB, CotCB, CotD or CotE). The plasmid vector, pDG364, was used to facilitate cloning, which was carried out first in *E. coli* and then *B. subtilis*. The plasmid vector carried the 5' sequences of the target *B. subtilis* gene with its natural promoter to enable expression of the *B. subtilis* gene.

The plasmid was able to integrate into the *B. subtilis* chromosome by a single or double crossover recombination event. This was achieved by the plasmid carrying a drug-resistance gene that was selectable in *B. subtilis*, for example chloramphenicol resistance.

Figure 11:
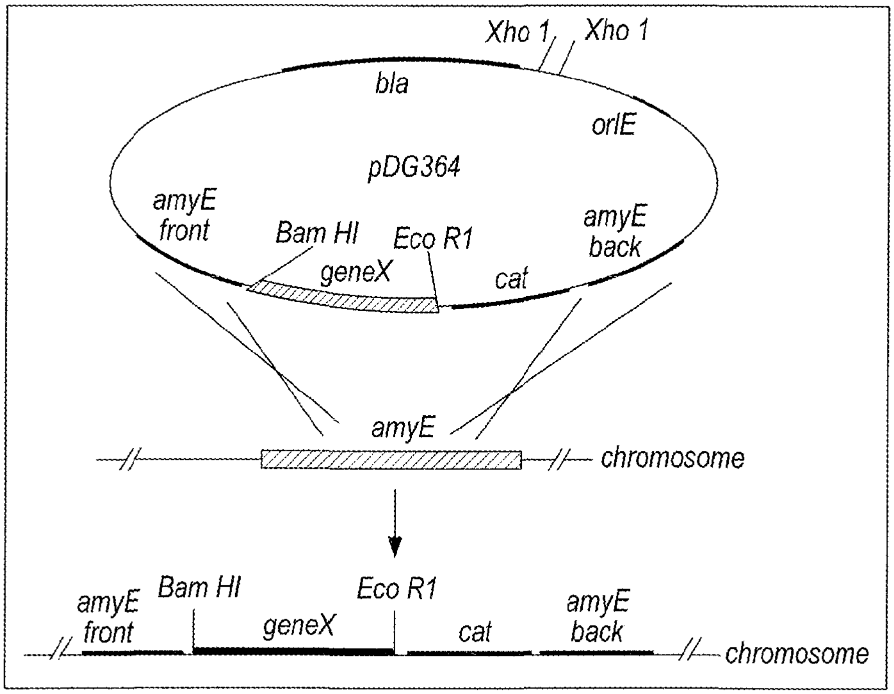
FIG. 11 illustrates the double-crossover recombinational event that generates a partial diploid using the cloning vector pDG364.

After confirmation of the plasmid clone, the plasmid was then linearised and introduced into *B. subtilis* cells (by DNA-mediated transformation or electroporation). Selection was made for drug resistance carried by the plasmid and now introduced into the genome. As shown in FIG. 11, the crossover event was designed to occur in amyE (i.e. an alpha amylase), which facilitated screening of positive clones in *B. subtilis* on appropriate selection plates.

The entire *C. difficile* cotD gene was used for fusion, while for *B. subtilis*, cotB, a 3'-deletion was used so that the encoded CotB segment was 33 kDa. CotD was integrated into the chromosome by a stable, double crossover, recombination event, and was placed in trans to the indigenous cotB gene of *B. subtilis.*

Construction of Recombinant *B. subtilis* Strains

The general strategy for constructing strains carrying chimeric genes has been reported in references 22-25, and is summarised as follows.

Step 1

The *C. difficile* cotD gene including its sporulation-specific promoter was cloned in either pDG364 (see FIG. 10) or pDG1664 using primers CotDF and CotDR for cotD (see Table 3).

TABLE 3

PCR primers

| Primer | Direction | Sequence[1] | Restriction site |
|---|---|---|---|
| CotDF | forward | CCC*AAGCTT*GCC**ATGTGGATATATCAGAAAAC** (SEQ ID No: 21) | HindIII |
| CotDR | reverse | G*GAATTC*TTA**TTACAACATTTTTTGAGATTC** (SEQ ID No: 22) | $EcoR_1$ |
| CotBF | forward | GC*GGATCC*ACGGATTAGGCCGTTTGTCC (SEQ ID No: 23) | BamHI |
| CotBR | reverse | CCC*AAGCTT***GGATGATTGATCATCTGAAG** (SEQ ID No: 24) | HindIII |

[1]restriction site is in italics;
bold = *C. difficile* or *B. subtilis* sequence is in bold.

Expression of the hybrid gene was confirmed using Western blotting and probing of size-fractionated proteins (SDS-PAGE) using antibodies that recognize the introduced antigen (i.e. CotA-E). If the *C. difficile* gene fused to the *B. subtilis* gene was then expressed, and a new band appeared which was recognized only by the antibody and not normally found in *B. subtilis*. Other techniques that could be used are immunofluorescence microscopy (FIG. 12) and FACS analysis that can show surface expression of antigens on the spore surface. Spores of recombinant *B. subtilis* that expressed the *C. difficile* antigen (i.e. CotA, CotB, CotCB, CotD or CotE) were then made, and used to dose groups of inbred mice by the oral (intra-gastric), intra-nasal or parenteral routes. A suitable dosing regime was used, normally 3 doses at 2-week intervals. Blood was withdrawn for analysis of serum (IgG) responses. Saliva, vaginal fluids or faeces was taken for analysis of mucosal (secretory IgA).

Indirect ELISA was used to analyse antibody responses in serum and mucosal samples. However, cellular responses could also be examined using splenocytes recovered from sacrificed mice. Splenocytes were then stimulated with the *C. difficile* antigen, and cytokines were determined using ELISA or ELISPOT analysis.

Recombinant *B. subtilis* Vaccine Strains

In the example discussed below, *C. difficile* toxin gene, CotD (i.e. SEQ ID No. 4), was fused to the spore coat protein, CotB, of *B. subtilis*. It should be noted that the *B. subtilis* CotB protein is unrelated to *C. difficile* CotB.

*B. subtilis* (BS) merodiploid strains contained a chimeric gene of cotB fused at its 3'-end to the *C. difficile* cotD gene.

For cotB of *B. subtilis*, the 3'-codon (codon 275, serine) was used producing a truncated cotB gene (the entire cotB ORF is 380 codons long) encoding a 33 kDa species. These plasmids enable cloned genes to be integrated into the chromosome of *B. subtilis* by a double crossover recombinational event occurring at either the amyE (pDG364, see FIG. 11) or thrC loci (pDG1664) by selection for either chloramphenicol (pDG364) or erythromycin (pDG1664) resistance, as shown in FIG. 11.

Step 2

*C. difficile* CotD-Primers (see Table 3) were designed to enable restriction and ligation, in frame, to the cotB 3'-termini contained in the pDG364 or pDG1664 clones described in Step 1. *C. difficile* cotD primers (CotDF and CotDR) were designed to amplify DNA of the entire *C. difficile* cotD ORF. Recombinant plasmids were sequenced to confirm the integrity of the cloning.

Step 3

Plasmids were then linearised by restriction digestion and then introduced into competent cells of *B. subtilis* PY79 (a laboratory strain of *B. subtilis*). Chloramphenicol-resistant (pDG364-derived) or erythromycin-resistant (pDG1664-derived) transformants (depending on whether the cloned genes integrated into the chromosome of *B. subtilis* at the amyE (pDG364, see FIG. 11) or thrC loci (pDG1664)) were then colony-purified, and checked by PCR and finally by immunoblotting for expression of the appropriate chimeric protein, i.e. *C. difficile* CotD fused to *B. subtilis* CotB. The recombinant strain that carried the *C. difficile* CotD ORF fused to *B. subtilis* CotB and integrated at the amyE locus (CmR) was named, PP202.

Results

Expression of the C-Terminal Domain of CotD of *C. difficile* Toxin on *B. subtilis* Spores

Figure 12:
FIG. 12 shows the expression of *C. difficile* CotD on the surface of *B. subtilis* PP202 spores (FITC-labelling using anti-CD CotD antibodies). PY79 control spores gave no labelling (not shown)

*B. subtilis* was engineered to express the *C. difficile* CotD protein on the outermost layer of the spore coat. Expression was achieved by fusing *C. difficile* CotD to the C-terminus of the *B. subtilis* outer spore coat protein CotB (43 kDa) which has successfully been used for surface display and mucosal delivery of heterologous antigen. Recombinant spores of this construct were named PP202. Surface expression of *C. difficile* CotD on *B. subtilis* PP202 spores was confirmed by confocal imaging of spores, as shown in FIG. 12.

Figure 13:
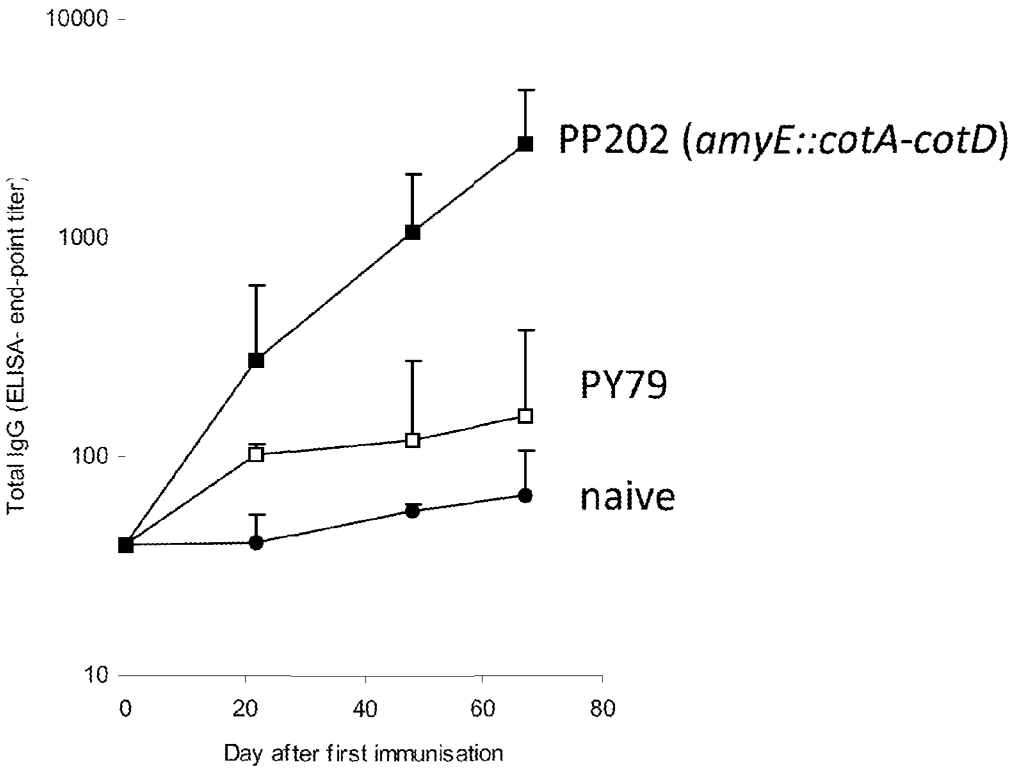
FIG. 13 shows *C. difficile* CotD-specific IgG titres determined by indirect ELISA in mice immunised orally (3 orogastric doses, days 1, 16, 32) with non-recombinant PY79 spores or spores of PP202 (expressing CD CotD on the surface of BS spores)

Oral Delivery of the PP202 (*B. subtilis* CotD) Spores Induces Systemic and Mucosal Antibodies Immune responses were determined in mice dosed orogastrically (o.g.) with PP202 spores, as shown in FIG. 13. Control groups included, naïve and groups dosed (o.g.) with non-recombinant spores (PY79). In addition, we included one group dosed (o.g.) with *C. difficile* CotB protein (10 μg).

Figure 14:
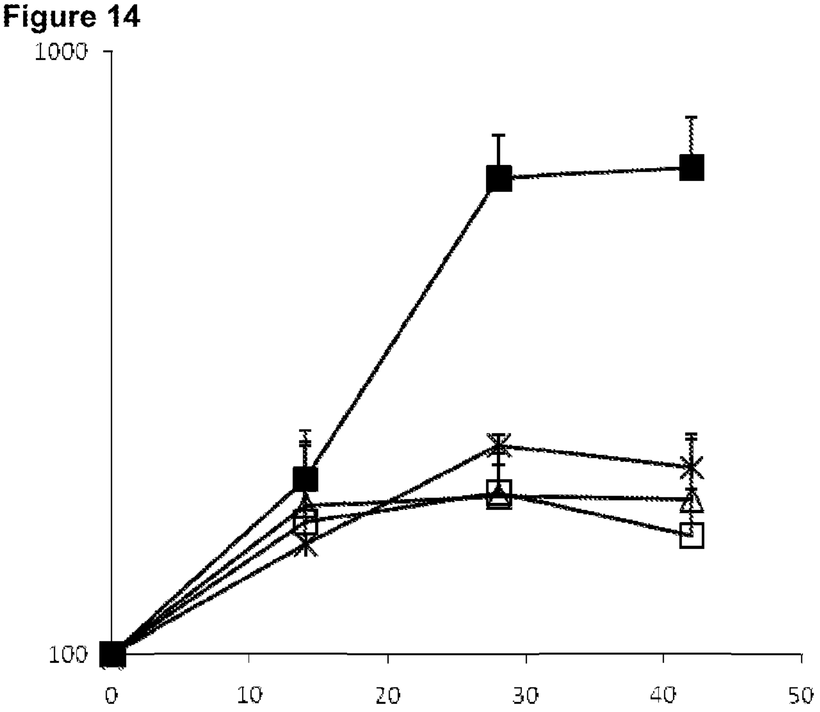
FIG. 14 shows secretory IgA (sIgA) responses in mice dosed orally (3 doses) with PP202 spores, non-recombinant PY79 spores and naïve animals (days 1, 16, 32). CotD-specific IgA titres determined by indirect ELISA from faecal samples.

Specific antibodies (serum IgG, and faecal IgA) against *C. difficile* CotD were measured by indirect ELISA, as shown in FIGS. 13 and 14. Compared to control groups (naïve mice, mice dosed with PY79 spores or mice receiving protein alone) significant ($p<0.01$) levels of CotD-specific IgG were detected in the serum of animals dosed with PP202. Seroconversion was also observed.

Secretory IgA (sIgA) was measured in faecal samples, as shown in FIG. 14 and anti-CotD responses were found to be particularly high with clear seroconversion in animals dosed with PP202 spores ($p<0.001$).

Protection in the Golden Syrian Hamster Model of Infection

Hamsters were given 3 o.g. doses (days 0, 14, 35) of recombinant spores (PP202; $2\times10^{10}$) and then challenged with 100 spores of *C. difficile* 630 ($A^+B^+$) on day 60. Control groups included naïve animals and a group dosed with non-recombinant PY79 spores. Colonisation of hamsters was recorded as the time from inoculation to signs of first symptoms when animals were killed. Animals showing no symptoms after 14 days were considered protected (i.e., the PP202 group).

TABLE 4

| Protection results | | | |
|---|---|---|---|
| Group/vaccine | Time (h) to $1^{st}$ symptoms | No. surviving | Protection |
| naive | 40.9 h (±1.3), | 0/8 | 0% |
| Non-recombinant PY79 spores | 53.2 h (±2.2) | 0/8 | 0% |
| PP202 | 55.6 h (±1.3), | 3/8 | 37.5% |

EXAMPLE 3

*C. difficile* Antigens Used in Diagnostic Kits

The inventors have also developed several embodiments of diagnostic kits, which detect the *C. difficile* infections by detecting CotA, CotB, CotCB, CotD or CotE. In some embodiments, the use, kit and/or method of the invention may each be used to detect the presence of a vegetative cell *Clostridium* spp. or *Bacillus* spp. in a sample, but it is preferred that spores are detected as the novel proteins are all found on the spore coat.

Method

Polyclonal antisera/antibodies (PAbs) and/or monoclonal antisera/antibodies (MAbs) were first made against each of the *C. difficile* spore coat proteins. Polyclonal sera was made using rabbits or mice. Monoclonal antibodies were generated in mice and screened.

Rationale:

A sample containing *C. difficile* was then mixed with antibodies (either polyclonal or monoclonal), and the antigen-antibody (Ag-Ab) complex was then evaluated using an appropriate method. The sample had to contain *C. difficile* spores since these display and carry the relevant antigens (Ag) that react with one of the five Cot antibodies (CotA-CotE). The sample was then treated according to existing methods for *C. difficile* diagnostic kits. *C. difficile* is normally diagnosed from faeces, and so a suitable method for sample preparation would be used.

Kit Formats to be Used are:

Three different embodiments of diagnostic kits have been developed:—

1) Latex agglutination—The antibody was mixed with a test sample, and a positive reaction was seen by agglutination of the Ab-Ag complex. The antibody was bound first to latex beads, increasing their size. In the presence of Ag, they form large dumps. This embodiment provides fast diagnosis of *C. difficile* with medium sensitivity.

Figure 15:
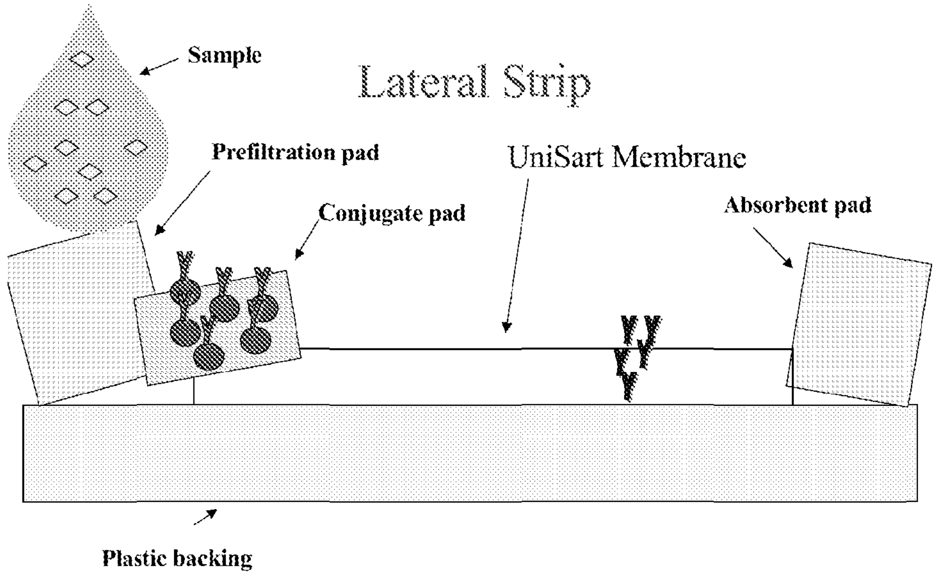
FIG. 15 is a schematic drawing of one embodiment of a diagnostic test kit (i.e. lateral strip) according to the invention used for diagnosing a *C. difficile* infection.
Figure 16:
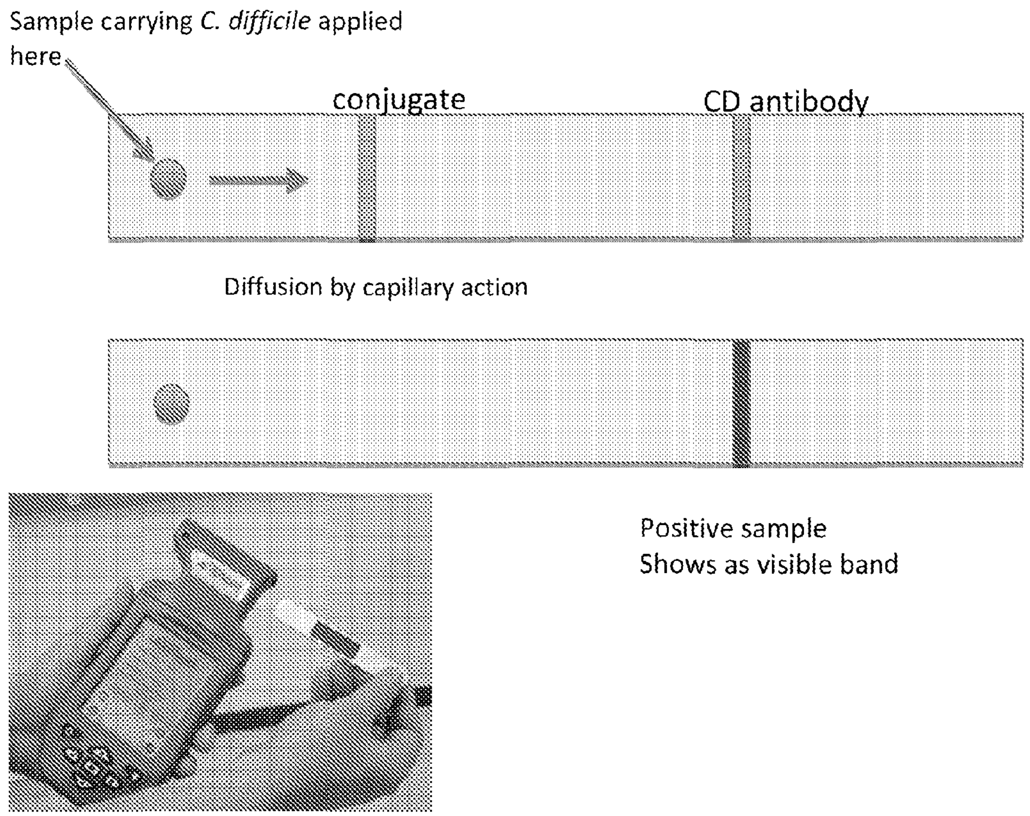
FIG. 16 shows a second embodiment of a diagnostic test kit (i.e. lateral flow test) in accordance with the invention used for diagnosing a *C. difficile* infection.
Figure 17:
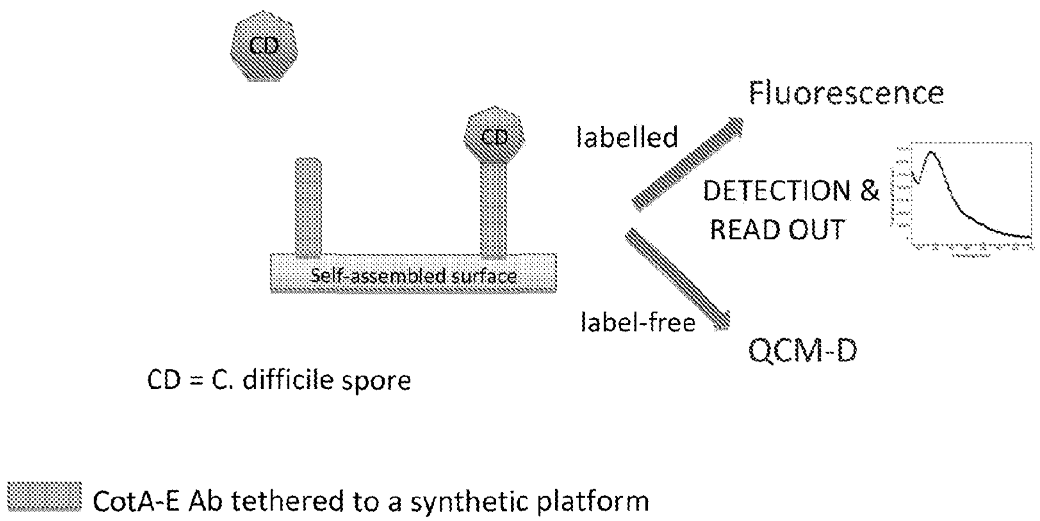
FIG. 17 shows a schematic drawing illustrating one embodiment of a high-sensitivity detection method according to the invention.

2) Lateral flow—This embodiment is illustrated in FIGS. 15 and 16. The *C. difficile* antibodies were applied as a thin strip to a suitable membrane strip. The strip was pre-soaked with a coloured reagent that would, in the presence of the Ag-Ab complex, form a colour that is visible to the naked eye. Usually, the strip is about 0.5-0.8 mm wide. The sample (containing *C. difficile* Ag) was applied as a drop to the end of the strip. As the aqueous sample diffuses through the membrane, it passes through a band of membrane carrying the coloured reagent. As it moves further, it reaches the band carrying the antibody where it will complex with the antibody and form a defined strip which, in the presence of the coloured reagent, will be visible to the naked eye as a thin line. This embodiment provides fast diagnosis of *C. difficile* with high sensitivity.

3) Dipstick—The antibody is applied to the end of a stick, similar to a cotton bud, but without the cotton. When the pre-coated dipstick is spotted onto a sample the Ag-Ab complex will be visualized using a secondary substrate.

Other more sensitive techniques can be used, all of which rely on the detection of Ag-Ab complexes. For example, the use of surface plasmon resonance (SPR), optical methods, fluorescence-based methods (see FIG. 20), magnetic particles can all be used to detect the Ag-Ab complexes. These methods are more time-consuming, but usually are designed for higher sensitivity. Unlike dipstick, agglutination and lateral flow methods they are quantitative in nature. In such embodiments, the sample is applied, and it then moves up the membrane strip (left to right). As it reaches the conjugate pad, it interacts with a reagent (known as the conjugate) that in the presence of the antibody will form a coloured band.

Other formats: Basic ELISA methods can also be used. In this embodiment, the sample is diluted and ELISA is used to detect Ag-Ab binding. By dilution of the sample, a good indication of the quantity of Ag can be determined.

EXAMPLE 4

Chitinase Inhibitor

As described in Example 1, the inventors have surprisingly found that CotE is a novel bifunctional protein with peroxiredoxin activity at its amino-terminus, and chitinase activity at its carboxy-terminus, i.e. it is a 1-cys-peroxiredoxin-chitinase. Its homology is closest to the Family 18 chitinases which are inhibited by methylxanthine drugs.

The inventors set out to evaluate a chitinase inhibitor, pentoxifylline, which is a methylxanthine (and is obtained from Sigma). This is a drug sold by Sanofi-Aventis as Trental and amongst other uses is used to reduce inflammation (e.g., TNF-alpha production).

$1\times10^8$ spores of *C. difficile* were re-suspended in 100 μl PBS (pH 7.4) containing various different concentrations of inhibitor. The substrate (4-Nitrophenyl N-acetyl-β-D-glucosaminide) was added to a final concentration of img/ml. The solution was then incubated at 37° C. for 3 h. 200 μl of sodium carbonate was added and the spore suspension was centrifuged for 1 min at max speed. The $OD_{405}$ was measured using 100 μl of supernatant.

Figure 18:
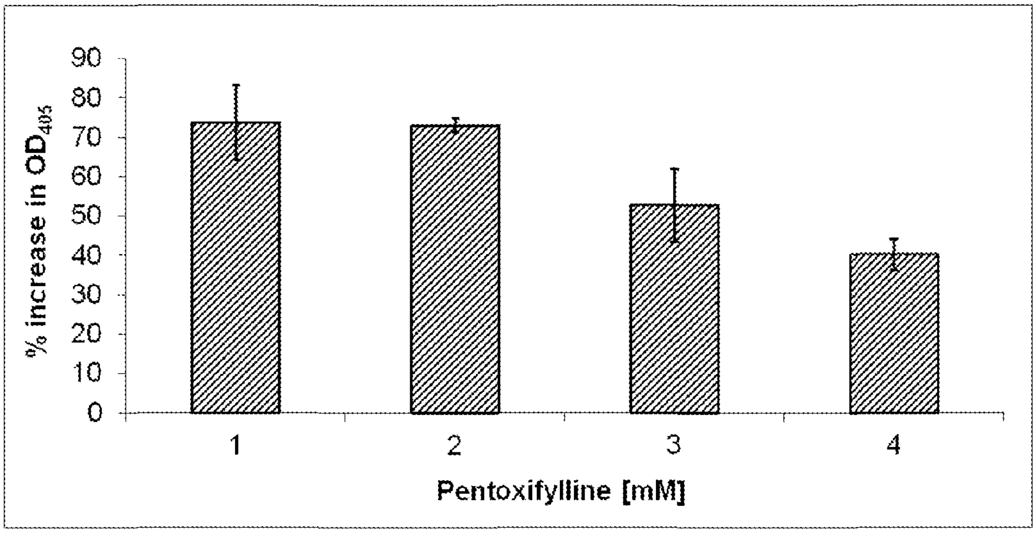
FIG. 18 is a barchart showing the inhibition of chitinase. The inhibitor is pentoxifylline (Sigma) and chitinase enzyme has been obtained from Sigma (*Trichoderma viridae*)
Figure 19:
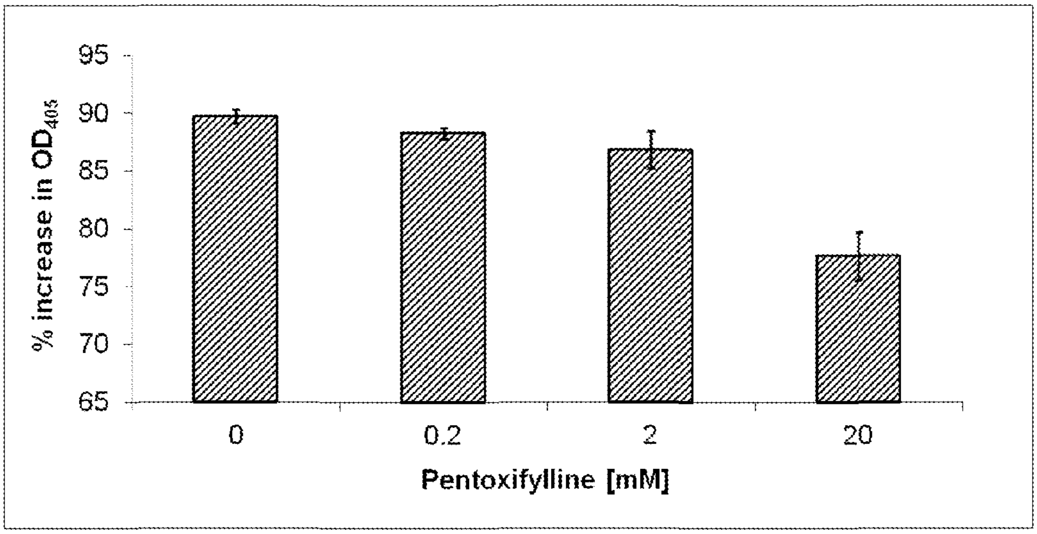
FIG. 19 is a barchart showing the inhibition of chitinase. Inhibition with pentoxifylline (Sigma) of chitinase of $1\times10^8$ spores of *C. difficile;*

The results are shown in FIGS. 18 and 19. The data show that pentoxifyline inhibits commercially obtained chitinase, as well as the chitinase activity obtained from spores of *C. difficile*.

EXAMPLE 5

Serum IgG is not Required for Protection to Relapse

The inventors carried out experiments using hamsters with PP108 spores (dosed on days 1, 14, 35 and 57 with $5\times10^{10}$ spores/dose of PP108) and induced *C. difficile* with clindamycin treatment and oral dosing with 100 CD630 spores. As shown in FIG. 20, spore counts in faeces rose to $10^6$ and then declined in agreement with other studies (26). Serum IgG responses to the C-terminus of *C. difficile* toxin A (CDTA), toxin A and toxin B, were measured as well as IgG responses to *C. difficile* 630 spores. CDTA is the carboxy-terminus of toxin A that is expressed on the surface of PP108 spores (28). Antibodies to CDTA react with toxin A but also cross-react to toxin B as shown elsewhere (28). Toxin levels in cecum samples were measured by ELISA as described in (28).

Toxin levels were cleared by neutralization (by either IgG or sIgA toxin specific antibodies) by day 3. Two further relapses were induced using clindamycin treatment (days 20 and day 33). Animals remained healthy with no symptoms of *C. difficile* infection (CDI) throughout but spore counts proliferated and then declined. Surprisingly, anti-toxA and anti-toxB titres declined so that, by day 33, protection against relapse could not be accounted for by IgG responses. Also measured were anti-CD spore responses. Strikingly, 1 day before CD630 spore challenge, the inventors could detect anti-CD spore responses, which suggested that immunization with PP108 spores was delivering a cross-reactive antigen. (nb, no responses in naïve animals). This experiment has now been repeated in full with the same result. Note that antibodies to toxin A cross-react with toxin B.

EXAMPLE 6

Anti-Toxin A Antibodies Cross-React with the *C. difficile* Spore Coat Protein CotE The inventors then conducted Western blotting using antibodies to the C-terminus of toxin A (CDTA) against purified recombinant proteins from the *C. difficile* spore coat. As shown in FIG. 21, anti-CDTA binds specifically to the CD spore coat protein CotE. Since PP108 spores express CDTA, in vaccinated animals this would account for the anti-CD spore titres observed.

Hamsters were then immunized orally using PP108 spores (expressing CDTA and as described in FIG. 20) or by intramuscular injection with CDTA (10 mg, days 0, 7, 28). FIG. 22 shows that IgG from bleeds reacted with CotE by ELISA. This shows that IgG specific to CDTA and therefore toxin A cross-reacts with CotE.

EXAMPLE 7

Toxin A and CotE Share a Similar Recognition Site

CotE and toxin A (TcdA) share no apparent homology based on alignment of their polypeptide sequences. Thus, the inventors assumed that antibody recognition must come from homology at a 3D structural level. However, CotE has been shown by the inventors to be a novel bifunctional protein that carries two enzymatic domains, an N-terminal peroxiredoxin domain and a C-terminal chitinase domain (29). The peroxiredoxin domain is likely to be involved in the removal of $H_2O_2$ that is produced during enzymatic cross-linking of the spore coats. The chitinase domain is intriguing and the inventors assume that, in the environment, this enzyme enables the degradation of macromolecules (e.g. chitin, cellulose) in the GI-tract.

However, CotE is surface exposed (29) and is a Group 8 chitinase which binds to the repeating (GlcNAc)n of chitins. By comparison, the receptor binding site of the *C. difficile* toxin A is thought to be Galα1-3Galβ1-4GlcNAc (27). The inventors believe that CotE can bind to the toxin A receptor using the GlcNAc motif. Initial studies using an ELISA method show that CotE can bind to the toxin A receptor ligand, as shown in FIG. 23, and obtained from DEXTRA. Laboratories Ltd. As shown, CotE demonstrated some level of binding whereas no binding was observed for toxin B.

EXAMPLE 8

Mucosal Antibodies Cannot Account for Protection to Relapse

The inventors then looked at mucosal responses. From the relapse analysis experiments shown in FIG. 20, the inventors examined the levels of IgG and IgA in faeces. As shown in FIG. 24, mucosal IgG and IgA specific to toxin A and toxin B were only present after the 1st relapse (sample shown is just before challenge with CD630). Mucosal antibodies therefore, while important for protection to primary infection may not alone account for protection to relapse. Note that antibodies to toxin A cross-react with toxin B.

EXAMPLE 9

Toxin Binding Assays

Rabbit red blood cells (RBC) carry the receptor that is recognized by toxin A and was used to define the most probable recognition motif for toxin A (27). The inventors used this assay to demonstrate that CotE can inhibit binding of toxin A. A solution of 5% fresh RBC when mixed with toxin A undergoes complete lysis. This can be measured using a spectrophotometer (OD542 nm). Controls are no toxin (PBS buffer) as a negative control with no lysis and a positive control 0.1% triton-X-100 as a positive control (complete lysis). When RBC lyse, the supernatant is removed after centrifugation and the OD542 is measured typically giving an OD reading of ~0.4 for complete lysis.

The data shown in Table 5 and demonstrates that CotE can competitively inhibit toxin A-mediated lysis of RBC.

TABLE 5

| Rabbit Red Blood Cell Assay of Toxin A Lysis | | | | |
|---|---|---|---|---|
| RBC | Toxin A | CotE | $OD_{542}$ | Lysis |
| 5% | 10 μg | — | 0.32 | +++ |
| 5% | 1 μg | — | 0.1 | + |
| 5% | 0.1 μg | — | 0.05 | (+) |
| 5% | 0.01 μg | — | <0.05 | - |
| 5% | 0.1% triton-X-100 | | 0.4 | ++++ |
| 5% | PBS buffer | — | <0.05 | - |
| 5% | 10 μg | 1 μg | 0.13 | + |
| 5% | 10 μg | 5 μg | 0.22 | ++ |
| 5% | 10 μg | 10 μg | 0.3 | +++ |
| 5% | 10 μg | 20 μg | 0.31 | +++ |
| 5% | 10 μg | 25 μg | 0.31 | +++ |

EXAMPLE 10

Model for Relapse and Remission

Based on the above studies, the inventors show that serum and mucosal antibody responses are clearly important for primary infection. They would achieve this by binding to toxin and preventing interaction with receptors. Antibodies to toxin A cross-neutralise toxin B, and so only toxin A may be required in a vaccine formulation. In the host, antibiotic therapy can disrupt the normal host microflora and induce germination of CD spores. This leads to rapid proliferation of live cells which secrete toxins. As a consequence of exhaustion of nutrients these cells will form spores which are then able to bind to the toxin A receptor by virtue of CotE, a chitinase on the spore surface and able to bind to the same recognition site.

FIG. 25 shows a model for Relapse and Remission. Spores and toxin A bind to the same receptor, in the case of spores, by virtue of the CotE chitinase on the spore surface.

EXAMPLE 11

Proof that CotE has Peroxiredoxin and Chitinase Activity

The inventors determined the Peroxiredoxin and Chitinase activities for CotE using the following assays.

Peroxiredoxin Activity

CotE was purified by a HiTrap chelating HPcolumn on a Pharmacia Akta liquid chromatography system. Protein fractions were dialysed over-night against PBS (pH 7.4). Peroxiredoxin activity was measured in 0.3 mM EDTA; 0.5M $KH_2PO_4$ and 150 mM $(NH_4)_2SO_4$ buffer with 250 μl M NAD, 500 μM $H_2O_2$, 4 μM Thioredoxin (from *E. coli*, Sigma) and 0.1 μM Thioredoxin reductase (from *E. coli*, Sigma) for 3 min at 37° C. As a positive control human 4 μg/ml peroxiredoxin 1 (Sigma, P8986) was used. Enzyme activity was calculated as percent difference from starting OD.

Chitinase Activity

CotE was purified by a HiTrap chelating HPcolumn on a Pharmacia Akta liquid chromatography system. Fractions containing the protein were dialysed over night against PBS. Protein concentration was measured and 0.5 mg/ml were incubated at 37° C. for 30 min with 1 mg/ml 4-Nitrophenyl N-acetyl-β-D-glucosamide as substrate. $OD_{405}$ was read every 30 sec. As a positive control 0.05 mg/ml chitinase from *Trichoderma viridae* (Sigma, C6242) was used. Enzyme activity was calculated as percent difference from starting OD.

As can be seen in FIG. 26, CotE carries both Peroxiredoxin and Chitinase activity.

References

1. Nicholson, W. L., and P. Setlow. 1990. Sporulation, germination and outgrowth. In *Molecular Biological Methods for Bacillus*. C. R. Harwood, and S. M. Cutting, eds. John Wiley & Sons Ltd., Chichester, UK. 391-450.
2. Paredes-Sabja, D., C. Bond, R. J. Carman, P. Setlow, and M. R. Sarker. 2008. Germination of spores of *Clostridium difficile* strains, including isolates from a hospital outbreak of *Clostridium difficile*-associated disease (CDAD). *Microbiology* 154:2241-2250.
3. Smith, C. J., S. M. Markowitz, and F. L. Macrina. 1981. Transferable tetracycline resistance in *Clostridium difficile. Antimicrob Agents Chemother* 19:997-1003.
4. Lawley, T. D., N. J. Croucher, L. Yu, S. Clare, M. Sebaihia, D. Goulding, D. J. Pickard, J. Parkhill, J. Choudhary, and G. Dougan. 2009. Proteomic and genomic characterization of highly infectious *Clostridium difficile* 630 spores. *J Bacteriol* 191:5377-5386.
5. Tsuzuki, T., and Y. Ando. 1985. Chemical studies on the spore coat protein of *Clostridium perfringens* type A. *Agricultural and Biological Chemistry* 49:3221-3225.
6. Hong, H. A., R. Khaneja, N. M. Tam, A. Cazzato, S. Tan, M. Urdaci, A. Brisson, A. Gasbarrini, I. Barnes, and S. M. Cutting. 2009. *Bacillus subtilis* isolated from the human gastrointestinal tract. *Res Microbiol* 160:134-143.
7. Beers, R. F., Jr., and I. W. Sizer. 1952. A spectrophotometric method for measuring the breakdown of hydrogen peroxide by catalase. *J Biol Chem* 195:133-140.
8. Logan, C., and S. G. Mayhew. 2000. Cloning, overexpression, and characterization of peroxiredoxin and NADH peroxiredoxin reductase from *Thermus aquaticus. J Biol Chem* 275:30019-30028.
9. Greetham, D., and C. M. Grant. 2009. Antioxidant activity of the yeast mitochondrial one-Cys peroxiredoxin is dependent on thioredoxin reductase and glutathione in vivo. *Mol Cell Biol* 29:3229-3240.
10. Wilson, K. H., M. J. Kennedy, and F. R. Fekety. 1982. Use of sodium taurocholate to enhance spore recovery on a medium selective for *Clostridium difficile. J Clin Microbiol* 15:443-446.
11. Henriques, A. O., and C. P. Moran, Jr. 2007. Structure, assembly, and function of the spore surface layers. *Annu Rev Microbiol* 61:555-588.
12. Sebaihia, M., B. W. Wren, P. Mullany, N. F. Fairweather, N. Minton, R. Stabler, N. R. Thomson, A. P. Roberts, A. M. Cerdeno-Tarraga, H. Wang, M. T. Holden, A. Wright, C. Churcher, M. A. Quail, S. Baker, N. Bason, K. Brooks, T. Chillingworth, A. Cronin, P. Davis, L. Dowd, A. Fraser, T. Feltwell, Z. Hance, S. Holroyd, K. Jagels, S. Moule, K. Mungall, C. Price, E. Rabbinowitsch, S. Sharp, M. Simmonds, K. Stevens, L. Unwin, S. Whithead, B. Dupuy, G. Dougan, B. Barrell, and J. Parkhill. 2006. The multidrug-resistant human pathogen *Clostridium difficile* has a highly mobile, mosaic genome. *Nat Genet.* 38:779-786.
13. Redmond, C., L. W. Baillie, S. Hibbs, A. J. Moir, and A. Moir. 2004. Identification of proteins in the exosporium of *Bacillus anthracis. Microbiology* 150:355-363.
14. Low, F. M., M. B. Hampton, A. V. Peskin, and C. C. Winterbourn. 2007. Peroxiredoxin 2 functions as a non-catalytic scavenger of low-level hydrogen peroxide in the erythrocyte. *Blood* 109:2611-2617.
15. Poole, L. B., M. Higuchi, M. Shimada, M. L. Calzi, and Y. Kamio. 2000. *Streptococcus mutans* H2O2-forming NADH oxidase is an alkyl hydroperoxide reductase protein. *Free Radic Biol Med* 28:108-120.

16. Tharisman, A., M. T. Suhartono, M. Spindler-Barth, J.-K. Hwang, and Y.-R. Pyun. 2005. Purification and characterization of a thermostable chitinase form *Bacillus licheniformis* Mb-2. *World Journal of Microbiology & Biotechnology* 21:733-738.
17. Neumann, C. A., D. S. Krause, C. V. Carman, S. Das, D. P. Dubey, J. L. Abraham, R. T. Bronson, Y. Fujiwara, S. H. Orkin, and R. A. Van Etten. 2003. Essential role for the peroxiredoxin Prdxi in erythrocyte antioxidant defence and tumour suppression. *Nature* 424:561-565.
18. Riddell, J. R., X. Y. Wang, H. Minderman, and S. O. Gollnick. 2010. Peroxiredoxin 1 stimulates secretion of proinflammatory cytokines by binding to $TLR_4$. *J Immunol* 184:1022-1030.
19. Kawada, M., C. C. Chen, A. Arihiro, K. Nagatani, T. Watanabe, and E. Mizoguchi. 2008. Chitinase 3-like-1 enhances bacterial adhesion to colonic epithelial cells through the interaction with bacterial chitin-binding protein. *Lab Invest* 88:883-895.
20. Kawada, M., Y. Hachiya, A. Arihiro, and E. Mizoguchi. 2007. Role of mammalian chitinases in inflammatory conditions. *Keio J Med* 56:21-27.
21. Eurich, K., M. Segawa, S. Toei-Shimizu, and E. Mizoguchi. 2009. Potential role of chitinase 3-like-1 in inflammation-associated carcinogenic changes of epithelial cells. *World J Gastroenterol* 15:5249-5259.
22. Isticato, R., G. Cangiano, H. T. Tran, A. Ciabattini, D. Medaglini, M. R. Oggioni, M. De Felice, G. Pozzi, and E. Ricca. 2001. Surface display of recombinant proteins on *Bacillus subtilis* spores. *Journal of Bacteriology* 183:6294-6301.
23. Duc le, H., H. A. Hong, H. S. Atkins, H. C. Flick-Smith, Z. Durrani, S. Rijpkema, R. W. Titball, and S. M. Cutting. 2007. Immunization against anthrax using *Bacillus subtilis* spores expressing the anthrax protective antigen. *Vaccine* 25:346-355.
24. Hoang, T. H., H. A. Hong, G. C. Clark, R. W. Titball, and S. M. Cutting. 2008. Recombinant *Bacillus subtilis* expressing the *Clostridium perfringens* alpha toxoid is a candidate orally delivered vaccine against necrotic enteritis. *Infect Immun* 76:5257-5265.
25. Permpoonpattana, P., H. A. Hong, J. Phetcharaburanin, J. M. Huang, J. Cook, N. F. Fairweather, and S. M. Cutting. 2011. Immunisation with *Bacillus* spores expressing toxin A peptide repeats protects against infection with toxin A+ B+ strains of *Clostridium difficile. Infection and immunity.*
26. Goulding, D., H. Thompson, J. Emerson, N. F. Fairweather, G. Dougan & G. R. Douce, (2009) Distinctive profiles of infection and pathology in hamsters infected with *Clostridium difficile* strains 630 and B1. *Infect Immun* 77: 5478-5485.
27. Krivan, H. C., G. F. Clark, D. F. Smith & T. D. Wilkins, (1986) Cell surface binding site for *Clostridium difficile* enterotoxin: evidence for a glycoconjugate containing the sequence Gal alpha 1-3Gal beta 1-4GlcNAc. *Infection and immunity* 53: 573-581.
28. Permpoonpattana, P., H. A. Hong, J. Phetcharaburanin, J. M. Huang, J. Cook, N. F. Fairweather & S. M. Cutting, (2011a) Immunization with *Bacillus* spores expressing toxin A peptide repeats protects against infection with *Clostridium difficile* strains producing toxins A and B. *Infection and immunity* 79: 2295-2302.
29. Permpoonpattana, P., E. H. Tolls, R. Nadem, S. Tan, A. Brisson & S. M. Cutting, (2011b) Surface layers of *Clostridium difficile* endospores. *J Bacteriol* 193: 6461-6470.

The invention claimed is:

1. A *Clostridium difficile* detection kit, the kit comprising: an isolated polyclonal or monoclonal antibody which specifically binds to a polypeptide comprising the amino acid sequence as set out in SEQ ID NO: 5.

2. The *Clostridium difficile* detection kit according to claim 1 wherein the antibody specifically binds to the polypeptide when the polypeptide is in a spore of *Clostridium difficile*.

3. The *Clostridium difficile* detection kit according to claim 1 wherein the antibody specifically binds to the polypeptide when the polypeptide is in a sample which comprises faeces, blood, saliva or vaginal fluid.

* * * * *